(12) United States Patent
Sakashita et al.

(10) Patent No.: US 7,790,725 B2
(45) Date of Patent: *Sep. 7, 2010

(54) THIAZOLIDINE DERIVATIVES AND MEDICINAL USE THEREOF

(75) Inventors: Hiroshi Sakashita, Tokyo (JP); Tomohiro Yoshida, Tokyo (JP); Hiroshi Kitajima, Tokyo (JP); Masahiro Takeuchi, Tokyo (JP); Yoshihito Tanaka, Tokyo (JP); Takuya Yoshimura, Nara (JP); Fumihiko Akahoshi, Tokyo (JP); Yoshiharu Hayashi, Tokyo (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 57 days.

This patent is subject to a terminal disclaimer.

(21) Appl. No.: 11/774,941

(22) Filed: Jul. 9, 2007

(65) Prior Publication Data

US 2007/0259880 A1 Nov. 8, 2007

Related U.S. Application Data

(62) Division of application No. 10/489,622, filed as application No. PCT/JP02/009419 on Sep. 13, 2002, now abandoned.

(30) Foreign Application Priority Data

Sep. 14, 2001 (JP) ............................. 2001-279084
Sep. 28, 2001 (JP) ............................. 2001-304650

(51) Int. Cl.
*A61K 31/435* (2006.01)
*A61K 31/496* (2006.01)
*C07D 401/04* (2006.01)
*C07D 401/14* (2006.01)
*C07D 403/04* (2006.01)
*C07D 403/14* (2006.01)

(52) U.S. Cl. .................. 514/254.01; 514/326; 544/372; 546/208

(58) Field of Classification Search ................. 544/372; 546/208
See application file for complete search history.

(56) References Cited

U.S. PATENT DOCUMENTS

| | | | |
|---|---|---|---|
| 5,462,928 A | 10/1995 | Bachovchin et al. | |
| 6,716,843 B2 * | 4/2004 | De Nanteuil et al. | 514/237.2 |
| 7,074,794 B2 | 7/2006 | Kitajima et al. | |
| 2002/0198205 A1 | 12/2002 | Himmelsbach et al. | |
| 2004/0077645 A1 | 4/2004 | Himmelsbach et al. | |
| 2004/0106655 A1 | 6/2004 | Kitajima et al. | |

FOREIGN PATENT DOCUMENTS

| | | | |
|---|---|---|---|
| CA | 2333603 | A1 | 11/2000 |
| DE | 198 26 972 | A1 | 12/1999 |
| EP | 0 450 352 | A1 | 10/1991 |
| EP | 1 245 568 | A1 | 10/2002 |
| JP | 2002-265439 | A | 9/2002 |
| WO | WO 95/15309 | A1 | 6/1995 |
| WO | WO 98/19998 | A2 | 5/1998 |
| WO | WO 99/61431 | A1 | 12/1999 |
| WO | WO 01/81337 | A1 | 11/2001 |
| WO | WO 02/14271 | A1 | 2/2002 |
| WO | WO 02/068420 | A1 | 9/2002 |

OTHER PUBLICATIONS

Diabetes Guide [online], [retrieved from the Internet on Jun. 17, 2008] [URL; http://diabetes. webmd.com/guide/diabetes-overview].*
Huff, J. HIV Protease; A Novel Chemotherapeutic Target for AIDS. J. Med.Chem. (1991), 34, 2305-2314.*
Autoimmune Diseases [online], [retrieved on Aug. 27, 2007]. Retrieved from the Internet, URL; http://www.nlm.nih.gov/medlineplus/autoimmunediseases.html>.*
Document No. 136:200479 from CAPLUS, retrieved on Oct. 5, 2009.*
Ashworth et al., *Bioorganic & Medicinal Chemistry Letters*, 6(10): 1163-1166 (1996).
Augustyns et al., *Current Medicinal Chemistry*, 6: 311-327 (1999).
Augustyns et al., *Eur. J. Med. Chem.*, 32: 301-309 (1997).
Callebaut et al., *Science*, 262: 2045-2050 (1993).
Chisholm et al., *J. Org. Chem.*, 65(22): 7541-7553 (2000).
Deacon et al., *Journal of Clinical Endocrinology and Metabolism*, 80(3): 952-957 (1995).
Deacon et al., *American Journal of Physiology*, 271: E458-E464 (1996).
Heymann et al., *FEBS Letters*, 91(2): 360-364 (1978).
Johnson et al., *Journal of Cell Biology*, 121: 1423-1432 (1993).
Knudsen et al., *European Journal of Pharmacology*, 318: 429-435 (1996).
Schon et al., *Biomedica Biochimica Acta*, 44(2): K9-K15 (1985).

* cited by examiner

*Primary Examiner*—Rebecca L Anderson
*Assistant Examiner*—Shawquia Young
(74) *Attorney, Agent, or Firm*—Leydig, Voit & Mayer, Ltd.

(57) ABSTRACT

A thiazolidine derivative represented by the formula (I)

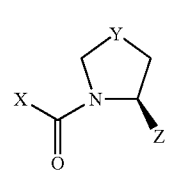

wherein each symbol is as defined in the specification, and a pharmaceutically acceptable salt thereof exhibit a potent DPP-IV inhibitory activity, and can be provided as an agent for the prophylaxis or treatment of diabetes, an agent for the prophylaxis or treatment of obesity and the like.

5 Claims, No Drawings

THIAZOLIDINE DERIVATIVES AND MEDICINAL USE THEREOF

CROSS-REFERENCE TO RELATED APPLICATIONS

This patent application is a divisional of copending U.S. patent application Ser. No. 10/489,622, filed Apr. 21, 2004.

TECHNICAL FIELD

The present invention relates to a thiazolidine derivative showing a dipeptidyl peptidase IV (DPP-IV) inhibitory activity and useful for the prophylaxis or treatment of diseases in which DPP-IV is involved, particularly, diabetes, obesity and the like, and a salt thereof.

BACKGROUND ART

DPP-IV is a serine protease that recognizes an amino acid sequence having proline (may be alanine, hydroxyproline) at the penultimate position from the N-terminal and produces dipeptide Xaa-Pro (wherein Xaa shows an optional amino acid and Pro shows L-proline). It is known that DPP-IV is widely distributed in the mammalian tissues, particularly in blood, kidney, intestinal epitherlium and placenta.

While the physiological role of DPP-IV in mammal has not been clarified completely, its involvement in a broad range of biological functions such as degradation of neuro-peptide [Heymann et al., FEBS Letters, vol. 91, pp. 360-364 (1978)], activation of T cell [Schon et al., Biomedica Biochimica Acta, vol. 44, pp. K9-K15 (1985)], adhesion of metastatic tumor cells to endothelium [Johnson et al., Journal of Cell Biology, vol. 121, pp. 1423-1432 (1993)], invasion of HIV virus into lymphocyte [Callebaut et al., Science, vol. 262, pp. 2045-2050 (1993)] and the like has been clarified. Of these, the role of DPP-IV as an enzyme that inactivates a biological substance glucagon-like peptide (GLP-1) having a potent insulin secretagogue action, which controls postprandial blood glucose level, has been drawing attention [Deacon et al., Journal of Clinical Endocrinology and Metabolism, vol. 80, pp. 952-957 (1995)].

It is known that GLP-1 is metabolized in several minutes in living organisms. In this respect, metabolism by DPP-V is particularly important, where it rapidly cleaves GLP-1 and produces inactive GLP-1 [Deacon et al., American Journal of Physiology, vol. 271, pp. E458-E464 (1996)]. In addition, since the inactive GLP-1 shows an antagonistic action against GLP-1 receptor, the physiological action of GLP-1 is considered to be further attenuated [Knudsen et al., European Journal of Pharmacology, vol. 318, pp. 429-435 (1996)]. Therefore, a method for suppressing degradation of GLP-1 by DPP-IV inhibition is considered the best approach for enhancing the GLP-1 action, In other words, a DPP-IV inhibitor is expected to be a superior treatment method for correcting postprandial hyperglycemia of non-insulin dependent diabetic (type 2 diabetes) patients, without causing side effects such as prolonged hypoglycemia and the like.

Patent applications relating to DPP-IV inhibitors include the following.

JP-T-9-509921 discloses 1-[N-ε-(hydroxysuccinyl)-L-lysyl]pyrrolidine. This L-lysine moiety is limited to an acyl-substituted form.

JP-T-9-509921 discloses (S)-2-cyano-1-L-prolinepyrrolidine derivative. The L-α-amino acid corresponding to the L-proline moiety of the compound disclosed therein is characterized in that it has a hydrophobic side chain.

In addition, WO99/61431 describes that a compound comprising natural amino acid and thiazolidine or pyrrolidine shows a DPP-IV inhibitory activity.

While many DPP-IV inhibitors have been reported up to the present day [Augustyns et al., Current Medicinal Chemistry, vol. 6, pp. 311-327 (1999)], none of the compounds are sufficient in the inhibitory activity and stability and safety in living organisms, and are not satisfactory as pharmaceutical products. Therefore, the development of a compound having a therapeutic effect based on a DPP-IV inhibitory action and satisfactory as a pharmaceutical product has been desired.

DISCLOSURE OF THE INVENTION

In view of the above, the present inventors conducted intensive studies with the aim of developing a novel DPP-IV inhibitor. As a result, they found that a thiazolidine derivative having a hydrophilic amino group introduced into the side chain and a derivative having a substituent introduced into the γ-position of proline have a potent DPP-IV inhibitory activity, and they further enhanced the stability, which resulted in the completion of the present invention.

Accordingly, the present invention relates to the following compounds.

[1] A thiazolidine derivative represented by the formula (I):

wherein X is a substituent selected from the following formulas:

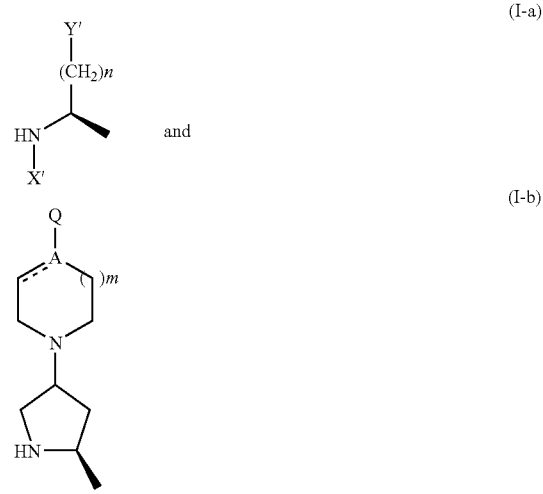

wherein m is an integer of 1 or 2, n is an integer of 1 to 5,

X' is a hydrogen atom or an alkyl optionally having substituent(s),

Y' is represented by —NR$^1$R$^2$ (R$^1$ is aryl optionally having substituent(s) or heteroaryl optionally having substituent(s), R$^2$ is a hydrogen atom, alkyl optionally having substituent(s), aryl optionally having substituent(s), arylalkyl optionally having substituent(s), heteroaryl optionally having substituent(s) or heteroarylalkyl optionally having substituent(s), or they may be bonded to each other to form a heterocycle having carbon and at least one nitrogen, optionally having other heteroatom(s) and optionally having substituent(s), where this heterocycle is optionally substituted or condensed with an aromatic ring optionally having substituent(s)), ----- is a single bond or a double bond, A is a carbon atom or a nitrogen atom,
wherein i) when A is a carbon atom, then A is optionally substituted by a hydroxyl group, carboxy or alkoxycarbonyl, and ii) when A is a nitrogen atom, then
----- is a single bond, and Q is aryl or heteroaryl selected from the compounds represented by the following formulas (II)-(XII):

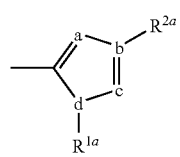
(II)

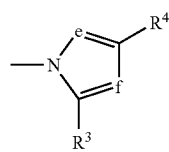
(III)

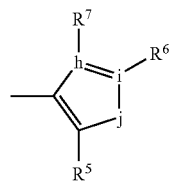
(IV)

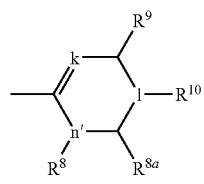
(V)

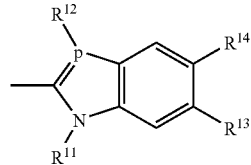
(VI)

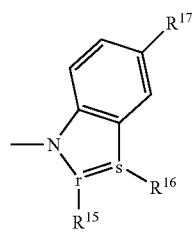
(VII)

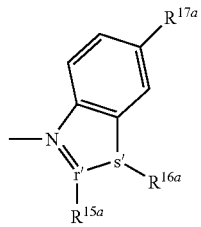
(VIII)

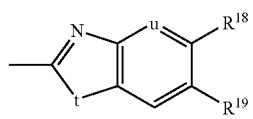
(IX)

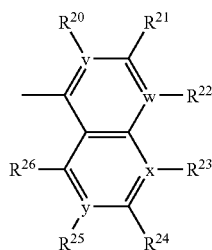
(X)

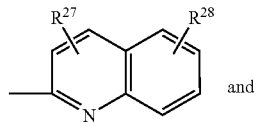
(XI)

and

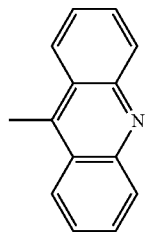
(XII)

wherein
(i) in the formula (II), 1 to 3 from a, b, c and d is(are) nitrogen atom(s) and the rest is(are) carbon atom(s) or all of them are nitrogen atoms,
R$^{1a}$ is alkyl, phenyl, pyridyl, pyrimidinyl, imidazolyl or oxazolyl, wherein these groups are optionally substituted by one or more from alkyl, alkoxy, halogen and cyano,
R$^{2a}$ is a hydrogen atom, alkyl or haloalkyl,
wherein
(i-1) when b is a nitrogen atom, then R$^{2a}$ is not present,
(i-2) when c and d are both nitrogen atoms, a and b are both carbon atoms, R$^{1a}$ is phenyl and R$^{2a}$ is alkyl, then R$^{1a}$ has one or more substituents mentioned above,
(i-3) when a and d are both nitrogen atoms, b and c are both carbon atoms and R$^{1a}$ is phenyl without substituent, then R$^{2a}$ is alkyl or haloalkyl, and
(i-4) when all of a, b, c and d are nitrogen atoms and R$^{1a}$ is phenyl, then (1) A of the formula (I-b) is a carbon atom and R$^{1a}$ does not have the above-mentioned substituent, or (2) R$^{1a}$ is substituted by one or more from alkyl and halogen,
(ii) in the formula (III), one of e and f is a nitrogen atom and the other is a carbon atom, or both are carbon atoms (same as "0-1 of e and f is a nitrogen atom and the rest is(are) carbon atom(s)"), and $R^3$ and $R^4$ may be the same or different and each is a hydrogen atom, alkyl, phenyl or pyridyl, (iii) in the formula (IV), j is a sulfur atom, an oxygen atom or a nitrogen atom, h and i may be the same or different and each is a nitrogen atom or a carbon atom (same as "0-2 of h and i is(are) nitrogen atom(s) and the rest is(are) carbon atom(s)"), $R^5$ and $R^7$ may be the same or different and each is a hydrogen atom, phenyl or pyridyl (when h is a nitrogen atom, then $R^7$ is absent), and $R^6$ is a hydrogen atom or alkyl (when i is a nitrogen atom, then $R^6$ is absent), (iv) in the formula (V), k, l and n' may be the same or different and each is a carbon atom or a nitrogen atom, wherein at least one is a carbon atom (same as "0-2 of k, l and n' is(are) nitrogen atom(s) and the rest is(are) carbon atom(s)"), $R^8$ is a hydrogen atom, phenyl, pyridyl or nitro (when n' is a nitrogen atom, then $R^8$ is absent), $R^{8a}$ is a hydrogen atom or phenyl, $R^9$ is a hydrogen atom, haloalkyl or cyano, and $R^{10}$ is a hydrogen atom or cyano (when l is a nitrogen atom, then $R^{10}$ is absent), wherein (iv-1) when k and n' are both nitrogen atoms, (1) A of the formula (I-b) is a nitrogen atom, and $R^{1a}$, $R^9$ and $R^{10}$ are all hydrogen atoms, or (2) $R^{8a}$ is phenyl and $R^9$ is haloalkyl, (iv-2) when k, l and n' are all carbon atoms, then $R^8$ is phenyl or pyridyl, (iv-3) when k is a nitrogen atom and l and n' are both carbon atoms, (1) $R^8$ is phenyl or nitro, or (2) $R^9$ is cyano, and (iv-4) when l is a nitrogen atom, then one of k and n' is a nitrogen atom, (v) in the formula (VI), p is a nitrogen atom or a carbon atom, $R^{11}$ is a hydrogen atom, phenyl or pyridyl (when p is a nitrogen atom, then $R^{11}$ is phenyl or pyridyl), $R^{12}$ is a hydrogen atom or alkyl (when p is a nitrogen atom, then $R^{12}$ is absent), and $R^{13}$ and $R^{14}$ are both hydrogen atoms, or when one of them is a hydrogen atom, then the other is cyano, alkoxy or halogen, (vi) in the formula (VII), one of r and s is a nitrogen atom and the other is a carbon atom, $R^{15}$ is a hydrogen atom, alkyl or phenyl (when r is a nitrogen atom, then $R^{15}$ is absent), $R^{16}$ is a hydrogen atom or alkyl (when s is a nitrogen atom, then $R^{16}$ is absent), and $R^{17}$ is a hydrogen atom, haloalkyl or cyano, (vii) in the formula (VIII), r' and s' may be the same or different and each is a carbon atom or a nitrogen atom, wherein at least one of them is a nitrogen atom (same as "1-2 of r' and s' is(are) nitrogen atom(s) and the rest is(are) carbon atom(s)"), $R^{15a}$ is a hydrogen atom, alkyl or phenyl (when r' is a nitrogen atom, then $R^{15a}$ is absent), $R^{16a}$ is a hydrogen atom or alkyl (when r' and s' are both nitrogen atoms, then $R^{16}$, is a hydrogen atom), and $R^{17a}$ is a hydrogen atom, haloalkyl or cyano, (viii) in the formula (IX), t is a sulfur atom or an oxygen atom, u is a carbon atom or a nitrogen atom, and $R^{18}$ and $R^{19}$ are both hydrogen atoms, or one of them is a hydrogen atom and the other is cyano, alkoxy or halogen, wherein (viii-1) when u is a carbon atom, then one of $R^{18}$ and $R^{19}$ is cyano, alkoxy or halogen (same as "$R^{18}$ and $R^{19}$ are not hydrogen atoms at the same time"), (viii-2) when t is a sulfur atom, then A in the formula (I-b) is a carbon atom, $R^{19}$ is a hydrogen atom and $R^{18}$ is methoxy or cyano, (viii-3) A in the formula (I-b) is a nitrogen atom, t is an oxygen atom, $R^{19}$ is a hydrogen atom, and when u is a carbon atom, then $R^{18}$ is alkoxy or halogen, and (viii-4) A in the formula (I-b) is a carbon atom, $R^{19}$ is a hydrogen atom, u is a carbon atom, and when t is an oxygen atom, $R^{18}$ is halogen, (ix) in the formula (X), v, w, x and y may be the same or different and each is a carbon atom or a nitrogen atom, wherein at least two are carbon atoms (same as "0-2 of v, w, x and y is(are) nitrogen atom(s) and the rest is(are) carbon atom(s)"), $R^{20}$, $R^{21}$, $R^{22}$, $R^{23}$, $R^{24}$, $R^{25}$ and $R^{26}$ may be the same or different and 1 to 3 is(are) haloalkyl, methoxy, ethoxy, isopropoxy, trifluoromethoxy, 2,2,2-trifluoroethoxy, hydroxy, cyano or halogen, and the rest is(are) hydrogen atom(s) (when V is a nitrogen atom, then $R^{20}$ is absent, when w is a nitrogen atom, then $R^{22}$ is absent, when x is a nitrogen atom, then $R^{23}$ is absent, when y is a nitrogen atom, then $R^{25}$ is absent), wherein (ix-1) when v is a nitrogen atom and w, x and y are all carbon atoms, then $R^{22}$ is haloalkyl, (ix-2) when v and w are both nitrogen atoms and x and y are both carbon atoms, then $R^{21}$ is cyano, and (ix-3) when w is a nitrogen atom and v, x and y are all carbon atoms, then (1) $R^{21}$ is a hydrogen atom and $R^{20}$ is cyano, (2) $R^{21}$ is haloalkyl and $R^{23}$ is hydroxy, ethoxy, isopropoxy, trifluoromethoxy or 2,2,2-trifluoroethoxy, (3) $R^{21}$ is haloalkyl and $R^{23}$ and $R^{25}$ are both methoxy, (4) $R^{21}$ is haloalkyl and $R^{24}$ is hydroxy, chloro or trifluoromethyl, (5) $R^{21}$ is haloalkyl and $R^{25}$ is hydroxy or trifluoromethoxy, (6) $R^{21}$ is haloalkyl and $R^{26}$ is methoxy, or (7) $R^{21}$ is cyano and $R^{23}$ is methoxy, and (x) in the formula (XI), $R^{27}$ and $R^{28}$ may be the same or different and each is haloalkyl or alkoxy;

Y is methylene, hydroxymethylene, a sulfur atom, sulfinyl or sulfonyl; and

Z is a hydrogen atom or cyano;

wherein when X is a substituent represented by the formula (I-a), then Z is a hydrogen atom, or a pharmaceutically acceptable salt thereof.

[2] The thiazolidine derivative of the above-mentioned [1], wherein Y' in the formula (I-a) is represented by —$NR^1R^2$ [$R^1$ is aryl optionally having substituent(s) or heteroaryl optionally having substituent(s), $R^2$ is a hydrogen atom, alkyl optionally having substituent(s), aryl optionally having substituent(s), arylalkyl optionally having substituent(s), heteroaryl optionally having substituent(s) or heteroarylalkyl optionally having substituent(s), or they may be bonded to each other to form a heterocycle optionally having 1 or 2 nitrogen atom(s) or oxygen atom(s) and optionally having substituent(s), where this heterocycle is optionally substituted or condensed with an aromatic ring optionally-having substituent(s)], or a pharmaceutically acceptable salt thereof.

[3] The thiazolidine derivative of the above-mentioned [1] or [2], wherein, in the formula (I), X is a substituent represented by the formula (I-a) and Z is a hydrogen atom, or a pharmaceutically acceptable salt thereof.

[4] The thiazolidine derivative of the above-mentioned [1], wherein X in the formula (I) is a substituent represented by the formula (I-b), or a pharmaceutically acceptable salt thereof.

[5] The thiazolidine derivative of the above-mentioned [3], wherein Y' in the formula (I-a) is a substituent selected from the following formulas:

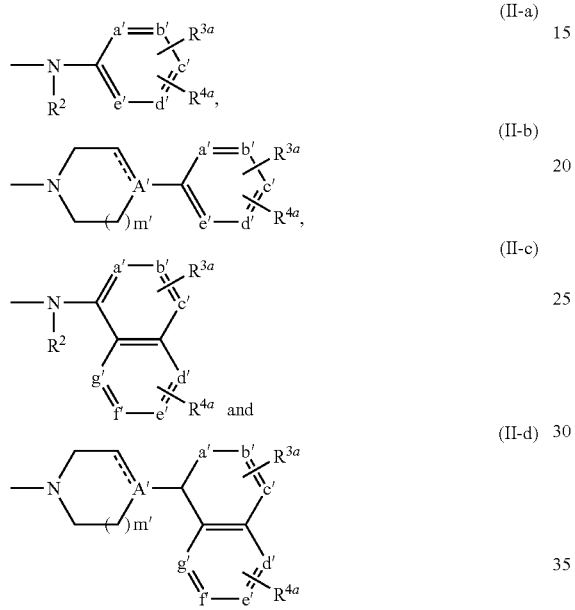

wherein
----- is a single bond or a double bond,
$R^2$ is as defined in claim 1,
$R^{3a}$ and $R^{4a}$ are the same or different and each is independently hydrogen atom, alkyl optionally having substituent(s), aryl optionally having substituent(s), arylalkyl optionally having substituent(s), heteroaryl optionally having substituent(s), heteroarylalkyl optionally having substituent(s), halogen, haloalkyl, cyano, nitro, —$NR^{5a}R^{6a}$, —$NHSO_2R^{7a}$, —$OR^{8b}$, —$COOR^{9a}$, —$CONHSO_2R^{10a}$, —$SO_2OR^{11a}$, —$SO_2R^{12a}$ or —$CONR^{13a}R^{14a}$ wherein $R^{5a}$, $R^{6a}$, $R^{7a}$, $R^{8b}$, $R^{9a}$, $R^{10a}$, $R^{11a}$, $R^{12a}$, $R^{13a}$ and $R^{14a}$ are the same or different and each is independently a hydrogen atom, alkyl optionally having substituent(s), cycloalkyl optionally having substituent(s), cycloalkylalkyl optionally having substituent(s), aryl optionally having substituent(s), arylalkyl optionally having substituent(s), heteroaryl optionally having substituent(s), heteroarylalkyl optionally having substituent(s) or haloalkyl, $R^{5a}$ and $R^{6a}$, and $R^{13a}$ and $R^{14a}$ may be bonded to each other to form a heterocycle having carbon and at least one nitrogen, optionally having other heteroatom(s) and optionally having substituent(s), where this heterocycle is optionally substituted or condensed with an aromatic ring optionally having substituent(s),
a', b', c', d', e', f' and g' are all carbon atoms, or any one or two thereof is(are) nitrogen atom(s), and the rest is(are) carbon atom(s),
m' is 0, 1, 2 or 3, and
A' is a carbon atom or a nitrogen atom,
wherein i) when A' is a carbon atom, then A' may be substituted by a hydroxyl group, carboxy or alkoxycarbonyl, and ii) when A' is a nitrogen atom, then ----- is a single bond,
or a pharmaceutically acceptable salt thereof.

[6] The thiazolidine derivative of the above-mentioned [5], wherein $R^{3a}$ and $R^{4a}$ of the formulas (II-a), (II-b), (II-c) and (II-d) may be the same or different and each is independently a hydrogen atom, alkyl optionally having substituent(s), aryl optionally having substituent(s), arylalkyl optionally having substituent(s), heteroaryl optionally having substituent(s), heteroarylalkyl optionally having substituent(s), halogen, haloalkyl, cyano, nitro, —$NR^{5a}R^{6a}$, —$NHSO_2R^{7a}$, —$OR^{8b}$, —$COOR^{9a}$, —$CONHSO_2R^{10a}$, —$SO_2OR^{11a}$, —$SO_2R^{12a}$ or —$CONR^{13a}R^{14a}$ wherein $R^{5a}$, $R^{6a}$, $R^{7a}$, $R^{8b}$, $R^{9a}$, $R^{10a}$, $R^{11a}$, $R^{12a}$, $R^{13a}$ and $R^{14a}$ are the same or different and each is independently hydrogen atom, alkyl optionally having substituent(s), cycloalkyl optionally having substituent(s), cycloalkylalkyl optionally having substituent(s), aryl optionally having substituent(s), arylalkyl optionally having substituent(s), heteroaryl optionally having substituent(s), heteroarylalkyl optionally having substituent(s) or haloalkyl, and $R^{5a}$ and $R^{6a}$, and $R^{13a}$ and $R^{14a}$ may be bonded to each other to form a heterocycle optionally having 1 or 2 nitrogen atom(s) or oxygen atom(s) and optionally having substituent(s), where this heterocycle is optionally substituted or condensed with an aromatic ring optionally having substituent(s), or a pharmaceutically acceptable salt thereof.

[7] The thiazolidine derivative of the above-mentioned [3], wherein Y is a sulfur atom and X' is a hydrogen atom, or a pharmaceutically acceptable salt thereof.

[8] The thiazolidine derivative of the above-mentioned [3], wherein Y is a sulfur atom, X' is a hydrogen atom and Y' is phenylamino optionally having substituent(s), 2-pyridylamino optionally having substituent(s) or 4-(1-isoquinolyl)-1-piperazinyl optionally having substituent(s), or a pharmaceutically acceptable salt thereof.

[9] A pharmaceutical composition comprising the thiazolidine derivative of any of the above-mentioned [1]-[8] or a pharmaceutically acceptable salt thereof, and a pharmacologically acceptable carrier.

[10] A DPP-IV inhibitor comprising the thiazolidine derivative of any of the above-mentioned [1]-[8] or a pharmaceutically acceptable salt thereof.

[11] A therapeutic agent of a disease, in which DPP-IV is involved, which comprises the thiazolidine derivative of any of the above-mentioned [1]-[8] or a pharmaceutically acceptable salt thereof as an active ingredient.

[12] The therapeutic agent of the above-mentioned [11], wherein the disease, in which DPP-IV is involved, is diabetes or obesity.

Each symbol used in the present specification is explained in the following.

The alkyl represented by X', $R^{1a}$, $R^2$, $R^{2a}$, $R^3$, $R^{3a}$, $R^4$, $R^{4a}$, $R^{5a}$, $R^6$, $R^{6a}$, $R^{7a}$, $R^{8b}$, $R^{9a}$, $R^{10a}$, $R^{11a}$, $R^{12}$, $R^{12a}$, $R^{13a}$, $R^{14a}$, $R^{15}$, $R^{16}$, $R^{15a}$ or $R^{16a}$ preferably means a linear or branched chain alkyl having 1 to 8 carbon atom(s), such as methyl, ethyl, propyl, isopropyl, butyl, isobutyl, tert-butyl, pentyl, hexyl, octyl and the like. Of these, methyl is preferable.

The alkyl that may substitute a group represented by $R^{1a}$ (when $R^{1a}$ is alkyl, it does not become a substituent) is exemplified by those similar to the ones mentioned above.

Cycloalkyl preferably has 3 to 7 carbon atoms and is exemplified by cyclopropyl, cyclopentyl, cyclohexyl, cycloheptyl and the like. Of these, cyclohexyl is preferable.

Cycloalkylalkyl is that wherein the cycloalkyl moiety is as mentioned above and the alkyl moiety is preferably a linear or branched chain cycloalkylalkyl having 1 to 3 carbon atom(s), such as cyclopropylmethyl, 2-cyclobutylethyl, 3-cyclopentylpropyl, cyclohexylmethyl, 2-cyclohexylethyl, cycloheptylmethyl and the like. Of these, cyclohexylmethyl is preferable.

Aryl is preferably that having 6 to 14 carbon atoms, which is preferably phenyl, naphthyl, an ortho-fused bicyclic group having 8 to 10 ring atoms, at least one ring being an aromatic ring (e.g., indenyl group) and the like. Of these, phenyl is preferable.

With regard to arylalkyl, the aryl moiety is as mentioned above and the alkyl moiety may be linear or branched chain and preferably has 1 to 3 carbon atom(s), which is exemplified by benzyl, benzhydryl, phenethyl, 3-phenyipropyl, 1-naphthylmethyl, 2-(1-naphthyl) ethyl, 2-(2-naphthyl)ethyl, 3-(2-naphthyl)propyl and the like. Of these, benzyl is preferable.

As heteroaryl, for example, a 5- or 6-membered ring group having carbon and 1-4 heteroatom(s) (oxygen, sulfur or nitrogen), an ortho-fused bicyclic heteroaryl having 8-10 ring atoms derived therefrom, particularly a benz derivative and one derived by fusing propenylene, trimethylene or tetramethylene group with the same, and stable N-oxide thereof and the like can be mentioned. For example, pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,4-oxadiazolyl, 1,2,4-thiadiazolyl, pyridyl (2-, 3-, 4-pyridyl), pyrazinyl, pyrimidinyl, pyridazinyl, 1,2,4-triazinyl, 1,2,3-triazinyl, 1,3,5-triazinyl, benzoxazolyl, benzisoxazolyl, benzothiazolyl, benzisothiazolyl, benzimidazolyl, oxazolopyridyl, imidazopyridazinyl, thianaphthenyl, isothianaphthenyl, benzofuranyl, isobenzofuranyl, benzothienyl, chromenyl, isoindolyl, indolyl, indolinyl, indazolyl, isoquinolyl, quinolyl, phthalazinyl, quinoxalinyl, quinazolinyl, cinnolinyl, 2,1,3-benzoxadiazolyl, benzoxazinyl and the like can be mentioned. Of these, pyridyl and pyrimidinyl are preferable.

With regard to heteroarylalkyl, the heteroaryl moiety is as mentioned above and the alkyl moiety may be preferably linear or branched chain and preferably has 1 to 3 carbon atom(s). Examples thereof include 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyridyl) ethyl, 3-(2-pyrrolyl)propyl, 4-imidazolylmethyl and the like. Of these, 2-pyridylmethyl is preferable.

The heterocycle contains carbon and at least one nitrogen, may have other heteroatom(s) (oxygen or sulfur), may preferably have 1-2 nitrogen atom(s) or oxygen atom(s), and is saturated or unsaturated. It includes not only monocycle but also spiro ring, and is preferably a 4- to 7-membered monocycle ring group or a 10- or 11-membered ring group as a spiro ring. As the heterocycle, for example, azetidinyl, pyrrolidinyl, piperidino, piperazinyl, morpholino, 1,4-diazepanyl, 1,2,5,6-tetrahydropyridyl, thiomorpholino, oxothiomorpholino, dioxothiomorpholino, 3-azapyrro[5,5]undecyl, 1,3,8-triazaspiro[4,5]decyl and the like can be mentioned. Of these, piperidino and piperazinyl are preferable.

Moreover, with regard to the above-mentioned heterocycle, the aromatic ring optionally having substituents may be substituted or condensed. The aromatic ring of the aromatic ring optionally having substituents is exemplified by benzene ring, pyridine ring and the like, with preference given to benzene ring. The aromatic ring may have one or more of the following substituents, and the substituent is preferably cyano or trifluoromethyl. Concrete examples of the condensed ring include indolinyl, isoindolinyl, 1,2,3,4-tetrahydroquinolyl, 1,2,3,4-tetrahydroisoquinolyl, phthalimide, indolyl and the like. Of these, indolinyl and 1,2,3,4-tetrahydroquinolyl are preferable.

The alkoxy represented by $R^{13}$, $R^{14}$, $R^{18}$, $R^{19}$, $R^{27}$ and $R^{28}$ preferably has 1 to 8 carbon atom(s) and may be linear or branched chain. Examples thereof include methoxy, ethoxy, propoxy, isopropoxy, butoxy, pentyloxy, hexyloxy, octyloxy and the like. Of these, methoxy and isopropoxy are preferable.

When A and A' are carbon atoms, alkoxycarbonyl that may substitute the carbon atom is exemplified by alkoxycarbonyl herein the alkoxy moiety is similar to the one mentioned above.

The alkoxy that may substitute a group represented by $R^{1a}$ is exemplified by those similar to the above-mentioned ones.

The halogen represented by $R^{3a}$, $R^{4a}$, $R^{13}$, $R^{14}$, $R^{18}$, $R^{19}$, $R^{20}$, $R^{21}$, $R^{22}$, $R^{23}$, $R^{24}$, $R^{25}$ or $R^{26}$ is exemplified by chlorine, bromine, fluorine and iodine. Of these, chlorine and fluorine are preferable.

The halogen that may substitute a group represented by $R^{1a}$ is exemplified by those similar to the above-mentioned ones.

The haloalkyl represented by $R^{2a}$, $R^{3a}$, $R^{4a}$, $R^{5a}$, $R^{6a}$, $R^{7a}$, $R^{8b}$, $R^9$, $R^{9a}$, $R^{10a}$, $R^{11a}$, $R^{12a}$, $R^{13a}$, $R^{14a}$, $R^{17}$, $R^{17a}$, $R^{20}$, $R^{21}$, $R^{22}$, $R^{23}$, $R^{24}$, $R^{25}$, $R^{26}$, $R^{27}$ or $R^{28}$ is alkyl substituted by one or more halogen(s), wherein halogen and alkyl are as defined above. Examples thereof include trifluoromethyl, 2,2,2-trifluoroethyl, pentafluoroethyl and the like. Of these, trifluoromethyl and 2,2,2-trifluoroethyl are preferable.

Of the above-mentioned substituents, alkyl, cycloalkyl, cycloalkylalkyl, aryl, arylalkyl, heteroaryl, heteroarylalkyl and heterocycle represented by X', $R^2$, $R^{3a}$, $R^{4a}$, $R^{5a}$, $R^{6a}$, $R^{7a}$, $R^{8b}$, $R^{9a}$, $R^{10a}$, $R^{11a}$, $R^{12a}$, $R^{13a}$ and $R^{14a}$ may be each substituted by one or more substituent(s) shown in the following.

As these substituents, for example, halogen (halogen is excluded from the substituents of alkyl for $R^{3a}$, $R^{4a}$, $R^{5a}$, $R^{6a}$, $R^{7a}$, $R^{8b}$, $R^{9a}$, $R^{10a}$, $R^{11a}$, $R^{12a}$, $R^{13a}$ or $R^{14a}$), a hydroxyl group, nitro, cyano, trifluoromethyl, alkyl (except alkyl as a substituent for the above-mentioned alkyl), alkoxy, alkylthio, formyl, acyloxy, oxo, phenyl, 2-pyridyl, 3-pyridyl, 4-pyridyl (except phenyl, 2-, 3-, 4-pyridyl as a substituent for alkyl), 4-piperidinyl, 2-morpholinoethyl, 3-picolyl, arylalkyl, —COOR$_a$, —CH$_2$COOR$_a$, —OCH$_2$COOR$_a$, —CON$_b$R$_c$, —CH$_2$CQ'NR$_b$R$_c$C (Q' is =O or =S), —OCH$_2$CONR$_b$R$_c$, —COO(CH$_2$)$_2$NR$_e$R$_f$, —SO$_2$T$_1$, —CONR$^d$SO$_2$T$_1$, —NR$_e$R$_f$, —NR$_g$CHO, —NR$_g$COT$_2$, —NR$_g$COOT$_2$, —NR$_g$CONR$_i$R$_j$, —NR$_k$SO$_2$T$_3$, —SO$_2$NR$_l$R$_m$, —SO$_2$NR$_n$COT$_4$, methylenedioxy, ethyleneoxy and the like can be mentioned, with preference given to halogen, nitro, cyano, trifluoromethyl, —SO$_2$T$_1$ and the like.

These substituents may further have substituent(s). As phenyl, 2-pyridyl and 4-piperidinyl having substituent(s), such as 4-cyanophenyl, 4-chlorophenyl, 4-methoxyphenyl, 5-cyano-2-pyridyl, 1-ethoxycarbonyl-4-piperidinyl and the like can be mentioned.

Here, of the above-mentioned substituents, halogen, alkyl and arylalkyl are exemplified by those mentioned above.

The alkoxy preferably has 1 to 8 carbon atom(s) and may be linear or branched chain. Examples thereof include methoxy, ethoxy, propoxy, butoxy, pentyloxy, hexyloxy, octyloxy and the like. The alkylthio preferably has 1 to 8 carbon atom(s) and may be linear or branched chain. Examples thereof include methylthio, ethylthio, propylthio, butylthio, pentylthio, hexylthio, octylthio and the like. The acyloxy preferably has 1 to 8 carbon atom(s) and may be linear or branched chain. Examples thereof include formyloxy, acetyloxy, propionyloxy, butyryloxy, valeryloxy, pivaloyloxy, hexanoyloxy, benzoyloxy and the like.

R$_a$-R$_n$ denotes hydrogen, alkyl (as mentioned above) or arylalkyl (as mentioned above). R$_b$ and R$_c$, R$_e$ and R$_f$, R$_i$ and R$_j$, and R$_l$ and R$_m$ of —NR$_b$R$_c$, —NR$_e$R$_f$, —NR$_i$R$_j$ and —NR$_l$ $R_m$ may be bonded to each other to form a heterocycle having carbon and at least one nitrogen and optionally having other heteroatom(s) (oxygen or sulfur), preferably a heterocycle having 1 or 2 nitrogen atom(s) or oxygen atom(s), where this heterocycle is optionally condensed with an aromatic ring optionally having substituent(s) (as mentioned above, and may be substituted by the substituents recited as the substituents for the aforementioned heterocycle), and —$NR_eR_f$ can also show heteroaryl having =O (e.g., 2-pyrrolidinon-1-yl, succinimide, oxazolidin-2-on-3-yl, 2-benzoxazolinon-3-yl, phthalimide, cis-hexahydrophthalimide etc.). $T_1$-$T_4$ shows a hydrogen atom, alkyl, cycloalkyl, cycloalkylalkyl, aryl, arylalkyl, heteroaryl, heteroarylalkyl or haloalkyl, which may be substituted by the substituents recited as the substituents for the aforementioned alkyl, cycloalkyl, cycloalkylalkyl, aryl and arylalkyl.

As the pyridyl represented by $R^{1a}$, $R^3$, $R^4$, $R^5$, $R^7$, $R^8$ and $R^{11}$, 1-pyridyl, 2-pyridyl, 3-pyridyl and 4-pyridyl can be mentioned.

As the pyrimidinyl represented by $R^{1a}$, 1-pyrimidinyl, 2-pyrimidinyl, 4-pyrimidinyl and 5-pyrimidinyl can be mentioned.

As the imidazolyl represented by $R^{1a}$, 1-imidazolyl, 2-imidazolyl and 4-imidazolyl can be mentioned.

As the oxazolyl represented by $R^{1a}$, 2-oxazolyl, 4-oxazolyl and 5-oxazolyl can be mentioned.

In the formula (II), "when c and d are both nitrogen atoms, a and b are both carbon atoms, $R^{1a}$ is phenyl and $R^{2a}$ is alkyl, then $R^{1a}$ has one or more substituents mentioned above" is the same as "when c and d are both nitrogen atoms, a and b are both carbon atoms, and $R^{2a}$ is alkyl, then $R^{1a}$ is not unsubstituted phenyl".

In the formula (II), "when all of a, b, c and d are nitrogen atoms and $R^{1a}$ is phenyl, then (1) A of the formula (I-b) is a carbon atom and $R^{1a}$ does not have the above-mentioned substituent, or (2) $R^{1a}$ is substituted by one or more from alkyl and halogen" is the same as "when all of a, b, c and d are nitrogen atoms, then (1) A of the formula (I-b) is a carbon atom and $R^{1a}$ is not phenyl having substituent(s), or (2) $R^{1a}$ is not phenyl substituted by one or more from alkoxy and cyano and is not unsubstituted phenyl".

Of the compounds (1) of the present invention, a compound wherein X is a substituent represented by the formula (I-a) and Z is a hydrogen atom, Y' is preferably a substituent represented by the above-mentioned formula (II-a), (II-b), (II-c) or (II-d), more preferably phenylamino optionally having substituent(s), 2-pyridylamino optionally having substituent(s) or 4-(1-isoquinolyl)-1-piperazinyl optionally having substituent(s). Y is preferably a sulfur atom and X' is preferably a hydrogen atom.

In compound (I) wherein X is represented by the formula (I-b), compound (I) can exist in an optically active form or as a diastereomer mixture due to an asymmetric carbon bonded with the formula:

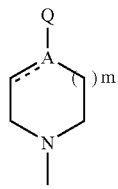

wherein each symbol is as defined above. This diastereomer mixture can be separated into each optically active form by a known method.

The compound (I) can show polymorphism, and can exist as more than one tautomers.

Therefore, the present invention encompasses any stereoisomer, optical isomer, polymorph, tautomer, any mixture thereof and the like mentioned above.

As the pharmaceutically acceptable salt of compound (I), inorganic acid addition salts (e.g., salts with hydrochloric acid, hydrobromic acid, hydriodic acid, sulfuric acid, nitric acid, phosphoric acid and the like), organic acid addition salts (e.g., salts with methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, methylsulfuric acid and the like), salts with amino acid (e.g., salts with glutamic acid, aspartic acid and the like) and the like can be mentioned.

The thiazolidine derivative of the present invention can be produced according to the following method. The production method of a compound wherein, in compounds (I) wherein X is represented by the formula (I-a) and Z is a hydrogen atom, $R^1$ is aryl or heteroaryl, is shown in Scheme 1.

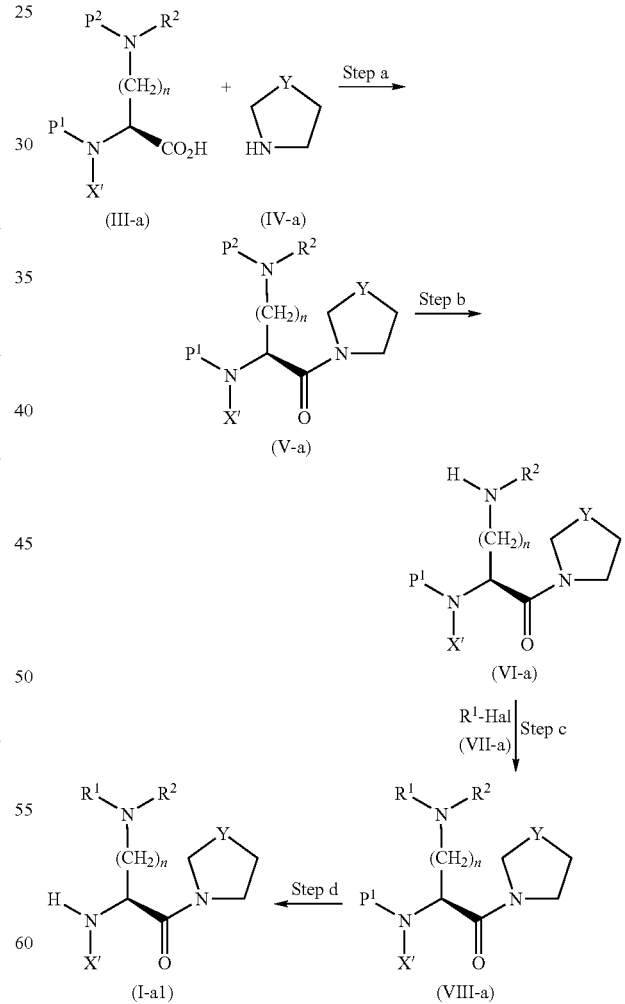

wherein $P^1$ and $P^2$ are amino acid-protecting groups (e.g., tert-butoxycarbonyl (Boc), benzyloxycarbonyl (Cbz), (9H-fluorein-9-yl)methyloxycarbonyl (Fmoc) etc.) or solid phase carriers (e.g., Wang resin via carbonyl group), Hal is halogen (preferably fluorine) and other symbols are as defined above.

Step a: Step for reacting compound (III-a) with compound (IV-a) to give amide compound (V-a).

As a condensation agent to activate carboxylic acid of compound (III-a), for example, dicyclohexylcarbodiimide (DCC), N-(3-dimethylaminopropyl)-N'-ethylcarbodiimide (EDC) or hydrochloride thereof, 2-ethoxy-1-ethoxycarbonyl-1,2-dihydroxyquinoline (EEDQ), carbodiimidazole (CDI), diethylphosphoryl cyamide, benzotriazol-1-yloxytripyrrolidinophosphonium hexafluorophosphate (PyBOP), diphenylphosphoryl azide (DPPA), isobutyl chloroformate, diethylacetyl chloride, trimethylacetyl chloride and the like can be mentioned, with preference given to EDC. These condensation agents are used alone, or in combination with an additive such as N-hydroxysuccinimide (HONSu), hydroxybenzotriazole (HOBT), 3-hydroxy-4-oxo-3,4-dihydro-1,2,3-benzotriazine (HOOBT), 4-dimethylaminopyridine (DMAP) and the like, preferably HOBT.

The amount of compound (IV-a) to be used is generally 90-300 mol %, preferably 100-150 mol %, relative to compound (III-a).

The amount of the condensation agent to be used is generally 100-300 mol %, preferably 100-200 mol %, relative to compound (III-a).

The amount of the additive to be used is generally 100-200 mol %, preferably 100-150 mol %, relative to compound (III-a).

This reaction is generally carried out in a solvent inert to the reaction, and the inert solvent to be used may be any as long as it is aprotic. Preferred are acetonitrile, tetrahydrofuran, dichloromethane, chloroform, N,N-dimethylformamide (DMF) and the like. This condensation is generally conducted at a temperature of −30° C. to 80° C., preferably −10° C. to 25° C.

Step b: Step for deprotecting compound (V-a) to give compound (VI-a).

In this reaction, when the protecting group $P^2$ is a Boc group, for example, deprotection can be conducted by a reaction in a solvent inert to the deprotection reaction such as acetonitrile, tetrahydrofuran, 1,4-dioxane, ethyl acetate, methanol, ethanol, dichloromethane, chloroform and the like, using an acid such as hydrogen chloride, trifluoroacetic acid and the like, generally at −30° C. to 60° C. for 10 min-24 hr.

The amount of the acid to be used is generally 100-3000 mol %, preferably 100-1000 mol %, relative to compound (V-a).

When the protecting group $P^2$ is a Cbz group, for example, deprotection can be conducted by subjecting the compound to catalytic hydrogen reduction in a solvent inert to the deprotection reaction such as methanol, ethanol, tetrahydrofuran, 1,4-dioxane, ethyl acetate and the like, in the presence of a catalyst such as palladium and the like, reacting the compound with hydrobromic acid-acetic acid, or, for example, reacting the compound with trifluoroacetic acid or trifluoromethanesulfonic acid, preferably trifluoromethanesulfonic acid in the presence of thioanisole or anisole, in, where necessary, a solvent inert to the deprotection reaction such as dichloromethane, chloroform and the like.

The amount of thioanisole or anisole to be used is generally 100-2000 mol %, preferably 100-1000 mol %, relative to compound (V-a).

The amount of trifluoroacetic acid or trifluoromethanesulfonic acid to be used is generally 100-20000 mol %, preferably 100-10000 mol %, relative to compound (V-a).

When the protecting group $P^2$ is a Fmoc group, for example, deprotection can be conducted by reacting in, where necessary, a solvent inert to the deprotection such as N,N-dimethylformamide, tetrahydrofuran and the like, using a base such as ammonia, piperidine, morpholine and the like, preferably piperidine, generally at −30° C. to 60° C. for 5 min-1 hr.

The amount of the base to be used is generally 100-2000 mol %, preferably 100-500 mol %, relative to compound (V-a).

Step c: Step for reacting compound (VI-a) with compound (VII-a) to give compound (VIII-a).

The reaction is carried out in the presence of a base such as triethylamine, diisopropylethylamine and the like, preferably diisopropylethylamine, in a solvent inert to the reaction such as N-methyl-2-pyrrolidone, N,N-dimethylformamide, tetrahydrofuran and the like at 0° C. to a temperature near the boiling point of the solvent, preferably 0° C. to 80° C.

The amount of compound (VII-a) to be used is generally 100-500 mol %, preferably 100-200 mol %, relative to compound (VI-a).

The amount of the base to be used is generally 100-500 mol %, preferably 120-300 mol %, relative to compound (VI-a).

Step d: Step for deprotecting compound (VIII-a) to give compound (1-a1). In this case, the same reaction conditions as in Step b are employed.

When the solid phase carrier $P^1$ is Wang resin via carbonyl group, the solid phase carrier can be separated by, for example, reaction in, where necessary, a solvent inert to the reaction such as dichloromethane and the like, and, where necessary, adding an additive such as thioanisole, anisole, phenol, ethylenedithiol and the like and using trifluoroacetic acid as a solvent generally at a temperature near room temperature for 1-24 hr.

Of compounds (1) wherein X is represented by the formula (I-a) and Z is a hydrogen atom, a compound wherein substituent Y' is represented by the formula (II-b) or (II-d) can be produced according to a method shown in Scheme 2.

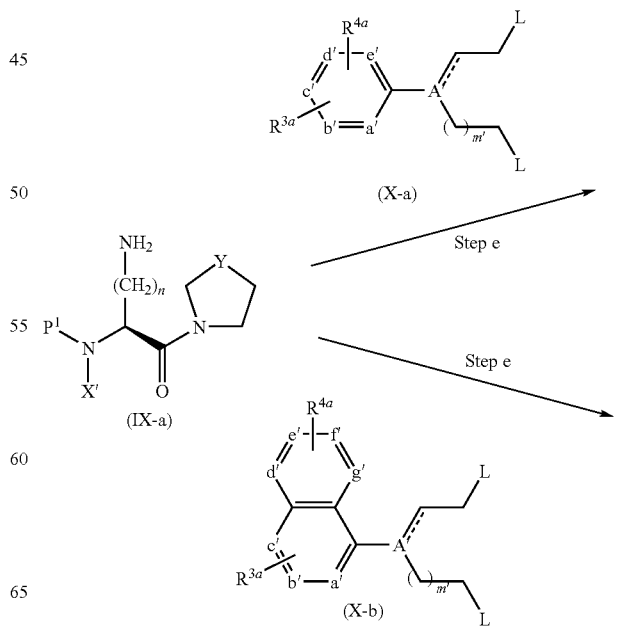

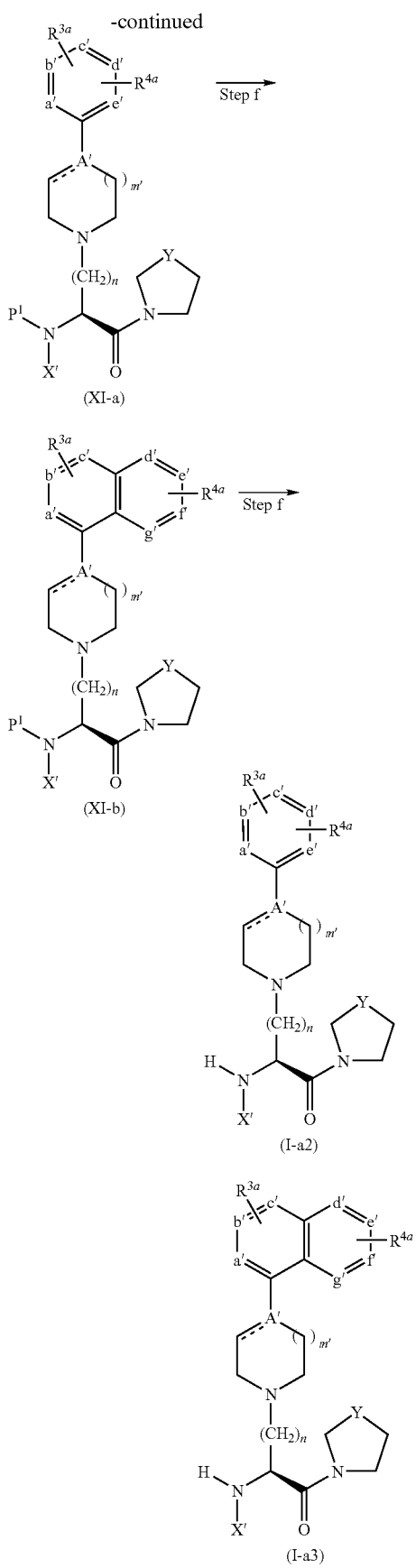

wherein L is a leaving group (e.g., halogen, tosylate (OTs), mesylate (OMs), triflate (OTf) and the like), and other symbols are as defined above.

Step e: Step for reacting compound (X-a) or compound (X-b) with compound (IX-a) to give compound (XI-a) or compound (XI-b).

The reaction is carried out in the presence of a base such as potassium carbonate, cesium carbonate, sodium carbonate, sodium hydrogencarbonate, triethylamine, diisopropylethylamine and the like, preferably potassium carbonate, in a solvent inert to the reaction such as N-methyl-2-pyrrolidone, N,N-dimethylformamide, tetrahydrofuran and the like, at 0° C.—a temperature near the boiling point of solvent, preferably 0° C. to 80° C.

The amount of compound (X-a) or compound (X-b) to be used is generally 100-500 mol %, preferably 100-200 mol %, relative to compound (IX-a).

The amount of the base to be used is generally 100-500 mol %, preferably 100-300 mol %, relative to compound (IX-a).

Step f: Step for deprotecting compound (XI-a) or (XI-b) to give compound (I-a2) or (I-a3). Conducted According to a Method Similar to that in Step b.

The compound (1) wherein X is represented by the formula (I-a) and Z is a hydrogen atom, can be also produced by the methods shown in Scheme 3 and Scheme 4.

Scheme 3

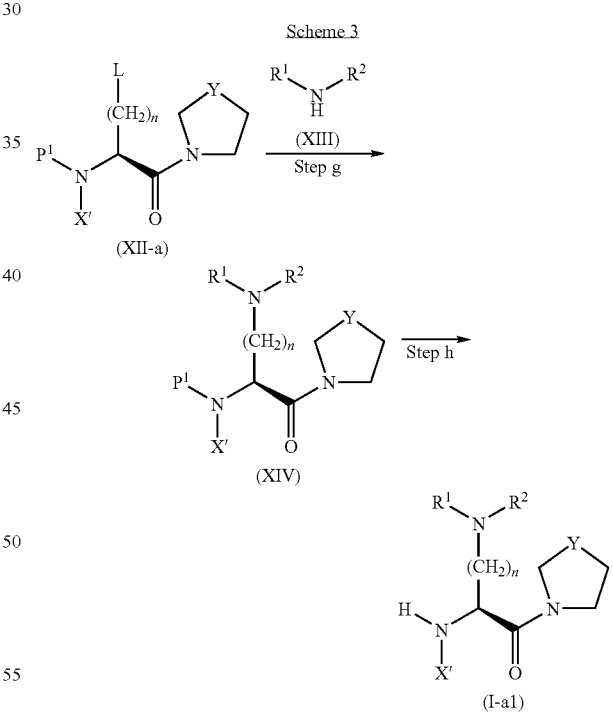

wherein each symbol is as defined above.

Step g: Step for reacting compound (XII-a) with compound (XIII) to give compound (XIV).

The reaction is carried out in the presence of a base such as potassium carbonate, cesium carbonate, sodium carbonate, sodium hydrogencarbonate, triethylamine, diisopropylethylamine and the like, preferably diisopropylethylamine, in a solvent inert to the reaction such as N-methyl-2-pyrrolidone, N,N-dimethylformamide, tetrahydrofuran and the like, at 0° C.—a temperature near the boiling point of solvent, preferably 0° C. to 80° C.

The amount of compound (XIII) to be used is generally 100-500 mol %, preferably 100-200 mol %, relative to compound (XII-a).

The amount of the base to be used is generally 100-500 mol %, preferably 100-300 mol %, relative to compound (XII-a).

Step h: Step for deprotection of compound (XIV) to give compound (I-a1). Conducted according to a method similar to that in Step b.

Scheme 4

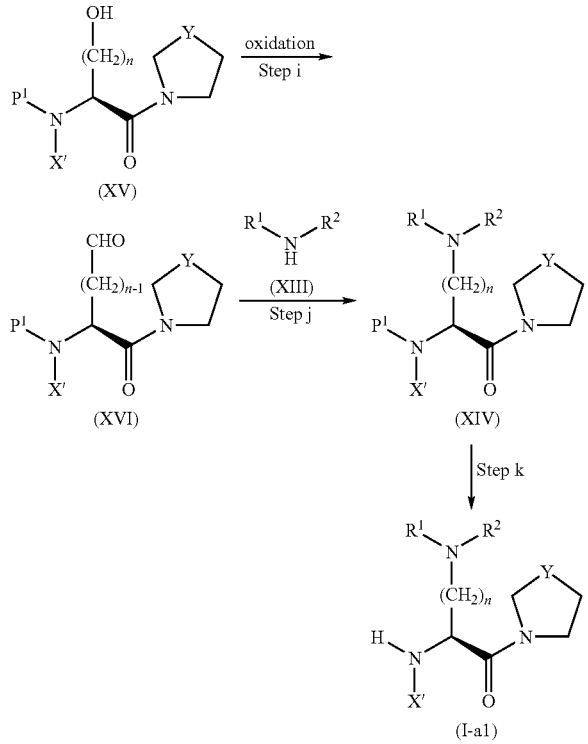

wherein each symbol is as defined above.

Step i: Step for oxidation of compound (XV) to give compound (XVI).

For this reaction, for example, a method using a pyridine sulfur trioxide complex and dimethyl sulfoxide at room temperature is preferable, but other useful methods include, for example, a method using alkaline potassium permanganate solution; a method using oxalyl chloride, dimethyl sulfoxide and tertiary amine; a method using acetic anhydride and dimethyl sulfoxide; a method using dichloroacetic acid as a catalyst, DCC or EDC and dimethyl sulfoxide; a method using a chromium (VI) oxide pyridine complex in dichloromethane; a method using a aqueous sodium hypochlorite solution in ethyl acetate or toluene with TEMPO free radical as a catalyst in the presence of sodium bromide and the like.

Step j: Step for reacting compound (XVI) with compound (XIII) and then reducing to give compound (XIV).

This reaction may be carried out in the presence of a reducing agent such as sodium borohydride, sodium cyanoborohydride, sodium triacetoxyborohydride and the like, preferably sodium triacetoxyborohydride, in a solvent inert to the reaction such as methanol, ethanol, dichloromethane, 1,2-dichloroethane, chloroform, tetrahydrofuran, acetonitrile, 1,4-dioxane and the like, using, where necessary, an acidic catalyst such as acetic acid, p-toluenesulfonic acid, a boron trifluoride diethyl ether complex and the like, preferably acetic acid, generally at 0° C. to 100° C. for 10 min-10 hr.

The amount of compound (XIII) to be used is generally 100-300 mol %, preferably 100-200 mol %, relative to compound (XVI).

The amount of the reducing agent to be used is generally 100-500 mol %, preferably 100-300 mol %, relative to compound (XVI).

Step k: Step for deprotecting compound (XIV) to give compound (I-a1). Conducted according to a method similar to that in Step b.

The starting material compound (XII-a) in Scheme 3 can be synthesized by, as shown in Scheme 5, condensing carboxylic acid compound represented by the formula (XVII) and compound (IV-a) according to the same method as in Step a, halogenating a hydroxyl form represented by the formula (XV), or sulfonylating the hydroxyl form using methanesulfonyl chloride, p-toluenesulfonyl chloride, trifluoromethanesulfonic anhydride and the like. In addition, a compound represented by the starting material compound (XII-a) wherein L is halogen can be also produced by reacting a compound represented by the formula (IX-a) with sodium nitrite or nitrite in the presence of the corresponding alkali metal halide salt.

The hydroxyl form represented by the formula (XV) can be produced by condensing the corresponding N-protected hydroxyamino acid (XVIII) and compound (IV-a) according to the same method as in Step a, or subjecting dipeptide compound (XIX) comprising N-protected aspartic acid, N-protected glutamic acid, 2-protected aminoadipic acid or 2-protected aminopimeric acid and compound (IV-a) to reduction reaction using lithium borohydride and the like.

Scheme 5

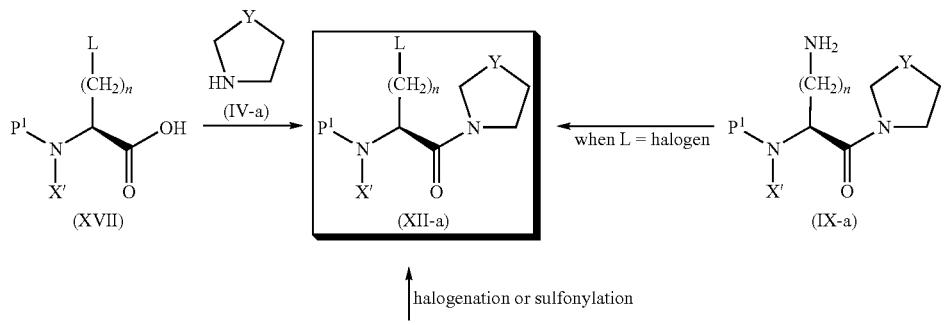

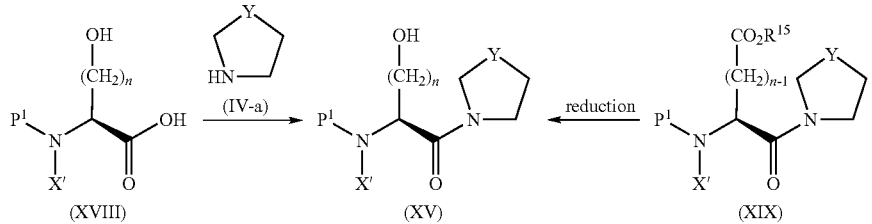
wherein R[15] is alkyl (as defined above) or arylalkyl (as defined above) and other symbols are as defined above.
The production method of compound (I) wherein X is represented by the formula (I-b) is shown in Scheme 6.
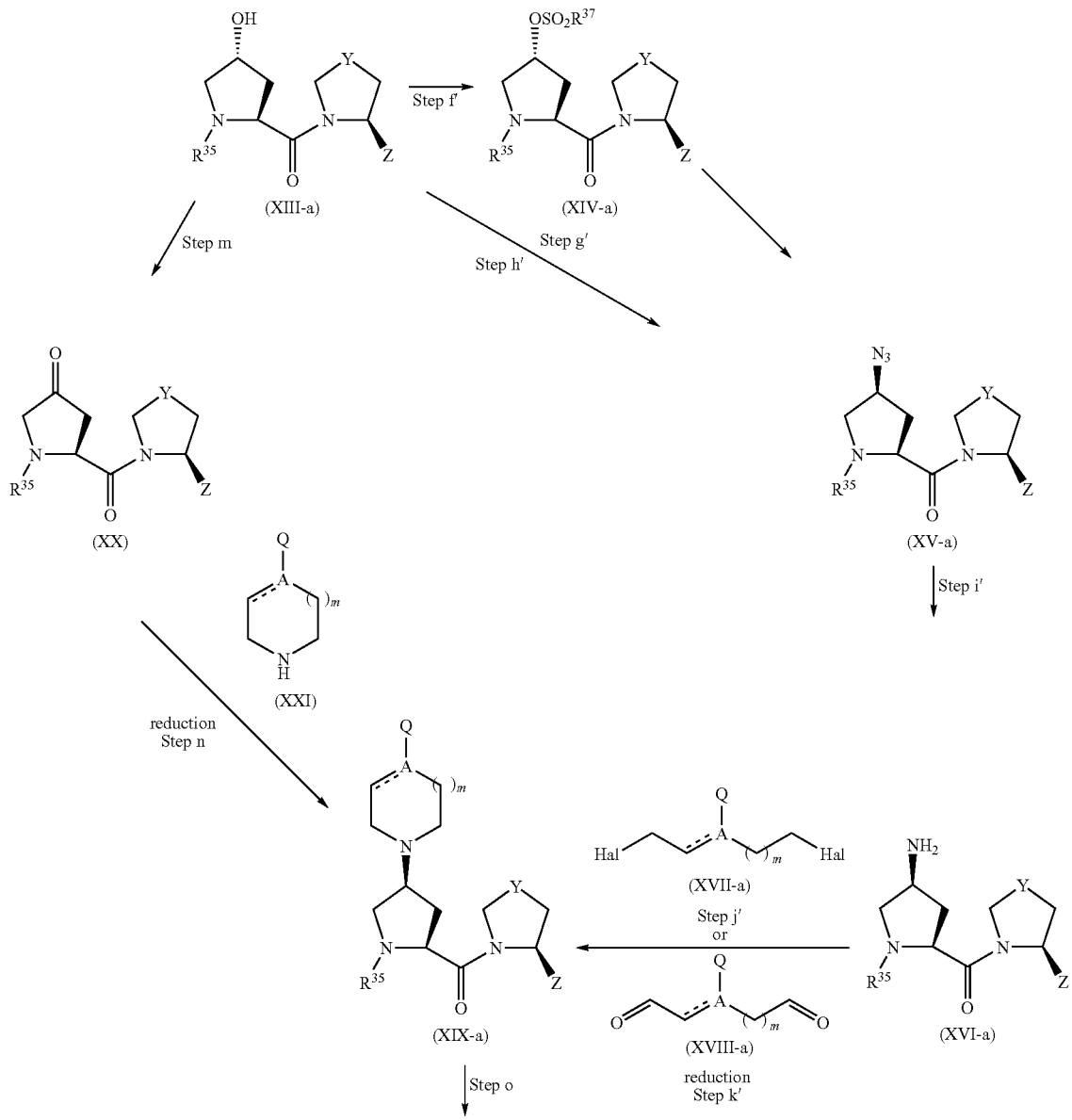

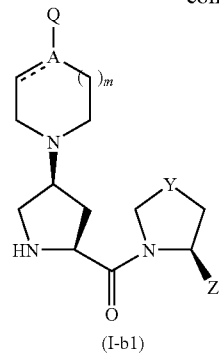

(I-b1)

wherein $R^{35}$ is an amino-protecting group (e.g., tert-butoxycarbonyl (Boc), benzyloxycarbonyl (Cbz)), —$OSO_2R^{37}$ is a leaving group (e.g., tosylate (OTs), mesylate (OMs), triflate (OTf)), Hal is halogen, and other symbols are as defined above.

Step f': Step for subjecting a hydroxyl group of compound (XIII-a) to sulfonylation to give compound (XIV-a).

This reaction is carried out in the presence of a base such as pyridine, triethylamine and the like, using sulfonyl chloride such as p-toluenesulfonyl chloride, methanesulfonyl chloride, trifluoromethanesulfonyl chloride and the like, preferably methanesulfonyl chloride, in a solvent inert to the reaction such as dichloromethane, 1,2-dichloroethane and the like at a temperature of generally −30° C. to 60° C. for 10 min-24 hr.

The amount of sulfonyl chloride to be used is generally 100-300 mol %, preferably 100-200 mol %, relative to compound (XIII-a)

Step g': Step for subjecting compound (XIV-a) to azidation to give compound (XV-a).

The reaction is carried out using a metal azide, such as sodium azide in a solvent such as N,N-dimethylformamide and the like at a temperature of generally 0° C. to 120° C. for 30 min to 24 hr.

The amount of metal azide to be used is generally 100-300 mol %, preferably 100-150 mol %, relative to compound (XIV-a).

Step h': Step for directly obtaining compound (XV-a) from compound (XIII-a).

The reaction is carried out in the presence of phosphines such as triphenylphosphine, tributylphosphine and the like and azodicarboxylic acid diester, using an azidating reagent such as hydrogen azide, DPPA, zinc azide bispyridine complex salt and the like, preferably DPPA, in a solvent inert to the reaction such as toluene, tetrahydrofuran and the like at a reaction temperature of generally −30° C. to 100° C.

The amount of phosphines to be used is generally 100-300 mol %, preferably 100-200 mol %, relative to compound (XIII-a).

The amount of azodicarboxylic acid diester to be used is generally 100-300 mol %, preferably 100-200 mol %, relative to compound (XIII-a).

The amount of the azidating reagent to be used is generally 100-300 mol %, preferably 100-200 mol %, relative to compound (XIII-a).

Step i': Step for reducing compound (XV-a) to give compound (XVI-a).

As this reaction, catalytic hydrogenation in the presence of palladium, platinum, nickel and the like, reduction with metal hydride, reduction using triphenylphosphine, thiol, sulfide, diborane, or a transition metal, and the like can be mentioned, with preference given to catalytic hydrogenation using palladium.

Step j': Step for reacting compound (XVI-a) with compound (XVII-a) to give compound (XIX-a).

The reaction is carried out in the presence of a base such as triethylamine, diisopropylethylamine and the like, preferably diisopropylethylamine, in a solvent inert to the reaction such as N-methyl-2-pyrrolidone, N,N-dimethylformamide, tetrahydrofuran and the like at 0° C. to a temperature near the boiling point of solvent, preferably 0° C. to 80° C.

The amount of compound (XVII-a) to be used is generally 100-500 mol %, preferably 100-200 mol %, relative to compound (XVI-a).

The amount of the base to be used is generally 200-1000 mol %, preferably 200-500 mol %, relative to compound (XVI-a).

Step k': Step for reacting compound (XVI-a) with compound (XVIII-a) and then Reducing to give compound (XIX-a).

This reaction may be carried out in the presence of a reducing agent such as sodium borohydride, sodium cyanoborohydride, sodium triacetoxyborohydride and the like, preferably sodium triacetoxyborohydride, in a solvent inert to the reaction such as methanol, ethanol, dichloromethane, chloroform, 1,2-dichloroethane, tetrahydrofuran, acetonitrile, 1,4-dioxane and the like, using, where necessary, an acidic catalyst, such as acetic acid, p-toluenesulfonic acid, boron trifluoride diethyl ether complex and the like at a temperature of generally 0° C. to 100° C. for 10 min-20 hr.

The amount of compound (XVIII-a) to be used is generally 100-300 mol %, preferably 100-200 mol %, relative to compound (XVI-a).

The amount of the reducing agent to be used is generally 200-1000 mol %, preferably 200-500 mol %, relative to compound (XVI-a).

Step m: Step for oxidation of compound (XIII-a) to give compound (XX).

For this reaction, for example, a method using a pyridine sulfur trioxide complex and dimethyl sulfoxide at room temperature is preferable, but other useful methods include, for example, a method using alkaline potassium permanganate solution; a method using oxalyl chloride, dimethyl sulfoxide and tertiary amine; a method using acetic anhydride and dimethyl sulfoxide; a method using dichloroacetic acid as a catalyst, DCC or EDC and dimethyl sulfoxide; a method using a chromium (IV) oxide pyridine complex in dichloromethane; a method using a aqueous sodium hypochlorite solution in ethyl acetate or toluene with TEMPO free radical as a catalyst in the presence of sodium bromide and the like.

Step n: Step for reacting compound (XX) with compound (XXI) and then reducing to give compound (XIX-a).

This reaction may be carried out in the presence of a reducing agent such as sodium borohydride, sodium cyanoborohydride, sodium triacetoxyborohydride and the like, preferably sodium triacetoxyborohydride, in a solvent inert to the reaction such as methanol, ethanol, dichloromethane, chloroform, 1,2-dichloroethane, tetrahydrofuran, acetonitrile, 1,4-dioxane and the like, using, where necessary, an acidic catalyst, such as acetic acid, p-toluenesulfonic acid, boron trifluoride diethyl ether complex and the like at a temperature of generally 0° C. to 100° C. for 10 min-20 hr.

The amount of compound (XXI) to be used is generally 100-300 mol %, preferably 100-200 mol. %, relative to compound (XX).

The amount of the reducing agent to be used is generally 100-500 mol %, preferably 100-300 mol %, relative to compound (XX).

The compound (XXI) can be synthesized according to a known method.

Step o: Step for deprotection of compound (XIX-a) to give compound (I-b1).

When the protecting group $R^{35}$ is a Boc group in this reaction, for example, deprotection can be conducted by reaction in a solvent such as acetonitrile, tetrahydrofuran, 1,4-dioxane, ethyl acetate, methanol, ethanol, dichloromethane, chloroform and the like, using an acid such as hydrogen chloride, trifluoroacetic acid and the like generally at −30° C. to 60° C. for 10 min-24 hr.

The amount of the acid to be used is generally 100-3000 mol %, preferably 100-1000 mol %, relative to compound (XIX-a).

When the protecting group $R^{35}$ is a Cbz group, for example, deprotection can be conducted by catalytic hydrogen reduction in a solvent inert to the deprotection such as methanol, ethanol, tetrahydrofuran, 1,4-dioxane, ethyl acetate and the like, in the presence of a catalyst such as palladium and the like, reaction with hydrobromic acid-acetic acid, or, for example, reaction with trifluoroacetic acid or trifluoromethanesulfonic acid, preferably trifluoromethanesulfonic acid in, where necessary, a solvent inert to the deprotection reaction such as dichloromethane, chloroform and the like, in the presence of thioanisole or anisole.

The amount of thioanisole or anisole to be used is generally 100-2000 mol %, preferably 100-1000 mol %, relative to compound (XIX-a).

The amount of trifluoroacetic acid or trifluoromethanesulfonic acid to be used is generally 100-20000 mol %, preferably 100-10000 mol %, relative to compound (XIX-a).

A different production method of compound (I) of the present invention, wherein X is represented by the formula (I-b) is shown in Scheme 7.

Scheme 7

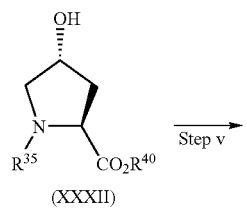

(XXXII)

Step v

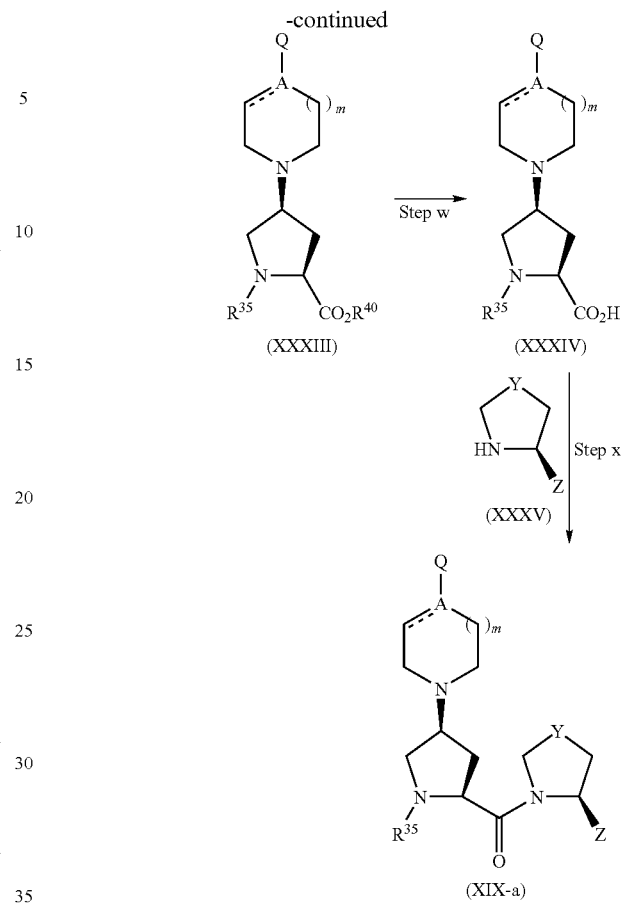

wherein $R^{40}$ is alkyl such as methyl, ethyl and the like, benzyl and the like and other symbols are as defined above.

Step v is the same as the method of conversion from compound (XIII-a) to compound (XIX-a) as shown in Scheme 6.

Step w: Step for deprotection of ester-protected carboxyl group of compound (XXXIII) to give compound (XXXIV).

For the reaction, conventional deprotection reaction can be used. Deprotection can be conducted by, for example, hydrolysis under alkaline conditions with sodium hydroxide, potassium hydroxide, sodium carbonate, potassium carbonate and the like, preferably sodium hydroxide, or when $R^{40}$ is benzyl, catalytic hydrogenation in the presence of platinum, palladium and the like, in a solvent inert to the reaction such as methanol, ethanol and the like.

Step x: Step for reacting compound (XXXV) with compound (XXXIV) to give compound (XIX-a).

For the reaction, the condensation agent shown in Step a, preferably EDC, can be used. The reaction is carried out using a condensation agent alone, or in combination with an additive shown in Step a, preferably HOBT, in a solvent inert to the reaction such as acetonitrile, tetrahydrofuran, dichloromethane, chloroform, N,N-dimethylformamide and the like generally at a temperature of −30° C. to 80° C., preferably −10° C. to 25° C.

The amount of compound (XXXV) to be used is generally 90-300 mol %, preferably 100-150 mol %, relative to compound (XXXIV).

The amount of the condensation agent to be used is generally 100-300 mol %, preferably 100-200 mol %, relative to compound (XXXIV).

The amount of the additive to be used is generally 100-200 mol %, preferably 100-150 mol %, relative to compound (XXXIV).

The production method of compound (1), wherein X is represented by the formula (I-b) and the asymmetric carbon, to which the formula:

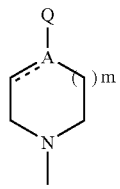

wherein each symbol is as defined above, is bonded, is in an S configuration, is shown in Scheme 6 using a compound represented by the formula (XIII-a) as a starting material and in Scheme 7 using a compound represented by the formula (XXXII) as a starting material.

In addition to the above, compound (I'-b1) wherein the asymmetric carbon, to which the formula:

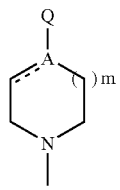

wherein each symbol is as defined above, is bonded, is represented by an R configuration can be also produced using compound (XIII'-a)

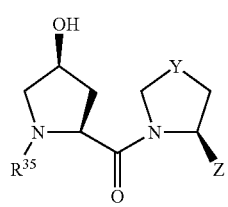

(XIII'-a)

wherein each symbol is as defined above, or compound (XXXII')

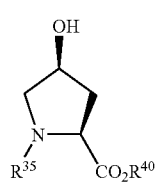

(XXXII')

wherein each symbol is as defined above, as a starting material according to a method similar to the above-mentioned method.

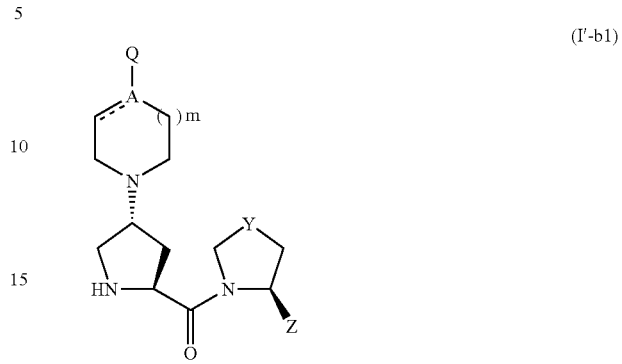

(I'-b1)

When Z in each formula is cyano, the production up to each intermediate is done with Z in the formula being a carbamoyl group, which is then dehydrated according to a known method, thereby to convert Z into a cyano group.

This reaction is carried out using diphosphorus pentaoxide, phosphorus oxychloride-imidazole, trifluoroacetic anhydride, p-toluenesulfonyl chloride-pyridine and the like as a dehydrating agent in an inert solvent such as dichloromethane, pyridine and the like.

The thiazolidine derivative of the formula (I) of the present invention thus produced can be obtained at any purity by appropriately applying known separation and purification means, such as concentration, extraction, chromatography, re-precipitation, recrystallization and the like.

Where necessary, the thiazolidine derivative of the formula (I) can be converted to an acid addition salt with an inorganic acid such as hydrochloric acid, hydrobromic acid, hydriodic acid, sulfuric acid, nitric acid, phosphoric acid and the like or an organic acid such as methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, methylsulfuric acid and the like. It can be also present as a solvate such as hydrate and the like.

The compound of the formula (I) and a pharmacologically acceptable salt thereof (pharmaceutically acceptable salt) of the present invention exhibit a superior DPP-IV inhibitory activity in mammals (e.g., human, dog, cat, rat etc.).

Since the compound (I) and a pharmacologically acceptable salt thereof (pharmaceutically acceptable salt) of the present invention exhibit a potent DPP-IV inhibitory activity as demonstrated in the experiment to be mentioned below, they are useful as DPP-IV inhibitors and useful for the prophylaxis or treatment of various diseases in which DPP-IV is involved and the like, including the prophylaxis or treatment of diseases in which GLP-1 is considered to be involved (e.g., diabetes, obesity etc.) and the like. A disease in which DPP-IV is involved is, for example, diabetes, obesity and the like.

In addition, the compound (I) of the present invention can be administered simultaneously with other therapeutic drugs for diabetes, therapeutic drugs for diabetic complications, anti-hyperlipidemia agents, hypotensive agents and the like to a single subject, or in a staggered manner to a single subject. When the compound of the present invention is used in combination with other agents, the ratio of addition can be appropriately determined according to the administration subject, age and body weight of the administration subject, condition, administration time, dosage form, administration method, combination and the like.

When compound (I) and a pharmacologically acceptable salt thereof (pharmaceutically acceptable salt) of the present invention are used as the aforementioned pharmaceutical agents, they can be administered orally or parenterally as they are or in the form of powder, granule, tablet, capsule, injection and the like after admixing with appropriate pharmacologically acceptable carrier, excipient, diluent and the like. The above-mentioned preparation contains an effective amount of compound (I) or a pharmacologically acceptable salt (pharmaceutically acceptable salt).

The dose of said compound (I) or a pharmacologically acceptable salt (pharmaceutically acceptable salt) varies depending on the administration route, target disease, condition, body weight and age of patient, and the compound to be used, and can be determined appropriately depending on the administration object. When orally administered to an adult, the dose is generally 0.01-1000 mg/kg body weight/day, preferably 0.05-500 mg/kg body weight/day, which is preferably administered in once to several times a day in divided doses.

EXAMPLES

The present invention is explained in detail in the following by referring to Reference Examples and Examples, which are not to be construed as limitative.

$^1$H-NMR was measured at 300 MHz unless particularly indicated. The chemical shifts of $^1$H-NMR was measured using tetramethylsilane (TMS) as the internal standard and expressed as relative delta (δ) value in parts per million (ppm). For the coupling constant, obvious multiplicity is shown using s (singlet), d (doublet), t (triplet), q (quartet), quint (quintet), m (multiplet), dd (doublet of doublets), td (triplet of doublets), brs (broad singlet) and the like in hertz (Hz). Thin layer chromatography was performed using silica gel manufactured by Merck and column chromatography was performed using silica gel manufactured by Fuji Silysia Chemical Ltd. Purification by HPLC was performed using Develosil Combi-RP. For drying organic solutions in extraction, anhydrous sodium sulfate or anhydrous magnesium sulfate was used unless particularly indicated.

Reference Example 1

Synthesis of 3-[(S)-6-amino-2-(benzyloxycarbonyl) aminohexanoyl]-1,3-thiazolidine (1) N-α-Benzyloxycarbonyl-N-ε-tert-butoxycarbonyl-L-lysine (19 g) was dissolved in dichloromethane (200 mL), and thiazolidine (3.91 mL), HOBT monohydrate (11.5 g) and EDC hydrochloride (14.4 g) were added successively. The mixture was stirred overnight. The reaction solution was concentrated under reduced pressure, and a 10% a aqueous citric acid solution was added. The mixture was extracted with ethyl acetate. The extract solution washed successively with a 10% a aqueous citric acid solution, a saturated a aqueous sodium hydrogen carbonate solution and saturated brine and dried. The solvent was evaporated under reduced pressure to give 3-[(S)-6-(tert-butoxycarbonyl)amino-2-(benzyloxycarbonyl)aminohexanoyl]-1,3-thiazolidine.

(2) Trifluoroacetic acid (100 mL) was added to the above-mentioned compound and the mixture was stirred for 3 hr. The reaction solution was concentrated under reduced pressure, and a saturated a aqueous sodium hydrogen carbonate solution was added. The mixture was extracted with ethyl acetate and the extract solution was dried and concentrated under reduced pressure to give the title compound (17 g).

MS (ESI) m/z: 352 [MH]$^+$

Reference Example 2

Synthesis of 3-{(S)-2-amino-6-[(9H-fluoren-9-yl) methyloxycarbonyl]aminohexanoyl}-1,3-thiazolidine (1) N-α-tert-Butoxycarbonyl-N-ε-(9H-fluoren-9-yl)methyloxycarbonyl-L-lysine (3.7 g) was dissolved in dichloromethane (200 mL), and thiazolidine (740 μL), HOBT monohydrate (1.8 g) and EDC hydrochloride (2.3 g) were added. The mixture was stirred for 1 hr. The reaction solution was concentrated under reduced pressure, and water was added to the residue. The mixture was extracted with ethyl acetate. The extract solution washed successively with a 10% a aqueous citric acid solution, a saturated a aqueous sodium hydrogen carbonate solution and saturated brine, dried and concentrated under reduced pressure to give 3-{(S)-2-(tert-butoxycarbonyl)amino-6-[(9H-fluoren-9-yl)methyloxycarbonyl]aminohexanoyl}-1,3-thiazolidine.

(2) Trifluoroacetic acid (10 mL) was added to the above-mentioned compound and the mixture was stirred for 1 hr. The mixture was concentrated under reduced pressure, and a saturated a aqueous sodium hydrogen carbonate solution was added. The mixture was extracted with ethyl acetate. The extract solution washed successively with saturated brine, dried and concentrated under reduced pressure to give the title compound (1.68 g).

MS (ESI) m/z: 440 [MH]$^+$

Reference Example 3

Synthesis of 3-((S)-1-tert-butoxycarbony-4-oxo-2-pyrrolidinylcarbony)-1,3-thiazolidine (1) N-tert-Butoxycarbonyl-L-trans-4-hydroxyproline (69.4 g) and thiazolidine (29.4 g) were dissolved in DMF (300 mL), and HOBT (50.5 g) and EDC hydrochloride (63.3 g) were added successively. The mixture was stirred at room temperature for 18 hr. The reaction solution was concentrated and saturated brine and a saturated aqueous sodium hydrogen carbonate solution were added to the concentrate. The mixture was extracted with ethyl acetate. The extract solution was dried and the solvent was evaporated under reduced pressure to give 3-((2S,4R)-1-tertbutoxycarbony-4-hydroxy-2-pyrrolidinylcarbonyl)-1,3-thiazolidine (56.3 g) as a colorless transparent oil.

(2) The above-mentioned compound (55.4 g) and triethylamine (46 mL) were dissolved in dichloromethane (350 mL), and a solution of pyridine sulfur trioxide complex (52.4 g) in dimethyl sulfoxide (150 mL) was added under ice-cooling and the mixture was stirred for 2 hr. A saturated a aqueous sodium hydrogen carbonate solution was added to the reaction solution. The mixture was extracted with ethyl acetate. The extract solution washed with saturated brine, dried and the solvent was evaporated under reduced pressure. The residue was purified by silica gel chromatography to give the title compound (30.3 g) as a white solid.

$^1$H-NMR (CDCl$_3$) δ 1.47 (9H, s), 2.45-2.57 (1H, m), 2.70-2.93 (1H, m), 2.97-3.22 (2H, m), 3.66-3.78 (0.6H, m), 3.80-4.10 (3H, m), 4.28-4.38 (0.4H, m), 4.45-5.08 (3H, m).

Example 1

Synthesis of 3-[(S)-2-amino-6-(2-nitrophenylamino)hexanoyl]-1,3-thiazolidine trifluoroacetate (1) The title compound (351 mg) of Reference Example 1 was dissolved in DMF (5 mL) and diisopropylethylamine (0.258 mL) and 1-fluoro-2-nitrobenzene (141 mg) were added. The mixture was stirred overnight at 80° C. The reaction solution was concentrated under reduced pressure, and a saturated a aqueous sodium hydrogen carbonate solution was added to the obtained residue. After stirring for 10 min, the reaction mixture was applied to ChemElut (Valian) and extracted with ethyl acetate 10 min later. The eluate was concentrated under reduced pressure, and the residue was purified by HPLC to give 3-[(S)-2-benzyloxycarbonylamino-6-(2-nitrophenylamino)hexanoyl]-1,3-thiazolidine (140 mg).

(2) The above-mentioned compound (140 mg) was dissolved in trifluoroacetic acid (7 mL) and thioanisole (0.35 mL) was added. The mixture was left standing overnight. Trifluoroacetic acid was evaporated and water was added. After washing with diethyl ether, 5% a aqueous ammonia was added to adjust pH to 8 and the mixture was concentrated under reduced pressure. The residue was purified by HPLC to give the title compound (55.2 mg) as a yellow solid.

MS (ESI) m/z 339 [MH]$^+$

Example 2

Synthesis of 3-[(S)-2-amino-6-(3-nitropyridin-2-ylamino) hexanoyl]-1,3-thiazolidine trifluoroacetate (1) In the same manner as in Example 1(1) and using the title compound (351 mg) of Reference Example 1 and 2-chloro-3-nitropyridine (158 mg), 3-[(S)-2-benzyloxycarbonylamino-6-(3-nitropyridin-2-ylamino)hexanoyl]-1,3-thiazolidine (284 mg) was obtained.

(2) In the same manner as in Example 1(2) and using the above-mentioned compound (284 mg), the title compound (108 mg) was obtained as a yellow solid.

MS (ESI) m/z 340 [MH]$^+$

Example 3

Synthesis of 3-[(S)-2-amino-6-(2-cyano-3-fluorophenylamino)hexanoyl]-1,3-thiazolidine trifluoroacetate (1) In the same manner as in Example 1(1) and using the title compound (351 mg) of Reference Example 1 and 2,6-difluorobenzonitrile (139 mg), 3-[(S)-2-benzyloxycarbonylamino-6-(2-cyano-3-fluorophenylamino)hexanoyl]-1,3-thiazolidine (250 mg) was obtained.

(2) In the same manner as in Example 1(2) and using the above-mentioned compound (250 mg), the title compound (110 mg) was obtained as a white solid.

MS (ESI) m/z 337 [MH]$^+$

Example 4

Synthesis of 3-[(S)-2-amino-6-(4-nitrophenylamino)hexanoyl]-1,3-thiazolidine (1) In the same manner as in Example 1(1) and using the title compound (351 mg) of Reference Example 1 and 4-fluoronitrobenzene (141 mg), 3-[(S)-2-benzyloxycarbonylamino-6-(4-nitrophenylamino)hexanoyl]-1,3-thiazolidine (298 mg) was obtained.

(2) In the same manner as in Example 1(2) and using the above-mentioned compound (298 mg), an a aqueous solution of trifluoroacetate of the title compound was obtained. Thereto was added potassium carbonate and the mixture was extracted with ethyl acetate. The extract solution was dried and concentrated under reduced pressure to give the title compound (66 mg).

MS (ESI) m/z 337 [MH]$^+$

Example 5

Synthesis of 3-[(S)-2-amino-6-(4-cyano-2-nitrophenylamino)hexanoyl]-1,3-thiazolidine (1) In the same manner as in Example 1(1) and using the title compound (351 mg) of Reference Example 1 and 4-chloro-3-nitrobenzonitrile (183 mg), 3-[(S)-2-benzyloxycarbonylamino-6-(4-cyano-2-nitrophenylamino)hexanoyl]-1,3-thiazolidine (404 mg) was obtained.

(2) In the same manner as in Example 1(2) and using the above-mentioned compound (404 mg), an a aqueous solution of trifluoroacetate of the title compound was obtained. Thereto was added potassium carbonate and the mixture was extracted with ethyl acetate. The extract solution was dried and concentrated under reduced pressure to give the title compound (124 mg).

MS (ESI) m/z 364 [MH]$^+$

Example 6

Synthesis of 3-[(S)-2-amino-6-(5-cyanopyridin-2-ylamino)hexanoyl]-1,3-thiazolidine dihydrochloride (1) In the same manner as in Example 1(1) and using the title compound (2.00 g) of Reference Example 1 and 2-chloro-5-cyanopyridine (1.38 g), 3-[(S)-2-benzyloxycarbonylamino-6-(5-cyanopyridin-2-ylamino)hexanoyl]-1,3-thiazolidine (1.65 g) was obtained.

(2) The above-mentioned compound (1.64 g) was dissolved in trifluoroacetic acid. (15 mL), and thioanisole (2.1 mL) was added. The mixture was stirred overnight. Trifluoroacetic acid was evaporated and a saturated a aqueous sodium hydrogen carbonate solution was added. The mixture was extracted with chloroform. The extract solution washed with saturated brine, dried and concentrated under reduced pressure. The residue was purified by silica gel column chromatography and the obtained oily substance was dissolved in ethyl acetate. Hydrochloric acid/ethyl acetate was added and the precipitated solid was collected by filtration to give the title compound (0.443 g) as a white solid.

MS (ESI) m/z 319 [MH]$^+$

Example 7

Synthesis of 3-[(S)-2-amino-6-(4-methanesulfonylphenylamino)hexanoyl]-1,3-thiazolidine (1) The title compound (1.68 g) of Reference Example 2 was dissolved in dichloromethane (25 mL), and, p-nitrophenyl carbonate Wang resin (2.15 g) was added. The mixture was stirred for 3 days. The solvent was removed and the resin was washed successively with DMF once, methanol and dichloromethane 3 times alternately and methanol 3 times, and dried under reduced pressure. 20% Piperidine/DMF was added to the obtained resin and, after stirring the mixture for 5 min, the resulting resin was collected by filtration, which operation was repeated 3 times. The resin washed successively with DMF 3 times, dichloromethane 3 times and methanol 3 times, and dried under reduced pressure.

(2) N-Methylpyrrolidone (7 mL) was added to the resin (700 mg) obtained by the above-mentioned operation, and 4-fluorophenylmethylsulfon (543 mg) and diisopropylethylamine (0.544 mL) were added. The mixture was stirred overnight at 100° C. The resin was collected by filtration, and washed successively with DMF 3 times, methanol and dichloromethane 3 times alternately and methanol 3 times. 50% Trifluoroacetic acid/dichloromethane (7 mL) was added to the obtained resin, and the mixture was stirred for 2 hr. The resin was filtered off and the residue was concentrated under reduced pressure. The obtained residue was purified by HPLC, and potassium carbonate was added to the eluate. The mixture was extracted with ethyl acetate and the extract solution was dried and concentrated under reduced pressure to give the title compound (26.9 mg).
MS (ESI) m/z 372 [MH]$^+$ Example 8

Synthesis of 3-[(S)-2-amino-6-(2-cyanophenylamino)hexanoyl]-1,3-thiazolidine

In the same manner as in Example 7(2) and using the resin (700 mg) of Example 7(1) and 2-fluorobenzonitrile (0.277 mL), the title compound (3 mg) was obtained.
MS (ESI) m/z 319 [MH]$^+$ Example 9

Synthesis of 3-[(S)-2-amino-6-(4-cyanophenylamino)hexanoyl]-1,3-thiazolidine

In the same manner as in Example 7(2) and using the resin (700 mg) of Example 7(1) and 4-fluorobenzonitrile (0.277 mL), the title compound (6.8 mg) was obtained.
MS (ESI) m/z 319 [MH]$^+$ Example 10

Synthesis of 3-[(S)-2-amino-6-(4-bromo-2-cyanophenylamino)hexanoyl]-1,3-thiazolidine In the same manner as in Example 7(2) and using the resin (700 mg) of Example 7(1) and 2-fluoro-5-bromobenzonitrile (480 mg), the title compound (24.8 mg) was obtained.
MS (ESI) m/z 397, 399 [MH]$^+$ Example 11

Synthesis of 3-{(S)-2-amino-6-[4-cyano-2-(trifluoromethyl)phenylamino]hexanoyl}-1,3-thiazolidine In the same manner as in Example 7(2) and using the resin (700 mg) of Example 7(1) and 4-fluoro-3-(trifluoromethyl)benzonitrile (453 mg), the title compound (18.8 mg) was obtained.
MS (ESI) m/z 387 [MH]$^+$ Example 12

Synthesis of 3-{(S)-2-amino-6-[3-chloro-5-(trifluoromethyl)pyridin-2-ylamino]hexanoyl}-1,3-thiazolidine In the same manner as in Example 7(2) and using the resin (700 mg) of Example 7(1) and 2,3-dichloro-5-(trifluoromethyl)pyridine (516 mg), the title compound (16.1 mg) was obtained.
MS (ESI) m/z 397, 399 [MH]$^+$ Example 13

Synthesis of 3-{(S)-2-amino-6-[4-cyano-3-(trifluoromethyl)phenylamino]hexanoyl}-1,3-thiazolidine In the same manner as in Example 7(2) and using the resin (700 mg) of Example 7(1) and 4-fluoro-2-(trifluoromethyl)benzonitrile (453 mg), the title compound (80.7 mg) was obtained.
MS (ESI) m/z 387 [MH]$^+$ Example 14

Synthesis of 3-[(S)-2-amino-6-(5-nitropyridin-2-ylamino)hexanoyl]-1,3-thiazolidine In the same manner as in Example 7(2) and using the resin (700 mg) of Example 7(1) and 5-nitro-2-chloropyridine (379 mg), the title compound (20 mg) was obtained.
MS (ESI) m/z 340 [MH]$^+$ Example 15

Synthesis of 3-[(S)-2-amino-6-(2-cyano-4-fluorophenylamino)hexanoyl]-1,3-thiazolidine In the same manner as in Example 7(2) and using the resin (700 mg) of Example 7(1) and 2,5-difluorobenzonitrile (334 mg), the title compound (7.9 mg) was obtained.
MS (ESI) m/z 337 [MH]$^+$ Example 16

Synthesis of 3-[(S)-2-amino-6-(4-cyano-2-fluorophenylamino)hexanoyl]-1,3-thiazolidine In the same manner as in Example 7(2) and using the resin (700 mg) of Example 7(1) and 3,4-difluorobenzonitrile (334 mg), the title compound (24 mg) was obtained.
MS (ESI) m/z 337 [MH]$^+$ Example 17

Synthesis of 3-[(S)-2-amino-6-(3-chloro-2-cyanophenylamino)hexanoyl]-1,3-thiazolidine In the same manner as in Example 7(2) and using the resin (700 mg) of Example 7(1) and 2-chloro-6-fluorobenzonitrile (372 mg), the title compound (18.7 mg) was obtained.
MS (ESI) m/z 353, 355 [MH]$^+$ Example 18

Synthesis of 3-[(S)-2-amino-6-(3-chloro-4-cyanophenylamino)hexanoyl]-1,3-thiazolidine In the same manner as in Example 7(2) and using the resin (700 mg) of Example 7(1) and 2-chloro-4-fluorobenzonitrile (372 mg), the title compound (52.7 mg) was obtained.
MS (ESI) m/z 353, 355 [MH]$^+$ Example 19

Synthesis of 3-[(S)-2-amino-6-(4-chloro-2-cyanophenylamino)hexanoyl]-1,3-thiazolidine In the same manner as in Example 7(2) and using the resin (700 mg) of Example 7(1) and 5-chloro-2-fluorobenzonitrile (372 mg), the title compound (77.3 mg)—was obtained.
MS (ESI) m/z 353, 355 [MH]$^+$

Example 20

Synthesis of 3-[(S)-2-amino-6-(2-bromo-4-cyanophenylamino)hexanoyl]-1,3-thiazolidine In the same manner as in Example 7(2) and using the resin (700 mg) of Example 7(1) and 3-bromo-4-fluorobenzonitrile (477 mg), the title compound (80.3 mg) was obtained.
MS (ESI) m/z 397, 399 [MH]$^+$

Example 21

Synthesis of 3-[(S)-2-amino-6-(2-cyano-5-bromophenylamino)hexanoyl]-1,3-thiazolidine In the same manner as in Example 7(2) and using the resin (700 mg) of Example 7(1) and 2-fluoro-4-bromobenzonitrile (477 mg), the title compound (54.9 mg) was obtained.
MS (ESI) m/z 397, 399 [MH]$^+$

Example 22

Synthesis of 3-[(S)-2-amino-6-(2-cyano-4-trifluoromethylphenylamino)hexanoyl]-1,3-thiazolidine In the same manner as in Example 7(2) and using the resin (700 mg) of Example 7(1) and 2-fluoro-5-(trifluoromethyl) benzonitrile (454 mg), the title compound (73.9 mg) was obtained.
MS (ESI) m/z 397 [MH]$^+$

Example 23

Synthesis of 3-[(S)-2-amino-6-(5-trifluoromethylpyridin-2-ylamino)hexanoyl]-1,3-thiazolidine In the same manner as in Example 7(2) and using the resin (700 mg) of Example 7(1) and 2-chloro-5-trifluoromethylpyridine (434 mg), the title compound (10 mg) was obtained.
MS (ESI) m/z 363 [MH]$^+$

Example 24

Synthesis of 3-[(S)-2-amino-6-(pyrimidin-2-ylamino)hexanoyl]-1,3-thiazolidine

In the same manner as in Example 7(2) and using the resin (700 mg) of Example 7(1) and 2-chloropyrimidine (274 mg), the title compound (13.2 mg) was obtained.
MS (ESI) m/z 296 [MH]$^+$

Example 25

Synthesis of 3-[(S)-2-amino-6-(4-trifluoromethylpyrimidin-2-ylamino)hexanoyl]-1,3-thiazolidine In the same manner as in Example 7(2) and using the resin (700 mg) of Example 7(1) and 2-chloro-4-trifluoromethylpyrimidine (437 mg), the title compound (54.6 mg) was obtained.
MS (ESI) m/z 364 [MH]$^+$

Example 26

Synthesis of 3-[(S)-2-amino-6-(3-cyanopyridin-2-ylamino)hexanoyl]-1,3-thiazolidine In the same manner as in Example 7(2) and using the resin (700 mg) of Example 7(1) and 2-chloro-3-cyanopyridine (331 mg), the title compound (30.8 mg) was obtained.
MS (ESI) M/z 320 [MH]$^+$

Example 27

Synthesis of 3-[(S)-2-amino-6-(2-cyano-4-nitrophenylamino)hexanoyl]-1,3-thiazolidine In the same manner as in Example 7(2) and using the resin (700 mg) of Example 7(1) and 2-fluoro-5-nitrobenzonitrile (398 mg), the title compound (59.4 mg) was obtained.
MS (ESI) m/z 364 [MH]$^+$

Example 28

Synthesis of 3-{(S)-2-amino-6-[4-(2-trifluoromethyl-4-quinolyl)piperazin-1-yl]hexanoyl}-1,3-thiazolidine dihydrochloride (1) N-α-benzyloxycarbonyl-N-ε-tert-butoxycarbonyl-L-lysine (8.60 g) was dissolved in formic acid (50 mL), and the mixture was stirred overnight at room temperature. The reaction solution was concentrated under reduced pressure, and the residue was dissolved in acetic acid (100 mL), and sodium acetate (1.85 g) and sodium nitrite (4.68 g) were added. The mixture was stirred overnight at 40° C. The reaction solution was concentrated under reduced pressure, and water was added to the residue. The mixture was extracted with chloroform. The extract solution was dried and concentrated under reduced pressure to give (S)-6-acetoxy-2-(benzyloxycarbonyl)aminohexane acid (3.52 g).

(2) The above-mentioned compound (3.23 g) was dissolved in DMF (60 mL), and thiazolidine (0.79 mL), HOBT monohydrate (1.68 g) and EDC hydrochloride (2.1 g) were added successively. The mixture was stirred overnight at room temperature. The reaction solution was concentrated under reduced pressure, and a saturated a aqueous sodium hydrogen carbonate solution was added. The mixture was extracted with ethyl acetate. The extract solution washed successively with saturated brine, dried and concentrated under reduced pressure to give 3-[(S)-6-acetoxy-2-(benzyloxycarbonyl)aminohexanoyl]-1,3-thiazolidine (1.5 g).

(3) The above-mentioned compound (1.5 g) was dissolved in methanol (15 mL) and potassium carbonate (0.69 g) was added. The mixture was stirred at room temperature for 2 hr. The reaction solution was filtered, and the filtrate was concentrated under reduced pressure. The residue was purified by silica gel column chromatography to give 3-[(S)-2-(benzyloxycarbonyl)amino-6-hydroxyhexanoyl]-1,3-thiazolidine (0.64 g) as a colorless oil.

(4) The above-mentioned compound (590 mg) and triethylamine (0.26 mL) were dissolved in dichloromethane (10 mL) and methanesulfonyl chloride (0.14 mL) was added dropwise. The mixture was stirred at room temperature for 3 hr. The reaction solution washed with water, dried and concentrated under reduced pressure. The residue was dissolved in DMF (10 mL) and 1-(2-trifluoromethyl-4-quinolyl)piperazine (469 mg) and potassium carbonate (461 mg) were added. The mixture was stirred at 80° C. for 6 hr. The reaction solution was concentrated under reduced pressure, and water was added to the residue. The mixture was extracted with ethyl acetate and the extract solution was dried and concentrated under reduced pressure. The residue was purified by silica gel column chromatography to give 3-{(S)-2-benzyloxycarbonylamino-6-[4-(2-trifluoromethyl-4-quinolyl)piperazin-1-yl]hexanoyl}-1,3-thiazolidine (270 mg).

(5) The above-mentioned compound (260 mg) was dissolved in trifluoroacetic acid (5 mL) and thioanisole (0.5 mL) was added. The mixture was stirred overnight at room temperature. Trifluoroacetic acid was evaporated, and a saturated a aqueous sodium hydrogen carbonate solution was added. The mixture was extracted with chloroform. The extract solution was dried and concentrated under reduced pressure. The residue was purified by silica gel column chromatography, and the obtained oil was dissolved in ethyl acetate. Hydrochloric acid/ethyl acetate was added. The precipitated solid was collected by filtration to give the title compound (22.9 mg) as a white solid.

MS (ESI) m/z 481 [MH]+

Example 29

Synthesis of 3-{(2S,4S)-4-[4-(2-pyrimidinyl)-1-piperazinyl]-2-pyrrolidinylcarbonyl}-1,3-thiazolidine trihydrochloride (1) The title compound (1.50 g) of Reference Example 3 and 2-(1-piperazinyl)pyrimidine (0.903 g) were dissolved in 1,2-dichloroethane (25 mL), and acetic acid (0.29 mL) and triacetoxysodium borohydride (2.12 g) were added. The mixture was stirred at room temperature for 16 hr. A saturated a aqueous sodium hydrogen carbonate solution was added to the reaction solution and the mixture was extracted with chloroform. The extract solution washed with saturated brine, dried and concentrated under reduced pressure. The residue was purified by silica gel column chromatography to give 3-{(2S,4S)-1-tert-butoxycarbonyl-4-[4-(2-pyrimidinyl)-1-piperazinyl]-2-pyrrolidinylcarbonyl}-1,3-thiazolidine (2.12 g) as a white solid.

(2) The above-mentioned compound (2.12 g) was dissolved in a 5.6 mol/L hydrochloric acid-ethanol solution (10 mL) and the mixture was stirred at room temperature for 22 hr. The reaction solution was concentrated under reduced pressure to give the title compound (2.05 g) as a white solid.

$^1$H-NMR (DMSO-d$_6$) δ 2.33 (1H, m), 2.92-4.33 (15H, m), 4.47-4.77 (5H, m), 6.79 (1H, t, J=4.8 Hz), 8.46 (2H, d, J=4.8 Hz), 9.14 (1H, brs), 11.01 (1H, brs).

Example 30

Synthesis of 3-{(2S,4S)-4-[4-(4-trifluoromethyl-6-phenyl-2-pyrimidinyl)-1-piperazinyl]-2-pyrrolidinylcarbonyl}-1,3-thiazolidine dihydrochloride (1) 4,4,4-Trifluoro-1-phenyl-1,3-butanedione (10.8 g) and urea (6.01 g) were dissolved in ethanol (25 mL) and concentrated hydrochloric acid (5 mL) was added. The mixture was heated under reflux for 2.5 hr. The reaction solution was concentrated under reduced pressure, and water was added. The mixture washed with chloroform. A saturated a aqueous sodium hydrogen carbonate solution was added to the a aqueous layer and the precipitate was collected by filtration to give 2-hydroxy-4-phenyl-6-trifluoromethylpyrimidine (5.03 g) as a pale-pink crystalline powder.

(2) Phosphorus oxychloride (7.8 mL) was added to the above-mentioned compound (5.03 g) and the mixture was stirred at 100° C. for 9 hr. Ice was added to the reaction solution and a 5 mol/L a aqueous sodium hydroxide solution was added to basify the solution. The precipitate was collected by filtration to give 2-chloro-4-phenyl-6-trifluoromethylpyrimidine (5.71 g) as a white solid.

(3) piperazine (25.8 g) was melted at 130° C. and the above-mentioned compound (13.1 g) was added. The mixture was stirred for 2 hr. Water was added to the reaction solution, and the mixture was extracted with chloroform. The extract solution washed with saturated brine, dried and concentrated under reduced pressure. Hexane was added to the residue, and the precipitate was collected by filtration to give 1-(4-trifluoromethyl-6-phenyl-2-pyrimidinyl)piperazine (2.92 g) as a white solid.

(4) In the same manner as in Example 29(1) and using the title compound (0.601 g) of Reference Example 3 and the above-mentioned compound (0.678 g), 3-{(2S,4S)-1-tert-butoxycarbonyl-4-[4-(4-trifluoromethyl-6-phenyl-2-pyrimidinyl)-1-piperazinyl]-2-pyrrolidinylcarbonyl}-1,3-thiazolidine (1.18 g) was obtained as a white solid.

(5) In the same manner as in Example 29(2) and using the above-mentioned compound (1.18 g), the title compound (1.02 g) was obtained as a white powder.

$^1$H-NMR (DMSO-d$_6$) δ 2.29 (1H, m), 2.90-4.05 (15H, m), 4.37-4.86 (5H, m), 7.54-7.65 (3H, m), 7.76 (1H, s), 8.27-8.30 (2H, m), 9.15 (1H, brs), 10.76 (1H, brs).

Example 31

Synthesis of 3-{(2S,4S)-4-[4-(2-trifluoromethyl-4-pyrimidinyl)-1-piperazinyl]-2-pyrrolidinylcarbonyl}-1,3-thiazolidine dihydrochloride (1) Phosphorus oxychloride (15 mL) was added to 2-trifluoromethyl-4-hydroxypyrimidine (2.50 g) and the mixture was stirred at 60° C. for 1 hr. The mixture was concentrated under reduced pressure, and a saturated a aqueous sodium hydrogen carbonate solution was added to the residue. The mixture was extracted with ethyl acetate. The extract solution washed with saturated brine, dried and concentrated under reduced pressure to give 2-trifluoromethyl-4-hydroxypyrimidine (0.600 g) as a brown oil.

(2) piperazine (845 mg) was dissolved in DMF (6 mL) with heating and a DMF solution (1 mL) of the above-mentioned compound (597 mg) were added at 40° C. The mixture was stirred at room temperature for 2 hr. The reaction solution was concentrated under reduced pressure, and water was added to the residue. The mixture was extracted with chloroform. The extract solution washed with saturated brine, dried and concentrated under reduced pressure to give 1-(2-trifluoromethyl-4-pyrimidinyl)piperazine (680 mg) as a brown solid.

(3) In the same manner as in Example 29(1) and using the title compound (0.832 g) of Reference Example 3 and the above-mentioned compound (0.676 g), 3-{(2S,4S)-1-tert-butoxycarbonyl-4-[4-(2-trifluoromethyl-4-pyrimidinyl)-1-piperazinyl]-2-pyrrolidinylcarbonyl}-1,3-thiazolidine (1.28 g) was obtained as a pale-brown solid.

(4) The above-mentioned compound (1.27 g) was dissolved in ethanol (3 mL) and a 4.1 mol/L hydrochloric acid-ethanol solution (3 mL) was added. The mixture was stirred at room temperature for 13 hr. The reaction solution was concentrated under reduced pressure, and ethyl acetate was added to the residue. The precipitate was collected by filtration to give the title compound (1.02 g) as a white solid.

$^1$H-NMR (DMSO-d$_6$) δ 2.15-2.33 (1H, m), 2.90-4.05 (16H, m), 4.45-4.78 (3H, m), 7.24 (1H, d, J=6.3 Hz), 8.45 (1H, d, J=6.3 Hz), 9.12 (1H, brs), 10.83 (1H, brs), 12.7 (1H, brs).

Example 32

Synthesis of 3-((2S,4S)-4-{4-[1-(4-methoxyphenyl)-2-imidazolyl]-1-piperazinyl}-2-pyrrolidinylcarbonyl)-1,3-thiazolidine trihydrochloride (1) 1-Benzyloxycarbonylpiperazine (6.35 g) was dissolved in acetone (40 mL) and 4-methoxyphenyl isothiocyanate (5.19 g) were added under ice-cooling. The mixture was stirred at room temperature for 2 days. The reaction solution was concentrated under reduced pressure, and the residue was dissolved in dichloromethane (80 mL). Methyl iodide (2.7 mL) was added under ice-cooling, and the mixture was stirred at room temperature for 17 hr. The reaction solution was added to a saturated a aqueous sodium hydrogen carbonate solution, and the mixture was extracted with dichloromethane. The extract solution washed with saturated brine, dried and concentrated under reduced pressure to give 1-benzyloxycarbonyl-4-[(methylthio)(4-methoxyphenyl)iminomethyl]piperazine (12.8 g) as a brown oil.

(2) The above-mentioned compound (12.8 g) and aminoacetaldehyde dimethyl acetal (6.1 mL) were dissolved in pyridine (60 mL). The mixture was stirred with heating at 110° C. for 25 hr. The reaction solution was concentrated under reduced pressure, and a saturated a aqueous sodium hydrogen carbonate solution was added to the residue. The mixture was extracted with chloroform. The extract solution washed with saturated brine, dried and concentrated under reduced pressure. The residue was dissolved in 2 mol/L hydrochloric acid (120 mL), and the mixture was heated at 100° C. for 1 hr. A saturated a aqueous sodium hydrogen carbonate solution was added to the reaction solution, and the mixture was extracted with chloroform. The extract solution washed with saturated brine, dried and concentrated under reduced pressure. The residue was purified by silica gel chromatography to give 1-benzyloxycarbonyl-4-[1-(4-methoxyphenyl)-2-imidazolyl]piperazine (7.91 g) as a brown oil.

(3) The above-mentioned compound (7.91 g) and thioanisole (6 mL) were dissolved in trifluoroacetic acid (60 mL) and the mixture was stirred at room temperature for 6 hr. The reaction solution was concentrated under reduced pressure, and a saturated aqueous sodium hydrogen carbonate solution was added to the residue. The mixture was extracted with chloroform. The extract solution washed with saturated brine, dried and concentrated under reduced pressure. The residue was purified by HPLC to give 1-[1-(4-methoxyphenyl)-2-imidazolyl]piperazine (0.628 g) as a colorless transparent oil.

(4) In the same manner as in Example 29(1) and using the above-mentioned compound (624 mg) and the title compound (601 mg) of Reference Example 3, 3-((2S,4S)-1-tert-butoxycarbonyl-4-{4-[1-(4-methoxyphenyl)-2-imidazolyl]-1-piperazinyl}-2-pyrrolidinylcarbonyl)-1,3-thiazolidine (416 mg) was obtained as a white solid.

(5) The above-mentioned compound (411 mg) was dissolved in ethyl acetate (1 mL) and 4 mol/L hydrochloric acid-ethyl acetate (1 mL) was added. The mixture was stirred at room temperature for 18 hr. The precipitate was collected by filtration to give the title compound (413 mg) as a white powder.

$^1$H-NMR (DMSO-$d_6$) δ 2.04-2.20 (1H, m), 2.82-4.00 (16H, m), 4.42-4.75 (3H, m), 7.15 (1H, d, J=8.9 Hz), 7.42-7.47 (2H, m), 7.59 (1H, d, J=8.9 Hz), 9.04 (1H, brs), 10.88 (1H, brs), 14.1 (1H, brs).

Example 33

Synthesis of 3-{(2S,4S)-4-[4-(1-phenyl-5-pyrazolyl)-1-piperazinyl]-2-pyrrolidinylcarbonyl}-1,3-thiazolidine trihydrochloride (1) Ethyl 3,3-diethoxypropionate (5.34 g) was dissolved in tetrahydrofuran (60 mL) and a 1 mol/L a aqueous sodium hydroxide solution (29 mL) was added at room temperature. The mixture was stirred for 12 hr. The reaction solution was concentrated under reduced pressure, and the residue was suspended in DMF (60 mL). HOBT (5.16 g), EDC hydrochloride (6.46 g) and 1-benzyloxycarbonylpiperazine (6.20 g) were added at room temperature and the mixture was stirred for 6 hr. The solvent was evaporated under reduced pressure, and water was added to the residue. The mixture was extracted with ethyl acetate. The extract solution washed successively with a saturated a aqueous sodium hydrogen carbonate solution and saturated brine and dried. The solvent was evaporated under reduced pressure. The residue was purified by silica gel chromatography to give 1-benzyloxycarbonyl-4-(3,3-diethoxypropionyl)piperazine (10.0 g) as an oil.

(2) The above-mentioned compound (3.28 g) was dissolved in chloroform (30 mL), and a 50% a aqueous trifluoroacetic acid solution (20 mL) was added under ice-cooling. The mixture was stirred at room temperature for 24 hr. The reaction solution was extracted with chloroform. The extract solution washed successively with water and saturated brine and dried. The solvent was evaporated under reduced pressure and the residue was dissolved in ethanol (60 mL). Phenylhydrazine (0.886 mL) and methanesulfonic acid (0.060 mL) were added and the mixture was stirred at room temperature for 3 hr. Pyridine (1 mL) was added to the reaction solution and the solvent was evaporated under reduced pressure. The residue was dissolved in pyridine (50 mL), and phosphorus oxychloride (1.68 mL) was added. The mixture was stirred at room temperature for 18 hr. The reaction solution was concentrated under reduced pressure, and water was added to the residue. The mixture was extracted with ethyl acetate. The extract solution washed with saturated brine and dried. The solvent was evaporated under reduced pressure and the residue was purified by silica gel chromatography to give 1-benzyloxycarbonyl-4-(1-phenyl-5-pyrazolyl)piperazine (0.218 g) as an oil.

(3) The above-mentioned compound (218 mg) was dissolved in methanol (10 mL) and 10% palladium/carbon (200 mg) was added. The mixture was stirred under a hydrogen atmosphere at room temperature for 6 hr. The reaction solution was filtered, and the filtrate was concentrated under reduced pressure to give 1-(1-phenyl-5-pyrazolyl)piperazine (137 mg) as a white powder.

(4) In the same manner as in Example 29(1) and using the above-mentioned compound (137 mg) and the title compound (180 mg) of Reference Example 3, 3-{(2S,4S)-1-tert-butoxycarbonyl-4-[4-(1-phenyl-5-pyrazolyl)-1-piperazinyl]-2-pyrrolidinylcarbonyl}-1,3-thiazolidine (204 mg) was obtained as a white powder.

(5) The above-mentioned compound (204 mg) was dissolved in ethanol (10 mL) and 4 mol/L hydrochloric acid/ethyl acetate (3 mL) was added at room temperature. The mixture was stirred for 64 hr. The reaction solution was concentrated under reduced pressure, and the residue was dissolved in methanol. Ethyl acetate was added and the precipitate was collected by filtration to give the title compound (170 mg) as a white solid.

$^1$H-NMR (500 MHz, DMSO-$d_6$) δ 2.10-2.30 (1H, m), 2.80-4.10 (16H, m), 4.46-4.74 (3H, m), 6.10 (1H, d, J=1.7 Hz), 7.34-7.37 (1H, m), 7.49-7.52 (2H, m), 7.56 (1H, d, J=1.7 Hz), 7.79-7.81 (2H, m), 9.07 (1H, brs), 10.65 (1H, brs).

Example 34

Synthesis of 3-((2S,4S)-4-{4-[1-(4-fluorophenyl) - 5-pyrazolyl]-1-piperazinyl}-2-pyrrolidinylcarbonyl)-1,3-thiazolidine trihydrochloride (1) In the same manner as in Example 33(2) and using the product (5.70 g) of Example 33(1) and 4-fluorophenylhydrazine (1.05 g), 1- benzyloxycarbonyl-4-[1-(4-fluorophenyl)-5-pyrazolyl]piperazine (0.075 g) was obtained as an oil.

(2) In the same manner as in Example 33(3) and using the above-mentioned compound (62 mg) and 10% palladium/carbon (10 mg), 1-[1-(4-fluorophenyl)-5-pyrazolyl]piperazine (40 mg) was obtained as a white powder.

(3) In the same manner as in Example 29(1) and using the above-mentioned compound (40 mg) and the title compound (48 mg) of Reference Example 3, 3-((2S,4S)-1-tert-butoxycarbonyl-4-{4-[1-(4-fluorophenyl)-5-pyrazolyl]-1-piperazinyl}-2-pyrrolidinylcarbonyl)-1,3-thiazolidine (76 mg) was obtained as a white powder.

(4) In the same manner as in Example 33(5) and using the above-mentioned compound (76 mg), the title compound (56 mg) was obtained as a white solid.

$^1$H-NMR (DMSO-d$_6$) δ 2.00-2.33 (1H, m), 2.80-4.10 (16H, m), 4.45-4.74 (3H, m), 6.11 (1H, d, J=1.8 Hz), 7.29-7.36 (2H, m), 7.56 (1H, d, J=1.8 Hz), 7.78-7.85 (2H, m), 9.04 (1H, brs), 10.51 (1H, brs).

Example 35

Synthesis of 3-((2S,4S)-4-{4-[1-(4-fluorophenyl) - 3-methyl-5-pyrazolyl]-1-piperazinyl}-2-pyrrolidinyl-carbonyl)-1,3-thiazolidine trihydrochloride (1) 1-tert-Butoxycarbonylpiperazine (103 g) was dissolved in DMF (600 mL) and diketene (56 mL) was added over 20 min at room temperature. The mixture was stirred for 2 hr. The solvent was evaporated under reduced pressure and the residue was diluted with ethyl acetate. The mixture washed with water and saturated brine and dried. The solvent was evaporated under reduced pressure to give 1-acetoacetyl-4-tert-butoxycarbonyl piperazine (129 g) as a pale-brown powder.

(2) The above-mentioned compound (3.92 g) was dissolved in ethanol (200 mL) and 4-fluorophenylhydrazine hydrochloride (2.36 g) and molecular sieves 3A (10 g) were added at room temperature. The mixture was stirred for 4 hr. The molecular sieves were filtered off and pyridine (4 mL) was added to the filtrate. The solvent was evaporated under reduced pressure. The residue was dissolved in pyridine (200 mL) and phosphorus oxychloride (3.0 mL) was added at room temperature. The mixture was stirred for 18 hr. The reaction solution was concentrated under reduced pressure, and water was added to the residue. The mixture was extracted with ethyl acetate. The extract solution washed with saturated brine, dried and concentrated under reduced pressure. The residue was purified by silica gel chromatography to give 1-tert-butoxycarbonyl-4-[1-(4-fluorophenyl)-3-methyl-5-pyrazolyl]piperazine (2.03 g) as a brown oil.

(3) The above-mentioned compound (2.03 g) was dissolved in dichloromethane (20 mL) and trifluoroacetic acid (4 mL) was added at room temperature. The mixture was stirred for 18 hr.

The reaction solution was concentrated under reduced pressure, and a saturated a aqueous sodium hydrogen carbonate solution was added to the residue. The mixture was extracted with ethyl acetate and the extract solution was dried and concentrated under reduced pressure to give 1-[1-(4-fluorophenyl)-3-methyl-5-pyrazolyl]piperazine (1.42 g) as a brown oil.

(4) In the same manner as in Example 29(1) and using the above-mentioned compound (1.42 g) and the title compound (1.36 g) of Reference Example 3, 3-((2S,4S)-1-tert-butoxycarbonyl-4-{4-[1-(4-fluorophenyl) -3-methyl-5-pyrazolyl]-1-piperazinyl}-2-pyrrolidinylcarbonyl)-1,3-thiazolidine (1.85 g) was obtained as a white powder.

(5) The above-mentioned compound (1.85 g) was dissolved in methanol (10 mL) and chloroform (5 mL), and a 4 mol/L hydrochloric acid-ethyl acetate solution (5 mL) was added. The mixture was stirred for 18 hr. The reaction solution was concentrated under reduced pressure to give the title compound (1.37 g) as a white solid.

$^1$H-NMR (DMSO-d$_6$) δ 2.17 (3H, s), 2.20-2.40 (1H, m), 2.90-4.35 (16H, m), 4.43-4.82 (3H, m), 5.95 (1H, s), 7.21-7.37 (2H, m), 7.74-7.89 (2H, m), 9.13 (1H, brs), 11.10 (1H, brs).

Example 36

Synthesis of 3-((2S,4S)-4-{4-[1-(2-fluorophenyl) - 3-methyl-5-pyrazolyl]-1-piperazinyl}-2-pyrrolidinyl-carbonyl)-1,3-thiazolidine trihydrochloride (1) The product (1.92 g) of Example 35(1) was dissolved in ethanol (50 mL) and 2-fluorophenylhydrazine hydrochloride (1.16 g) was added at room temperature. The mixture was stirred for 4 hr. Pyridine (1 mL) was added to the reaction solution and the solvent was evaporated under reduced pressure. The residue was dissolved in pyridine (30 mL) and phosphorus oxychloride (1.33 mL) was added at room temperature. The mixture was stirred for 19 hr. The reaction solution was concentrated under reduced pressure, and water was added to the residue. The mixture was extracted with ethyl acetate. The extract solution washed successively with a saturated a aqueous sodium hydrogen carbonate solution and saturated brine and dried. The solvent was evaporated under reduced pressure. The residue was purified by silica gel chromatography to give 1-tert-butoxycarbonyl-4-[1-(2-fluorophenyl)-3-methyl-5-pyrazolyl]piperazine (0.640 g) as an oil.

(2) The above-mentioned compound (640 mg) was dissolved in dichloromethane (10 mL) and trifluoroacetic acid (3 mL) was added at room temperature. The mixture was stirred for 3 hr. The solvent was evaporated under reduced pressure, and a saturated a aqueous sodium hydrogen carbonate solution was added to the residue. The mixture was extracted with chloroform. The extract solution was dried and concentrated under reduced pressure to give 1-[1-(2-fluorophenyl) -3-methyl-5-pyrazolyl]piperazine (430 mg) as an oil.

(3) In the same manner as in Example 29(1) and using the above-mentioned compound (430 mg) and the title compound (472 mg) of Reference Example 3, 3-((2S,4S)-1-tert-butoxycarbonyl-4-{4-[1-(2-fluorophenyl) -3-methyl-5-pyrazolyl]-1-piperazinyl}-2-pyrrolidinylcarbonyl)-1,3-thiazolidine (778 mg) was obtained as a pale-yellow powder.

(4) The above-mentioned compound (778 mg) was dissolved in dichloromethane (5 mL) and trifluoroacetic acid (5 mL) was added at room temperature. The mixture was stirred for 1 hr. The solvent was evaporated under reduced pressure, and the residue was dissolved in ethyl acetate (20 mL). To this solution was added 4 mol/L hydrochloric acid/ethyl acetate (1.5 mL), and the precipitate was collected by filtration to give the title compound (608 mg) as a white solid. $^1$H-NMR (500 MHz, DMSO-d$_6$) δ 2.03-2.25 (1H, m), 2.16 (3H, s), 2.72-4.00 (16H, m), 4.45-4.71 (3H, m), 5.91 (1H, s), 7.32-7.35 (1H, m), 7.40-7.44 (1H, m), 7.51-7.57 (2H, m), 9.02 (1H, brs), 10.41 (1H, brs).

Example 37

Synthesis of 3-((2S,4S)-4-{4-[1-(3-fluorophenyl) - 3-methyl-5-pyrazolyl]-1-piperazinyl}-2-pyrrolidinyl-carbonyl)-1,3-thiazolidine trihydrochloride (1) In the same manner as in Example 36(1) and using the product (5.10 g) of Example 35(1) and 3-fluorophenylhydrazine hydrochloride (3.22 g), 1-tert-butoxycarbonyl-4-[1-(3-fluorophenyl)-3-methyl-5-pyrazolyl]piperazine (1.55 g) was obtained as a yellow solid.

(2) In the same manner as in Example 36(2) and using the above-mentioned compound (1.55 g), 1-[1-(3-fluorophenyl)-3-methyl-5-pyrazolyl]piperazine (1.12 g) was obtained as an oil.

(3) In the same manner as in Example 29(1) and using the above-mentioned compound (1.12 g) and the title compound (1.17 g) of Reference Example 3, 3-((2S,4S)-1-tert-butoxycarbonyl-4-{4-[1-(3-fluorophenyl) -3-methyl-5-pyrazolyl]-1-piperazinyl}-2-pyrrolidinylcarbonyl)-1,3-thiazolidine (1.97 g) was obtained as a white powder.

(4) In the same manner as in Example 36(4) and using the above-mentioned compound (1.97 g), the title compound (1.60 g) was obtained as a white solid.

$^1$H-NMR (DMSO-$d_6$) δ 2.10-2.35 (1H, m), 2.17 (3H, s), 2.90-4.15 (16H, m), 4.46-4.76 (3H, m), 5.98 (1H, s), 7.11-7.19 (1H, m), 7.47-7.55 (1H, m), 7.59-7.64 (1H, m), 7.70-7.73 (11H, m), 9.09 (1H, brs), 10.79 (1H, brs).

Example 38

Synthesis of 3-((2S,4S)-4-{4-[1-(4-chlorophenyl) - 3-methyl-5-pyrazolyl]-1-piperazinyl}-2-pyrrolidinyl-carbonyl)-1,3-thiazolidine trihydrochloride (1) In the same manner as in Example 35(2) and using the compound (5.0 g) of Example 35(1) and 4-chlorophenylhydrazine hydrochloride (3.5 g), 1-tert-butoxycarbonyl-4-[1-(4-chlorophenyl)-3-methyl-5-pyrazolyl]piperazine (2.2 g) was obtained as a brown solid.

(2) In the same manner as in Example 36(2) and using the above-mentioned compound (2.2 g), 1-[1-(4-chlorophenyl)-3-methyl-5-pyrazolyl]piperazine (1.7 g) was obtained as a brown oil.

(3) In the same manner as in Example 29(1) and using the above-mentioned compound (1.7 g) and the title compound (1.5 g) of Reference Example 3, 3-((2S,4S)-1-tert-butoxycarbonyl-4-{4-[1-(4-chlorophenyl) -3-methyl-5-pyrazolyl]-1-piperazinyl}-2-pyrrolidinylcarbonyl)-1,3-thiazolidine (2.8 g) was obtained as a white solid.

(4) The above-mentioned compound (2.8 g) was dissolved in ethyl acetate (20 mL), and 4 mol/L hydrochloric acid-ethyl acetate (40 mL) was added at room temperature. The mixture was stirred for 3 hr. The precipitate was collected by filtration to give the title compound (2.2 g) as a white powder.

$^1$H-NMR (DMSO-$d_6$) δ 2.17 (3H, s), 2.25-2.40 (1H, m), 2.95-4.15 (17H, m), 4.46-4.77 (3H, m), 5.97 (1H, s), 7.48-7.53 (2H, m), 9.13 (1H, brs), 11.01 (1H, brs).

Example 39

Synthesis of 3-((2S,4S)-4-{4-[1-(4-cyanophenyl) - 3-methyl-5-pyrazolyl]-1-piperazinyl}-2-pyrrolidinyl-carbonyl)-1,3-thiazolidine dihydrochloride (1) In the same manner as in Example 35(2) and using product (5.0 g) of Example 35(1) and 4-cyanophenylhydrazine hydrochloride (3.3 g), 1-tert-butoxycarbonyl-4-[1-(4-cyanophenyl)-3-methyl-5-pyrazolyl]piperazine (2.7 g) was obtained as a pale-yellow solid.

(2) In the same manner as in Example 36(2) and using the above-mentioned compound (2.7 g), 1-[1-(4-cyanophenyl)-3-methyl-5-pyrazolyl]piperazine (2.1 g) was obtained as a pale-yellow solid.

(3) In the same manner as in Example 29(1) and using the above-mentioned compound (2.1 g) and the title compound (1.8 g) of Reference Example 3, 3-((2S,4S)-1-tert-butoxycarbonyl-4-{4-[1-(4-cyanophenyl) -3-methyl-5-pyrazolyl]-1-piperazinyl}-2-pyrrolidinylcarbonyl)-1,3-thiazolidine (3.2 g) was obtained as a white solid.

(4) In the same manner as in Example 38(4) and using the above-mentioned compound (3.2 g), the title compound (2.3 g) was obtained as a white powder.

$^1$H-NMR (DMSO-$d_6$) δ 2.19 (3H, s), 2.20-2.40 (1H, m), 2.95-4.15 (17H, m), 4.46-4.77 (3H, m), 6.05 (1H, s), 7.91 (2H, d, J=9.0 Hz), 8.08 (2H, d, J=9.0 Hz), 9.13 (1H, brs), 10.09 (1H, brs).

Example 40

Synthesis of 3-((2S,4S)-4-{4-[3-methyl-1-(2-pyridyl) -5-pyrazolyl]-1-piperazinyl}-2-pyrrolidinyl-carbonyl)-1,3-thiazolidine dihydrochloride (1) The product (3.92 g) of Example 35(1) was dissolved in ethanol (200 mL) and 2-hydrazinopyridine (1.58 g), methanesulfonic acid (0.094 mL) and molecular sieves 3A (10 g) were added at room temperature. The mixture was stirred for 18 hr. The molecular sieves were filtered off and pyridine (4 mL) was added to the filtrate. The solvent was evaporated under reduced pressure. The residue was dissolved in pyridine (200 mL) and phosphorus oxychloride (3.0 mL) was added at room temperature. The mixture was stirred for 18 hr. The reaction solution was concentrated under reduced pressure, and a saturated a aqueous sodium hydrogen carbonate solution was added to the residue. The mixture was extracted with ethyl acetate. The extract solution washed with saturated brine, dried and concentrated under reduced pressure. The residue was purified by silica gel chromatography to give 1-tert-butoxycarbonyl-4-[3-methyl-1-(2-pyridyl)-5-pyrazolyl]piperazine (230 mg).

(2) The above-mentioned compound (230 mg) was dissolved in dichloroethane (10 mL), and trifluoroacetic acid (2 mL) was added at room temperature. The mixture was stirred for 1 hr. The reaction solution was concentrated under reduced pressure, and a saturated a aqueous sodium hydrogen carbonate solution was added to the residue. The mixture was extracted with chloroform. The extract solution was dried and concentrated under reduced pressure to give 1-[3-methyl-1-(2-pyridyl)-5-pyrazolyl]piperazine (180 mg).

(3) In the same manner as in Example 29(1) and using the above-mentioned compound (180 mg) and the title compound (222 mg) of Reference Example 3, 3-((2S,4S)-1-tert-butoxycarbonyl-4-{4-[3-methyl-1-(2-pyridyl)-5-pyrazolyl]-1-piperazinyl}-2-pyrrolidinylcarbonyl)-1,3-thiazolidine (284 mg) was obtained as a pale-yellow oil.

(4) The above-mentioned compound (284 mg) was dissolved in methanol (4 mL) and chloroform (2 mL), and a 4 mol/L hydrochloric acid-ethyl acetate solution (6 mL) was added. The mixture was stirred for 2 hr. The reaction solution was concentrated under reduced pressure to give the title compound (176 mg) as a white solid.

$^1$H-NMR (DMSO-$d_6$) δ 2.19 (3H, s), 2.24-2.44 (1H, m), 2.88-4.20 (16H, m), 4.42-4.80 (3H, m), 5.99 (1H, s), 7.30-

7.40 (1H, m), 7.77 (1H, d, J=8.3 Hz), 7.92-8.01 (1H, m), 8.46-8.54 (1H, m), 9.14 (1H, brs), 11.05 (1H, brs).

Example 41

Synthesis of 3-((2S,4S)-4-{4-[3-methyl-1-(3-pyridyl)-5-pyrazolyl]-1-piperazinyl}-2-pyrrolidinylcarbonyl)-1,3-thiazolidine trimaleate (1) 3-Aminopyridine (20 g) was dissolved in concentrated hydrochloric acid (125 mL), and an a aqueous solution (40 mL) of sodium nitrite (15 g) was added at −10° C. over 20 min. The mixture was stirred at 0° C. for 2 hr. This solution was added to a solution (200 mL) of tin(II) chloride (80 g) in concentrated hydrochloric acid at −2° C. over 20 min. The mixture was stirred for 14 hr. The precipitate was filtered off and ice was added. The mixture was made strongly-basic with a 50% a aqueous potassium hydroxide solution and extracted with dichloromethane. The extract solution was dried and concentrated under reduced pressure. The residue was dissolved in ethyl acetate (400 mL) and 4 mol/L of hydrochloric acid-ethyl acetate (55 mL) was added under ice-cooling. The precipitate was collected by filtration to give 3-hydrazinopyridine dihydrochloride (18 g) as a pale-yellow solid.

(2) The above-mentioned compound (3.5 g) was suspended in ethanol (100 mL), and the product (5.0 g) of Example 35(1), molecular sieves 3A (10 g) and pyridine (20 mL) were added at room temperature. The mixture was stirred for 2 hr. Pyridine (100 mL) was added to the reaction mixture, and the mixture was filtered off. The filtrate was concentrated under reduced pressure. The residue was suspended in pyridine (100 mL), and phosphorus oxychloride (3.8 mL) was added at room temperature. The mixture was stirred for 13 hr. The reaction solution was concentrated under reduced pressure, and a saturated a aqueous sodium hydrogen carbonate solution was added to the residue. The mixture was extracted with chloroform. The extract solution was dried and the solvent was evaporated under reduced pressure. The residue was purified by silica gel chromatography to give 1-tert-butoxycarbonyl-4-[3-methyl-1-(3-pyridyl)-5-pyrazolyl]piperazine (1.3 g) as a brown solid.

(3) In the same manner as in Example 36(2) and using the above-mentioned compound (1.3 g), 1-[3-methyl-1-(3-pyridyl)-5-pyrazolyl]piperazine (876 mg) was obtained as a brown oil.

(4) In the same manner as in Example 29(1) and using the above-mentioned compound (0.876 g) and the title compound (0.900 g) of Reference Example 3, 3-((2S,4S)-1-tert-butoxycarbonyl-4-{4-[3-methyl-1-(3-pyridyl)-5-pyrazolyl]-1-piperazinyl}-2-pyrrolidinylcarbonyl)-1,3-thiazolidine (1.5 g) was obtained as a brown oil.

(5) The above-mentioned compound (1.5 g) was dissolved in ethyl acetate (20 mL), and 4 mol/L hydrochloric acid-ethyl acetate (40 mL) was added at room temperature. The mixture was stirred for 14 hr. After the reaction, water and 1 mol/L hydrochloric acid were added. The a aqueous layer was separated and made strongly-basic with a 10 mol/L a aqueous sodium hydroxide solution. The mixture was extracted with chloroform. The extract solution was dried and concentrated under reduced pressure. The residue was dissolved in ethanol (100 mL), and a solution of maleic acid (950 mg) in ethanol (20 mL) was added under ice-cooling. The precipitate was collected by filtration to give the title compound (1.0 g) as a white powder.

$^1$H-NMR (DMSO-$d_6$) δ 1.60-1.78 (1H, s), 2.17 (3H, s), 2.50-3.90 (20H, m), 4.42-4.71 (4H, m), 5.91 (1H, s), 6.19 (6H, s), 7.49-7.53 (1H, m), 8.12-8.16 (1H, m), 8.18-8.50 (1H, m), 8.98-8.99 (1H, m).

Example 42

Synthesis of 3-((2S,4S)-4-{4-[3-methyl-1-(4-pyridyl)-5-pyrazolyl]-1-piperazinyl}-2-pyrrolidinylcarbonyl)-1,3-thiazolidine trimaleate (1) 4-Chloropyridine hydrochloride (14 g) was added to hydrazine monohydrate (50 mL) and the mixture was stirred at 120° C. for 1 hr. A 1 mol/L a aqueous sodium hydroxide solution (100 mL) and sodium chloride were added to the reaction solution. The mixture was extracted with ethyl acetate and the extract solution was dried and concentrated under reduced pressure. The residue was dissolved in ethyl acetate (100 mL) and 4 mol/L hydrochloric acid-ethyl acetate (50 mL) was added under ice-cooling. The precipitate was collected by filtration to give 4-hydrazinopyridine dihydrochloride (16 g) as a pale-yellow solid.

(2) In the same manner as in Example 41(2) and using the above-mentioned compound (3.5 g) and the product (5.0 g) of Example 35(1), 1-tert-butoxycarbonyl-4-[3-methyl-1-(4-pyridyl)-5-pyrazolyl]piperazine (3.4 g) was obtained as a pale-yellow solid.

(3) In the same manner as in Example 36(2) and using the above-mentioned compound (3.4 g), 1-[3-methyl-1-(4-pyridyl)-5-pyrazolyl]piperazine (2.4 g) was obtained as a pale-yellow solid.

(4) In the same manner as in Example 29(1) and using the above-mentioned compound (2.4 g) and the title compound (2.5 g) of Reference Example 3, 3-((2S,4S)-1-tert-butoxycarbonyl-4-{4-[3-methyl-1-(4-pyridyl)-5-pyrazolyl]-1-piperazinyl}-2-pyrrolidinylcarbonyl)-1,3-thiazolidine (4.1 g) was obtained as a white solid.

(5) In the same manner as in Example 41(5) and using the above-mentioned compound (4.1 g), the title compound (4.3 g) was obtained as a white powder.

$^1$H-NMR (DMSO-$d_6$) δ 1.60-1.80 (1H, m), 2.18 (3H, s), 2.55-3.90 (20H, m) 4.43-4.72 (4H, m), 5.98 (1H, s), 6.18 (6H, s), 7.92-7.94 (2H, m), 8.61-8.63 (2H, m)

Example 43

Synthesis of 3-((2S,4S)-4-{4-[1-(5-cyano-2-pyridyl)-3-methyl-5-pyrazolyl]-1-piperazinyl}-2-pyrrolidinylcarbonyl)-1,3-thiazolidine dihydrochloride (1) 2-Chloro-5-cyanopyridine (5.0 g) was dissolved in THF (100 mL) and added to hydrazine monohydrate (9.0 mL). The mixture was refluxed for 3 hr. The reaction solution was concentrated under reduced pressure, and a saturated a aqueous sodium hydrogen carbonate solution and sodium chloride were added to the residue. The mixture was extracted with ethyl acetate and the extract solution was dried and concentrated under reduced pressure to give 2-cyano-5-hydrazinopyridine (4.3 g) as a pale-brown solid.

(2) The above-mentioned compound (2.6 g) was suspended in ethanol (200 mL), and the product (5.0 g) of Example 35(1), molecular sieves 3A (10 g) and methanesulfonic acid (2.6 g) were added. The mixture was stirred at room temperature for 18 hr. Pyridine (10 mL) was added to the reaction mixture and molecular sieves 3A were filtered off. The filtrate was concentrated under reduced pressure. The residue was dissolved in pyridine (200 mL), and phosphorus oxychloride (3.8 mL) was added at room temperature. The mixture was stirred for 15 hr. The reaction solution was concentrated under reduced pressure, and a saturated a aqueous sodium hydrogen carbonate solution was added to the residue. The mixture was extracted with ethyl acetate. The extract solution washed successively with water and saturated brine, dried and concentrated under reduced pressure. The residue was purified by silica gel chromatography to give 1-tert-butoxycarbonyl-4-[1-(5-cyano-2-pyridyl)-3-methyl-5-pyrazolyl]piperazine (1.3 g) as a pale-yellow solid.

(3) In the same manner as in Example 36(2) and using the above-mentioned compound (1.3 g), 1-[1-(5-cyano-2-pyridyl)-3-methyl-5-pyrazolyl]piperazine (1.1 g) was obtained as a brown solid.

(4) In the same manner as in Example 29(1) and using the above-mentioned compound (1.1 g) and the title compound (0.900 g) of Reference Example 3, 3-((2S,4S)-1-tert-butoxycarbonyl-4-{4-[1-(5-cyano-2-pyridyl) -3-methyl-5-pyrazolyl]-1-piperazinyl}-2-pyrrolidinylcarbonyl)-1,3-thiazolidine (1.6 g) was obtained as a white solid.

(5) In the same manner as in Example 38(4) and using the above-mentioned compound (1.6 g), the title compound (1.3 g) was obtained as a white powder.

$^1$H-NMR (DMSO-$d_6$) δ 2.21 (3H, s), 2.25-2.45 (1H, m), 2.95-4.19 (17H, m), 4.47-4.77 (3H, m), 6.05 (1H, s), 7.97 (1H, d, J=8.7 Hz), 8.37 (1H, dd, J=8.7, 2.3 Hz), 8.93 (1H, d, J=2.3 Hz), 9.15 (1H, brs), 10.80 (1H, brs).

Example 44

Synthesis of 3-{(2S,4S)-4-[4-(3-trifluoromethyl-1-phenyl-5-pyrazolyl)-1-piperazinyl]-2-pyrrolidinylcarbonyl}-1,3-thiazolidine trihydrochloride (1) 1-Benzyloxycarbonylpiperazine (19.0 g) was dissolved in pyridine (150 mL) and acetic anhydride (9.0 mL) was added at room temperature. The mixture was stirred for 18 hr. The reaction solution was concentrated under reduced pressure, and a 10% a aqueous citric acid solution was added to the residue.

The mixture was extracted with ethyl acetate. The extract solution washed with saturated brine, dried and concentrated under reduced pressure to give 4-acetyl-1-benzyloxycarbonylpiperazine (22.6 g) as an oil.

(2) The above-mentioned compound (7.12 g) was dissolved in tetrahydrofuran (150 mL), and a 1 mol/L lithium bis(trimethylsilyl)amide-tetrahydrofuran solution (41 mL) was added dropwise at −78° C. over 40 min. After stirring at said temperature for 1 hr, a solution of ethyl trifluoroacetate (4.85 mL) in tetrahydrofuran (20 mL) was added to the reaction solution. The mixture was gradually warmed to room temperature and stirred for 18 hr. A saturated a aqueous ammonium chloride solution was added to the reaction solution, and the mixture was extracted with ethyl acetate. The extract solution was washed with saturated brine, dried and concentrated under reduced pressure. The residue was purified by silica gel chromatography to give 1-benzyloxycarbonyl-4-trifluoroacetoacetylpiperazine (7.35 g) as a pale-yellow solid.

(3) In the same manner as in Example 36(1) and using the above-mentioned compound (1.96 g) and phenylhydrazine (0.540 mL), 1-benzyloxycarbonyl-4-(3-trifluoromethyl-1-phenyl-5-pyrazolyl)piperazine (0.416 g) was obtained as an oil.

(4) In the same manner as in Example 33(3) and using the above-mentioned compound (416 mg), 1-(3-trifluoromethyl-1-phenyl-5-pyrazolyl)piperazine (286 mg) was obtained as a white solid.

(5) In the same manner as in Example 29(1) and using the above-mentioned compound (286 mg) and the title compound (280 mg) of Reference Example 3, 3-{(2S,4S)-1-tert-butoxycarbonyl-4-[4-(3-trifluoromethyl -1-phenyl-5-pyrazolyl)-1-piperazinyl]-2-pyrrolidinylcarbonyl}-1,3-thiazolidine (322 mg) was obtained as a pale-brown powder.

(6) In the same manner as in Example 33(5) and using the above-mentioned compound (322 mg), the title compound (294 mg) was obtained as a white solid.

$^1$H-NMR (DMSO-$d_6$) δ 2.00-2.28 (1H, m), 2.80-4.00 (16H, m), 4.44-4.74 (3H, m), 6.64 (1H, s), 7.44-7.49 (1H, m), 7.54-7.59 (2H, m), 7.77-7.79 (2H, m), 9.03 (1H, brs), 10.55 (1H, brs).

Example 45

Synthesis of 3-{(2S,4S)-4-[4-(1H-indazol-3-yl)-1-piperazinyl]-2-pyrrolidinylcarbonyl}-1,3-thiazolidine trihydrochloride (1) In the same manner as in Example 29(1) and using 1-(1H-indazol-3-yl)piperazine (178 mg) and the title compound (264 mg) of Reference Example 3, 3-{(2S,4S)-1-tert-butoxycarbonyl-4-[4-(1H-indazol-3-yl)-1-piperazinyl]-2-pyrrolidinylcarbonyl}-1,3-thiazolidine (442 mg) was obtained as a colorless transparent oil.

(2) The above-mentioned compound (442 mg) was dissolved in methanol (10 mL) and chloroform (5 mL), and a 4 mol/L hydrochloric acid-ethyl acetate solution (5 mL) was added. The mixture was stirred for 18 hr. The reaction solution was concentrated under reduced pressure to give the title compound (210 mg) as a white solid.

$^1$H-NMR (DMSO-$d_6$) 2.20-2.48 (1H, m), 2.90-4.30 (16H, m), 4.41-4.80 (3H, m), 7.02 (1H, t, J=6.9 Hz), 7.25-7.46 (2H, m), 7.79 (1H, d, J=8.4 Hz), 9.20 (1H, brs), 10.78 (1H, brs), 12.26 (1H, s), 12.34 (1H, brs).

Example 46

Synthesis of 3-{(2S,4S)-4-[4-(4-trifluoromethyl-6-methoxy-2-quinolyl)-1-piperazinyl]-2-pyrrolidinylcarbonyl}-1,3-thiazolidine dihydrochloride (1) p-Anisidine (10 g) was dissolved in toluene (100 mL), and ethyl trifluoroacetoacetate (12 mL) and molecular sieves 4A (5.0 g) were added. The mixture was refluxed for 2 hr. The molecular sieves 4A were filtered off, and the filtrate was concentrated under reduced pressure. 75% Polyphosphoric acid (40 mL) was added to the residue and the mixture was stirred at 130° C. for 2 hr. The reaction solution was poured onto ice and the precipitate was collected by filtration, dried and washed with a mixed solution of chloroform-ether (1:2) to give 0.4-trifluoromethyl-2-hydroxy-6-methoxyquinoline (4.9 g) as a white solid.

(2) The above-mentioned compound (4.9 g) was added to phosphorus oxychloride (8.0 mL) and the mixture was stirred at 100° C. for 3 hr. Ice was added to the reaction solution and then a 4 mol/L a aqueous sodium hydroxide solution was added to strong basify the mixture. The precipitate was collected by filtration to give 2-chloro-4-trifluoromethyl-6-methoxyquinoline (4.9 g) as a white solid.

(3) piperazine (10 g) was melted at 130° C. and the above-mentioned compound (4.9 g) was added. The mixture was stirred for 2 hr and water was added to the reaction mixture. The mixture was extracted with ethyl acetate and chloroform. The extract solution was dried and the solvent was evaporated under reduced pressure. The residue was purified by silica gel chromatography to give 1-(4-trifluoromethyl-6-methoxy-2-quinolyl)piperazine (5.7 g) as a yellow solid.

(4) In the same manner as in Example 29(1) and using the above-mentioned compound (1.1 g) and the title compound (0.900 g) of Reference Example 3, 3-{(2S,4S)-1-tert-butoxycarbonyl-4-[4-(4-trifluoromethyl-6-methoxy-2-quinolyl)-1-piperazinyl]-2-pyrrolidinylcarbonyl}-1,3-thiazolidine (1.7 g) was obtained as a white solid.

(5) In the same manner as in Example 38(4) and using the above-mentioned compound (1.7 g), the title compound (1.6 g) was obtained as a yellow powder.

$^1$H-NMR (DMSO-$d_6$) δ 2.30-2.45 (1H, m), 2.95-3.17 (3H, m), 3.25-4.25 (15H, m), 4.48-4.78 (5H, m), 7.16 (1H, brs), 7.45 (1H, dd, J=9.0, 2.4 Hz), 7.74 (1H, s), 7.80 (1H, d, J=9.0 Hz), 9.16 (1H, brs), 11.06 (1H, brs).

Example 47

Synthesis of 3-{(2S,4S)-4-[4-(4-trifluoromethyl-8-methoxy-2-quinolyl)-1-piperazinyl]-2-pyrrolidinyl-carbonyl}-1,3-thiazolidine trihydrochloride (1) Orthoanisidine (50 g) and ethyl 4,4,4-trifluoroacetoacetate (71.3 mL) were dissolved in benzene (800 mL) and p-toluenesulfonic acid monohydrate (7.72 g) was added. The mixture was heated under reflux for 20 hr. The reaction solution was concentrated under reduced pressure, and a saturated a aqueous sodium hydrogen carbonate solution was added. The mixture was extracted with ethyl acetate. The extract solution washed with saturated brine, dried and concentrated under reduced pressure. 75% Polyphosphoric acid (300 mL) was added to the residue and the mixture was stirred at 90° C. for 6 hr. The reaction solution was poured onto ice water (3 L), and the precipitated solid was collected by filtration. The solid was dissolved in ethyl acetate and the mixture washed successively with a saturated a aqueous sodium hydrogen carbonate solution, water and saturated brine, dried and concentrated under reduced pressure to give a mixture (31.7 g) containing 4-trifluoromethyl-2-hydroxy-8-methoxyquinoline as a pale-brown solid.

(2) Phosphorus oxychloride (48.6 mL) was added to the above-mentioned mixture (31.7 g) and the mixture was stirred at 100° C. for 2 hr. Ice was added to the reaction solution and 5 mol/L sodium hydroxide was added to basify the mixture. The precipitate was collected by filtration to give a mixture (34.2 g) containing 2-chloro-4-trifluoromethyl-8-methoxyquinoline as a pale-brown solid.

(3) piperazine (25.8 g) was melted at 130° C., and the above-mentioned compound (13.1 g) was added. The mixture was stirred for 3 hr. Water was added to the reaction solution, and the mixture was extracted with ethyl acetate. The extract solution was dried and concentrated under reduced pressure, and the residue was purified by silica gel column chromatography to give 1-(4-trifluoromethyl-8-methoxy-2-quinolyl)piperazine (5.21 g) as a pale-yellow solid.

(4) In the same manner as in Example 29(1) and using the above-mentioned compound (0.933 g) and the title compound (0.891 g) of Reference Example 3, 3-{(2S,4S)-1-tert-butoxycarbonyl-4-[4-(4-trifluoromethyl -8-methoxy-2-quinolyl)-1-piperazinyl]-2-pyrrolidinylcarbonyl}-1,3-thiazolidine (1.82 g) was obtained as a yellow solid.

(5) The above-mentioned compound (1.82 g) was dissolved in a 4.1 mol/L hydrochloric acid-ethanol solution (1 mL) and the mixture was stirred at room temperature for 3 hr. The reaction solution was concentrated under reduced pressure, and a saturated a aqueous sodium hydrogen carbonate solution was added. The mixture was extracted with chloroform. The extract solution washed with saturated brine and dried. The solvent was evaporated and the residue was purified by HPLC. A 4.1 mol/L hydrochloric acid-ethanol solution (1 mL) was added, and the mixture was concentrated under reduced pressure to give the title compound (0.310 g) as a white powder.

$^1$H-NMR (DMSO-$d_6$) δ 2.11 (1H, m), 2.67-3.92 (20H, m), 4.29-4.78 (3H, m), 7.04 (1H, m), 7.17-7.25 (2H, m), 7.55 (1H, s), 8.98 (1H, brs), 10.46 (1H, brs).

Example 48

Synthesis of 3-{(2S,4S)-4-[4-(2-trifluoromethyl-6-hydroxy-4-quinolyl)-1-piperazinyl]-2-pyrrolidinyl-carbonyl}-1,3-thiazolidine dihydrochloride (1) p-Anisidine (10 g) was dissolved in toluene (100 mL) and ethyl trifluoroacetoacetate (12 mL) and molecular sieves 4A (5.0 g) were added. The mixture was refluxed for 2 hr. The molecular sieves 4A were filtered off, and the filtrate was concentrated under reduced pressure. 75% Polyphosphoric acid (40 mL) was added to the residue and the mixture was stirred at 130° C. for 2 hr. The reaction solution was poured onto ice and the precipitate was collected by filtration. The precipitate was dried and a mixed solution of chloroform-ether (1:2) was added, and insoluble materials were filtered off. The filtrate was concentrated under reduced pressure to give a mixture (8.1 g) containing 2-trifluoromethyl-4-hydroxy-6-methoxyquinoline as an oil.

(2) In the same manner as in Example 46(2) and using the above-mentioned mixture (8.1 g) and phosphorus oxychloride (12 mL), 4-chloro-2-trifluoromethyl-6-methoxyquinoline (4.2 g) was obtained as a white solid.

(3) In the same manner as in Example 46(3) and using the above-mentioned compound (4.2 g) and piperazine (10 g), 1-(2-trifluoromethyl-6-methoxy-4-quinolyl)piperazine (3.6 g) was obtained as a pale-yellow solid.

(4) In the same manner as in Example 29(1) and using the above-mentioned compound (2.2 g) and the title compound (1.7 g) of Reference Example 3, 3-{(2S,4S)-1-tert-butoxycarbonyl-4-[4-(2-trifluoromethyl-6-methoxy-4-quinolyl)-1-piperazinyl]-2-pyrrolidinylcarbonyl}-1,3-thiazolidine (3.6 g) was obtained as a white solid.

(5) The above-mentioned compound (3.6 g) was dissolved in ethyl acetate (20 mL), and 4 mol/L hydrochloric acid-ethyl acetate (100 mL) was added at room temperature. The mixture was stirred for 10 hr. The precipitate was collected by filtration and dissolved in water. The mixture washed with chloroform and the a aqueous solution thereof was basified with a saturated a aqueous sodium hydrogen carbonate solution. The mixture was extracted with chloroform. The extract solution was dried and concentrated under reduced pressure to give 3-{(2S,4S)-4-[4-(2-trifluoromethyl-6-methoxy-4-quinolyl) -1-piperazinyl]-2-pyrrolidinylcarbonyl}-1,3-thiazolidine (2.8 g) as a white solid.

(6) The above-mentioned compound (1.1 g) was dissolved in dichloromethane (40 mL) and boron tribromide (0.96 mL) was added at −78° C. The mixture was stirred at room temperature for 4 hr. A saturated a aqueous sodium hydrogen carbonate solution was added to the reaction solution. The mixture was extracted with ethyl acetate. The extract solution washed with saturated brine, dried and residue was purified by HPLC. The purified product was dissolved in ethyl acetate and 4 mol/L hydrochloric acid-ethyl acetate was added. The precipitate was collected by filtration to give the title compound (236 mg) as a pale-yellow powder.

$^1$H-NMR (DMSO-$d_6$) δ 2.10-2.39 (1H, m), 2.89-3.99 (17H, m), 4.48-4.77 (3H, m), 7.25 (1H, s), 7.32 (1H, d, J=2.4 Hz), 7.43 (1H, dd, J=9.0, 2.4 Hz), 7.98 (1H, d, J=9.0 Hz), 9.09 (1H, brs), 10.42 (1H, brs), 10.53 (1H, brs).

Example 49

Synthesis of 3-{(2S,4S)-4-[4-(6-trifluoromethoxy-2-trifluoromethyl-4-quinolyl)-1-piperazinyl]-2-pyrrolidinylcarbonyl}-1,3-thiazolidine dihydrochloride (1) 4-Trifluoromethylaniline (25.0 g) and ethyl trifluoroacetoacetate (22.7 mL) was dissolved in acetic acid (140 mL) and the mixture was stirred at room temperature for 23 hr. The reaction solution was concentrated under reduced pressure, and a saturated a aqueous sodium hydrogen carbonate solution was added. The mixture was extracted with chloroform. The extract solution washed with saturated brine, dried and concentrated under reduced pressure. To the residue was added diphenyl ether (140 mL), and the mixture was stirred at 250° C. for 1.5 hr. Hexane (140 mL) was added to the reaction solution and the precipitate was collected by filtration to give 6-trifluoromethoxy-2-trifluoromethyl-4-hydroxyquinoline (12.0 g) as a white crystalline powder.

(2) In the same manner as in Example 46(2) and using the above-mentioned compound (12.0 g), 4-chloro-6-trifluoromethoxy-2-trifluoromethylquinoline (12.1 g) was obtained as a white solid.

(3) In the same manner as in Example 46(3) and using the above-mentioned compound (12.1 g), 1-(6-trifluoromethoxy-2-trifluoromethyl-4-quinolyl)piperazine (14.3 g) was obtained as a pale-yellow solid.

(4) In the same manner as in Example 29(1) and using the above-mentioned compound (402 mg) and the title compound (300 mg) of Reference Example 3, 3-{(2S,4S)-1-tert-butoxycarbonyl-4-[4-(6-trifluoromethoxy-2-trifluoromethyl-4-quinolyl)-1-piperazinyl]-2-pyrrolidinylcarbonyl}-1,3-thiazolidine (601 mg) was obtained as a white solid.

(5) In the same manner as in Example 29(2) and using the above-mentioned compound (601 mg), the title compound (521 mg) was obtained as a fine yellow powder.

$^1$H-NMR (DMSO-$d_6$) δ 2.46 (1H, m), 3.03-3.25 (3H, m), 3.31-4.05 (13H, m) 4.24 (1H, m), 4.52-4.85 (3H, m), 7.52 (1H, s), 7.92 (1H, d, J=9.2 Hz), 8.02 (1H, s), 8.31 (1H, d, J=9.2 Hz), 9.25 (1H, brs), 10.19 (1H, brs).

Example 50

Synthesis of 3-{(2S,4S)-4-[4-(2-trifluoromethyl-8-hydroxy-4-quinolyl)-1-piperazinyl]-2-pyrrolidinylcarbonyl}-1,3-thiazolidine trihydrochloride (1) Orthoanisidine (50 g) and ethyl 4,4,4-trifluoroacetoacetate (71.3 mL) were dissolved in benzene (800 mL) and p-toluenesulfonic acid monohydrate (7.72 g) was added. The mixture was heated under reflux for 20 hr. The reaction solution was concentrated under reduced pressure, and a saturated a aqueous sodium hydrogen carbonate solution was added. The mixture was extracted with ethyl acetate. The extract solution washed with saturated brine, dried and concentrated under reduced pressure. 75% Polyphosphoric acid (300 mL) was added to the residue and the mixture was stirred at 90° C. for 6 hr. The reaction solution was poured onto ice water (3 L) and the precipitated solid was collected by filtration. The solid was dissolved in ethyl acetate and washed successively with a saturated a aqueous sodium hydrogen carbonate solution, water and saturated brine, dried and concentrated under reduced pressure to give a mixture (31.7 g) containing 2-trifluoromethyl-4-hydroxy-8-methoxyquinoline as a pale-brown solid.

(2) Phosphorus oxychloride (48.6 mL) was added to the above-mentioned compound (31.7 g) and the mixture was stirred at 100° C. for 2 hr. Ice was added to the reaction solution, and 5 mol/L sodium hydroxide was added to basify the solution. The precipitate was collected by filtration to give a mixture (34.2 g) containing 4-chloro-2-trifluoromethyl-8-methoxyquinoline as a pale-brown solid.

(3) piperazine (25.8 g) was melted at 130° C. and the above-mentioned mixture (13.1 g) was added. The mixture was stirred for 3 hr. Water was added to the reaction solution, and the mixture was extracted with ethyl acetate. The extract solution was dried and concentrated under reduced pressure, and the residue was purified by silica gel column chromatography to give 1-(2-trifluoromethyl-8-methoxy-4-quinolyl)piperazine (8.48 g) as a yellow solid. p (4) In the same manner as in Example 29(1) and using the above-mentioned compound (0.933 g) and the title compound (0.891 g) of Reference Example 3, 3-{(2S,4S)-1-tert-butoxycarbonyl-4-[4-(2-trifluoromethyl -8-methoxy-4-quinolyl)-1-piperazinyl]-2-pyrrolidinylcarbonyl}-1,3-thiazolidine (1.54 g) was obtained as a white solid.

(5) In the same manner as in Example 48(6) and using the above-mentioned compound (394 mg), the title compound (109 mg) was obtained as a yellow powder.

1H-NMR (DMSO-$d_6$) δ 2.34 (1H, m), 2.90-4.23 (17H, m), 4.48-4.81 (3H, m), 7.22 (1H, dd, J=1.5, 7.2 Hz), 7.36 (1H, s), 7.49-7.59 (2H, m), 9.15 (1H, brs), 10.16 (1H, brs), 10.77 (1H, brs).

Example 51

Synthesis of 3-{(2S,4S)-4-[4-(8-ethoxy-2-trifluoromethyl-4-quinolyl)-1-piperazinyl]-2-pyrrolidinylcarbonyl}-1,3-thiazolidine trihydrochloride (1) The product (4.86 g) of Example 50(3) was dissolved in dichloromethane and boron tribromide (7.39 mL) was added at −78° C. The mixture was stirred at room temperature for 3 hr. The reaction solution was poured into water and sodium hydrogen carbonate was added to adjust its pH to 8. The mixture was extracted with chloroform. The extract solution washed with saturated brine, dried and concentrated under reduced pressure to give 1-(2-trifluoromethyl-8-hydroxy-4-quinolyl)piperazine (1.52 g) as a pale-yellow solid.

(2) In the same manner as in Example 29(1) and using the above-mentioned compound (0.648 g) and the title compound (0.595 g) of Reference Example 3, 3-{(2S,4S)-1-tert-butoxycarbonyl-4-[4-(2-trifluoromethyl -8-hydroxy-4-quinolyl)-1-piperazinyl]-2-pyrrolidinylcarbonyl}-1,3-thiazolidine (1.30 g) was obtained as a fine yellow solid.

(3) Sodium hydride (40 mg) was suspended in DMF (1 mL) and the above-mentioned compound (291 mg) was added under ice-cooling. The mixture was stirred for 10 min. Ethyl p-toluenesulfonate (200 mg) was added to the reaction mixture and the mixture was stirred at 70° C. for 4 hr. Water was added to the reaction mixture, and the mixture was extracted with chloroform. The extract solution washed with saturated brine, dried and concentrated under reduced pressure. The residue was purified by silica gel column chromatography to give 3-{(2S,4S)-1-tert-butoxycarbonyl-4-[4-(8-ethoxy-2-trifluoromethyl-4-quinolyl)-1-piperazinyl]-2-pyrrolidinylcarbonyl}-1,3-thiazolidine (280 mg) as a fine yellow solid.

(4) In the same manner as in Example 47(5) and using the above-mentioned compound (280 mg), the title compound (141 mg) was obtained as a yellow powder.

¹H-NMR (DMSO-d₆) δ 1.57 (3H, t, J=6.9 Hz), 2.54 (1H, m), 3.02-4.17 (16H, m), 4.19-4.46 (3H, m), 4.51-5.18 (3H, m), 7.42 (1H, m), 7.51 (1H, s), 7.73-7.77 (2H, m), 9.33 (1H, brs), 10.94 (1H, brs).

Example 52

Synthesis of 3-{(2S,4S)-4-[4-(2-trifluoromethyl -8-isopropoxy-4-quinolyl)-1-piperazinyl]-2-pyrrolidinylcarbonyl}-1,3-thiazolidine trihydrochloride (1) In the same manner as in Example 51(3) and using the product (291 mg) of Example 51(2) and p-toluenesulfonic acid isopropoxy ester (161 mg), 3-{(2S,4S)-1-tert-butoxycarbonyl-4-[4-(2-trifluoromethyl -8-isopropoxy-4-quinolyl)-1-piperazinyl]-2-pyrrolidinylcarbonyl}-1,3-thiazolidine (28 mg) was obtained as a colorless oil.

(2) In the same manner as in Example 29(2) and using the above-mentioned compound (28 mg), the title compound (10 mg) was obtained as a yellow powder.

¹H-NMR (DMSO-d₆) δ 1.43 (3H, s), 1.45 (3H, s), 2.45 (1H, m), 3.04-3.26 (6H, m), 3.61-4.03 (10H, m), 4.22 (1H, m), 4.50-4.97 (4H, m), 7.40 (1H, m), 7.44 (1H, s), 7.67-7.69 (2H, m), 9.24 (1H, brs), 10.99 (1H, brs).

Example 53

Synthesis of 3-{(2S,4S)-4-[4-(8-trifluoromethoxy 2-trifluoromethyl-4-quinolyl)-1-piperazinyl]-2-pyrrolidinylcarbonyl}-1,3-thiazolidine dihydrochloride (1) In the same manner as in Example 47(1) and using 2-trifluoromethylaniline (5.10 g), 8-trifluoromethoxy-2-trifluoromethyl-4-hydroxyquinoline (0.345 g) was obtained as a white powder.

(2) In the same manner as in Example 47(2) and using the above-mentioned compound (345 mg), 4-chloro-8-trifluoromethoxy-2-trifluoromethylquinoline (316 mg) was obtained as an orange oil.

(3) In the same manner as in Example 47(3) and using the above-mentioned compound (316 mg), 1-(8-trifluoromethoxy-2-trifluoromethyl-4-quinolyl)piperazine (349 mg) was obtained as a yellow oil.

(4) In the same manner as in Example 29(1) and using the above-mentioned compound (349 mg) and the title compound (261 mg) of Reference Example 3, 3-{(2S,4S)-1-tert-butoxycarbonyl-4-[4-(8-trifluoromethoxy-2-trifluoromethyl-4-quinolyl)-1-piperazinyl]-2-pyrrolidinylcarbonyl}-1,3-thiazolidine (513 mg) was obtained as a white solid.

(5) In the same manner as in Example 47(5) and using the above-mentioned compound (513 mg), the title compound (365 mg) was obtained as a white powder.

¹H-NMR (DMSO-d₆) δ 2.26 (1H, m), 2.80-4.19 (17H, m), 4.30-4.72 (3H, m), 7.38 (1H, s), 7.68 (1H, dd, J=7.9, 7.9 Hz), 7.82 (1H, d, J=7.9 Hz), 8.06 (1H, d, J=7.9 Hz), 9.06 (1H, brs), 10.84 (1H, brs).

Example 54

Synthesis of 3-((2S,4S)-4-{4-[8-(2,2,2-trifluoroethoxy)-2-trifluoromethyl-4-quinolyl]-1-piperazinyl}-2-pyrrolidinylcarbonyl)-1,3-thiazolidine dihydrochloride (1) The product (345 mg) of Example 51(2) was dissolved in DMF (3 mL) and potassium carbonate (164 mg) and methanesulfonic acid 2,2,2-trifluoroethyl ester (212 mg) were added. The mixture was stirred at 100° C. for 5 hr. Water was added to the reaction solution, and the mixture was extracted with chloroform. The extract solution washed with saturated brine, dried and concentrated under reduced pressure. The residue was purified by silica gel column chromatography to give 3-((2S,4S)-1-tert-butoxycarbonyl-4-{4-[8-(2,2,2-trifluoroethoxy)-2-trifluoromethyl-4-quinolyl]-1-piperazinyl}-2-pyrrolidinylcarbonyl)-1,3-thiazolidine (283 mg) as a yellow oil.

(2) In the same manner as in Example 47(5) and using the above-mentioned compound (283 mg), the title compound (19 mg) was obtained as a white powder.

¹H-NMR (DMSO-d₆) δ 2.34 (1H, m), 2.92-4.21 (17H, m) 4.49-4.79 (3H, m), 5.03 (2H, q, J=9.0 Hz), 7.44 (1H, s), 7.51 (1H, d, J=7.5 Hz), 7.68 (1H, dd, J=7.5, 8.4 Hz), 7.78 (1H, d, J=8.4 Hz), 9.16 (1H, brs), 10.84 (1H, brs).

Example 55

Synthesis of 3-{(2S,4S)-4-[4-(2-trifluoromethyl-6,8-dimethoxy-4-quinolyl)-1-piperazinyl]-2-pyrrolidinylcarbonyl}-1,3-thiazolidine dihydrochloride (1) 2,4-Dimethoxyaniline (30 g) was dissolved in benzene (400 mL), and ethyl trifluoroacetoacetate (34 mL) and p-toluenesulfonic acid monohydrate (3.7 g) were added. The mixture was refluxed for 21 hr. The reaction solution was concentrated under reduced pressure, and a saturated a aqueous sodium hydrogen carbonate solution was added to the residue. The mixture was extracted with ethyl acetate. The extract solution washed with saturated brine, dried and concentrated under reduced pressure. 75% Polyphosphoric acid (150 mL) was added to the residue and the mixture was stirred at 130° C. for 2 hr. The reaction solution was poured onto ice, and the mixture was extracted with ethyl acetate. The extract solution washed successively with a saturated a aqueous sodium hydrogen carbonate solution, 1 mol/L hydrochloric acid and saturated brine, dried and concentrated under reduced pressure. Ethanol was added to the residue and the precipitate was filtered off. The filtrate was concentrated under reduced pressure to give 2-trifluoromethyl-4-hydroxy-6,8-dimethoxyquinoline (12 g) as an oil.

(2) In the same manner as in Example 46(2) and using the above-mentioned compound (12 g) and phosphorus oxychloride (17 mL), 4-chloro-2-trifluoromethyl-6,8-dimethoxyquinoline (13 g) was obtained as a white solid.

(3) In the same manner as in Example 46(3) and using the above-mentioned compound (13 g) and piperazine (23 g), 1-(2-trifluoromethyl-6,8-dimethoxy-4-quinolyl)piperazine (13 g) was obtained as a pale-brown solid.

(4) In the same manner as in Example 29(1) and using the above-mentioned compound (1.2 g) and the title compound (0.900 g) of Reference Example 3, 3-{(2S,4S)-1-tert-butoxycarbonyl-4-[4-(2-trifluoromethyl-6,8-dimethoxy-4-quinolyl)-1-piperazinyl]-2-pyrrolidinylcarbonyl}-1,3-thiazolidine (2.1 g) was obtained as a white powder.

(5) In the same manner as in Example 38(4) and using the above-mentioned compound (1.8 g), the title compound (1.4 g) was obtained as a pale-yellow powder.

¹H-NMR (DMSO-d₆) δ 2.25-2.43 (1H, m), 2.97-3.18 (3H, m), 3.25-4.20 (20H, m), 4.48-4.70 (3H, m), 6.84 (1H, d, J=2.4 Hz), 6.95 (1H, d, J=2.4 Hz), 7.38 (1H, s), 9.14 (1H, brs), 10.70 (1H, brs).

Example 56

Synthesis of 3-{(2S,4S)-4-[4-(3,5-dimethyl-1-pyrazolyl)piperidino]-2-pyrrolidinylcarbonyl}-1,3-thiazolidine trihydrochloride (1) tert-Butyl carbazate (26.4 g) was dissolved in ethanol (100 mL) and a solution of 1-ethoxycarbonyl-4-piperidone (34.2 g) in ethanol (80 mL) was added. The mixture was stirred one day. 5% Platinum carbon (2 g) was added, and the mixture was stirred at room temperature under 1 atm hydrogen. Platinum carbon was filtered off and a 4 mol/L hydrochloric acid-dioxane solution (200 mL) was added to the filtrate. The mixture was warmed to 50° C. The solution was cooled with ice and the precipitate was collected by filtration to give 1-ethoxycarbonyl-4-hydrazinopiperidine dihydrochloride (44.4 g) as white crystals.

(2) The above-mentioned compound (2.9 g) was dissolved in methanol (10 mL), and triethylamine (3.1 mL) and acetylacetone (1.1 g) were added. The mixture was stirred at room temperature. The reaction solution was concentrated under reduced pressure, and saturated brine was added. The mixture was extracted with ethyl acetate. The extract solution was washed successively with a 10% a aqueous citric acid solution, a saturated a aqueous sodium hydrogen carbonate solution and saturated brine, dried and concentrated under reduced pressure to give 1-ethoxycarbonyl-4-(3,5-dimethyl-1-pyrazolyl)piperidine (2.69 g) as an oil.

(3) The above-mentioned compound (2.6 g) was dissolved in 30% hydrogen bromide-acetic acid (25 mL) and the mixture was stirred at room temperature for 3 days. The reaction solution was concentrated under reduced pressure, neutralized with an a aqueous potassium carbonate solution and extracted with ethyl acetate. The extract solution was dried over potassium carbonate and concentrated under reduced pressure to give 4-(3,5-dimethyl-1-pyrazolyl)piperidine (1.12 g) as an oil.

(4) In the same manner as in Example 29(1) and using the above-mentioned compound (592 mg) and the title compound (901 mg) of Reference Example 3, 3-{(2S,4S)-1-tert-butoxycarbonyl-4-[4-(3,5-dimethyl-1-pyrazolyl)piperidino]-2-pyrrolidinylcarbonyl}-1,3-thiazolidine (834 mg) was obtained as a white solid.

(5) The above-mentioned compound (834 mg) was dissolved in methanol (20 mL) and chloroform (10 mL), and a 4 mol/L hydrochloric acid-ethyl acetate solution (10 mL) was added. The mixture was stirred for 18 hr. The reaction solution was concentrated under reduced pressure to give the title compound (415 mg) as a white solid.

$^1$H-NMR (DMSO-d$_6$) δ 1.90-2.55 (11H, m), 2.90-4.00 (10H, m), 4.24-4.80 (4H, m), 5.81 (1H, m), 9.12 (1H, brs), 10.89 (1H, brs).

Example 57

Synthesis of 3-{(2S,4S)-4-[4-(3-methyl-5-phenyl-1-pyrazolyl)piperidino]-2-pyrrolidinylcarbonyl}-1,3-thiazolidine trihydrochloride (1) The product (5.2 g) of Example 56(1) was dissolved in methanol (25 mL) and triethylamine (5.6 mL) and dibenzoylacetone (3.2 g) were added. The mixture was stirred at room temperature for 3 days. The reaction solution was concentrated under reduced pressure and saturated brine was added. The mixture was extracted with ethyl acetate. The extract solution washed successively with a 10% a aqueous citric acid solution, a saturated a aqueous sodium hydrogen carbonate solution and saturated brine, dried and concentrated under reduced pressure. The residue was purified by silica gel chromatography to give 1-ethoxycarbonyl-4-(3-methyl-5-phenyl-1-pyrazolyl)piperidine (3.74 g).

(2) In the same manner as in Example 56(3) and using the above-mentioned compound (3.1 g), 4-(3-methyl-5-phenyl-1-pyrazolyl)piperidine was obtained as crystals.

(3) In the same manner as in Example 29(1) and using the above-mentioned compound (0.796 g) and the title compound (0.901 g) of Reference Example 3, 3-{(2S,4S)-1-tert-butoxycarbonyl-4-[4-(3-methyl-5-phenyl-1-pyrazolyl)piperidino]-2-pyrrolidinylcarbonyl}-1,3-hiazolidine(1.43 g) was obtained as a white solid.

(4) In the same manner as in Example 31(4) and using the above-mentioned compound (1.42 g), the title compound (1.17 g) was obtained as a pale-yellow powder.

$^1$H-NMR (DMSO-d$_6$) δ 1.95-2.12 (2H, m), 2.20 (3H, s), 2.22-2.37 (1H, m), 2.87-3.27 (5H, m), 3.38-4.05 (9H, m), 4.33-4.76 (4H, m), 6.13 (1H, s), 7.42-7.57 (5H, m), 9.09 (1H, brs), 10.79 (1H, brs), 11.79 (1H, brs).

Example 58

Synthesis of 3-{(2S,4S)-4-[4-(3,5-diphenyl-1-pyrazolyl)piperidin-1-yl]-2-pyrrolidinylcarbonyl}-1,3-thiazolidine dihydrochloride (1) The product (2.6 g) of Example 56(1) was dissolved in methanol (10 mL) and triethylamine (2.8 mL) and dibenzoylmethane (2.2 g) were added. The mixture was stirred at 60° C. one day. The reaction solution was concentrated under reduced pressure and water was added. The precipitated crystals were collected by filtration to give 1-ethoxycarbonyl-4-(3,5-diphenyl-1-pyrazolyl)piperidine (2.71 g) as crystals.

(2) In the same manner as in Example 56(3) and using the above-mentioned compound (2.7 g), 4-(3,5-diphenyl-1-pyrazolyl)piperidine (2.14 g) was obtained as crystals.

(3) In the same manner as in Example 29(1) and using the above-mentioned compound (1.00 g) and the title compound (0.901 g) of Reference Example 3, 3-{(2S,4S)-1-tert-butoxycarbonyl-4-[4-(3,5-diphenyl-1-pyrazolyl)piperidino]-2-pyrrolidinylcarbonyl}-1,3-thiazolidine (1.12 g) was obtained as a colorless transparent oil.

(4) The above-mentioned compound (1.12 g) was dissolved in methanol (20 mL) and chloroform (10 mL), and a 4 mol/L hydrochloric acid-ethyl acetate solution (10 mL) was added. The mixture was stirred for 18 hr. The reaction solution was concentrated under reduced pressure to give the title compound (0.804 g) as a white solid.

$^1$H-NMR (DMSO-d$_6$) δ 2.00-2.70 (5H, m), 2.82-4.10 (12H, m), 4.37-4.80 (4H, m), 6.85 (1H, s), 7.25-7.63 (8H, m), 7.74-7.95 (2H, m)

Example 59

Synthesis of 3-{(2S,4S)-4-[4-(3-trifluoromethyl-1-phenyl-5-pyrazolyl)piperidino]-2-pyrrolidinylcarbonyl}-1,3-thiazolidine dihydrochloride (1) Ethyl trifluoroacetate (6.32 g) was dissolved in tert-butyl methyl ether (10 mL) and a 28% sodium methoxide-methanol solution (9.40 g) and a solution of 4-acetylpyridine (4.90 g) in tert-butyl methyl ether (20 mL) were added successively at room temperature. The mixture was stirred for 22 hr. A 10% a aqueous citric acid solution was added until the reaction solution became about pH 4, and the precipitate was collected by filtration, washed with water and dried to give 4-trifluoroacetoacetylpyridine (5.46 g) as a yellow solid.

(2) The above-mentioned compound (760 mg) was suspended in ethanol (20 mL), and phenylhydrazine (0.380 mL) was added at room temperature. The mixture was stirred for 23 hr. The reaction mixture was concentrated under reduced pressure, and water was added to the residue. The mixture was extracted with ethyl acetate. The extract solution washed with saturated brine, dried and concentrated under reduced pressure. The residue was purified by silica gel chromatography to give 4-(3-trifluoromethyl-1-phenyl-5-pyrazolyl)pyridine (470 mg) as an oil.

(3) The above-mentioned compound (470 mg) was dissolved in acetonitrile (50 mL), and benzyl chloride (0.380 mL) was added. The mixture was heated under reflux for 24 hr. The reaction solution was concentrated under reduced pressure, and diethyl ether was added to the residue. The precipitate was collected by filtration. This was dissolved in ethanol (30 mL) and sodium borohydride (130 mg) was added under ice-cooling. The mixture was stirred at room temperature for 22 hr. Water was added to the reaction solution, and the mixture was extracted with ethyl acetate. The extract solution washed with saturated brine, dried and concentrated under reduced pressure. The residue was purified by silica gel chromatography to give 1-benzyl-4-(3-trifluoromethyl-1-phenyl-5-pyrazolyl)-1,2,3,6-tetrahydropyridine (142 mg) as an oil.

(4) The above-mentioned compound (142 mg) and ammonium formate (240 mg) were dissolved in methanol (20 mL) and 10% palladium/carbon (150 mg) was added. The mixture was heated under reflux under a nitrogen atmosphere for 2 hr. The insoluble materials were filtered off and the filtrate was concentrated under reduced pressure. A saturated aqueous sodium hydrogen carbonate solution was added to the residue and the mixture was extracted with chloroform. The extract solution was dried and concentrated under reduced pressure to give 4-(3-trifluoromethyl-1-phenyl-5-pyrazolyl)piperidine (90 mg) as an oil.

(5) In the same manner as in Example 29(1) and using the above-mentioned compound (90 mg) and the title compound (90 mg) of Reference Example 3, 3-{(2S,4S)-1-tert-butoxycarbonyl-4-[4-(3-trifluoromethyl -1-phenyl-5-pyrazolyl)piperidino]-2-pyrrolidinylcarbonyl}-1,3-thiazolidine (134 mg) was obtained as a white powder.

(6) In the same manner as in Example 33(5) and using the above-mentioned compound (134 mg), the title compound (96 mg) was obtained as a white solid.

$^1$H-NMR (500 MHz, DMSO-$d_6$) δ 1.90-2.30 (5H, m), 2.83-4.00 (13H, m), 4.46-4.71 (3H, m), 6.78 (1H, s), 7.57-7.62 (5H, m), 9.07 (1H, brs), 10.45 (1H, brs), 11.82 (1H, brs).

Example 60

Synthesis of 3-{(2S,4S)-4-[4-(1-phenyl-1H-tetrazol -5-yl)piperidino]-2-pyrrolidinylcarbonyl}-1,3-thiazolidine dihydrochloride (1) 1-Benzyloxycarbonylisonipecotic acid (13.1 g), HOBT (11.4 g) and EDC hydrochloride (11.4 g) were dissolved in tetrahydrofuran (200 mL) and aniline (5.0 mL) was added. The mixture was stirred at room temperature for 17 hr. The reaction solution was concentrated under reduced pressure and 0.5 mol/L hydrochloric acid was added. The mixture was extracted with ethyl acetate. The extract solution was washed successively with a saturated a aqueous sodium hydrogen carbonate solution and saturated brine and dried. The solvent was evaporated under reduced pressure to give 1-benzyloxycarbonylisonipecotic acid anilide (17.0 g) as a white solid.

(2) The above-mentioned compound (2.00 g), triphenylphosphine (3.10 g) and a 40% diisopropyl azodicarboxylate-toluene solution (6.00 g) were dissolved in tetrahydrofuran (50 mL) and trimethylsilylazide (1.57 mL) was added under ice-cooling. The mixture was stirred at room temperature for 5 days. The reaction solution was concentrated under reduced pressure and the residue was purified by silica gel chromatography to give 1-benzyloxycarbonyl-4-(1-phenyl-1H-tetrazol-5-yl)piperidine (4.09 g) as a brown oil.

(3) The above-mentioned compound (4.09 g) was dissolved in methanol (50 mL) and the mixture was stirred in the presence of 10% palladium/carbon (420 mg) under 1 atm hydrogen at room temperature. The reaction solution was filtered, and the filtrate was concentrated under reduced pressure to give 4-(1-phenyl-1H-tetrazol-5-yl)piperidine (1.42 g) as a gray solid.

(4) In the same manner as in Example 29(1) and using the above-mentioned compound (0.757 g) and the title compound (0.901 g) of Reference Example 3, 3-{(2S,4S)-1-tert-butoxycarbonyl-4-[4-(1-phenyl-1H-tetrazol-5-yl)piperidino]-2-pyrrolidinylcarbonyl}-1,3-thiazolidine (1.07 g) was obtained as a white solid.

(5) The above-mentioned compound (1.06 g) was dissolved in ethanol (4 mL) and a 7.4 mol/L hydrochloric acid-ethanol solution (3 mL) was added. The mixture was stirred at room temperature for 11 hr. The precipitate was collected by filtration to give the title compound (0.688 g) as a white powder.

$^1$H-NMR (DMSO-$d_6$) δ 1.93-2.34 (5H, m), 2.85-3.95 (13H, m), 4.43-4.77 (3H, m), 7.69 (5H, s), 9.12 (1H, brs), 10.74 (1H, brs), 12.04 (1H, brs).

Example 61

Synthesis of 3-((2S,4S)-4-{4-[1-(4-fluorophenyl)-1H-tetrazol-5-yl]piperidino}-2-pyrrolidinylcarbonyl)-1,3-thiazolidine dihydrochloride (1) Isonipecotic acid (19.0 g) was dissolved in water (150 mL) and 1,4-dioxane (300 mL), and a 1 mol/L a aqueous sodium hydroxide solution (150 mL) and di-tert-butyl dicarbonate (35.3 g) were added under ice-cooling. The mixture was stirred at room temperature for 3 days. 1,4-Dioxane was evaporated under reduced pressure and a 5% aqueous potassium hydrogen sulfate solution was added to the residue. The precipitated solid was collected by filtration to give 1-tert-butoxycarbonylisonipecotic acid (33.0 g) as a white solid.

(2) The above-mentioned compound (2.43 g), HOBT (1.95 g) and EDC hydrochloride (2.44 g) were dissolved in DMF (50 mL) and 4-fluoroaniline (1.00 mL) was added. The mixture was stirred at room temperature for 5 hr. Water was added to the reaction solution, and the precipitate was collected by filtration to give 4-fluorophenylamide 1-tert-butoxycarbonyl-isonipecotate (2.82 g) as a white solid.

(3) In the same manner as in Example 60(2) and using the above-mentioned compound (2.82 g), 1-tert-butoxycarbonyl-4-[1-(4-fluorophenyl)-1H-tetrazol-5-yl]piperidine (0.916 g) was obtained as a white solid.

(4) In the same manner as in Example 36(2) and using the above-mentioned compound (916 mg), 4-[1-(4-fluorophenyl)-1H-tetrazol-5-yl]piperidine (342 mg) was obtained as a pale-brown solid.

(5) In the same manner as in Example 29(1) and using the above-mentioned compound (338 mg) and the title compound (373 mg) of Reference Example 3, 3-((2S,4S)-1-tert-butoxycarbonyl-4-{4-[1-(4-fluorophenyl) -1H-tetrazol-5-yl]piperidino}-2-pyrrolidinylcarbonyl)-1,3-thiazolidine (514 mg) was obtained as a white powder.

(6) The above-mentioned compound (512 mg) was dissolved in methanol (10 mL) and chloroform (5 mL). 4 mol/L Hydrochloric acid-dioxane (3 mL) was added at room temperature and the mixture was stirred for 17 hr. The reaction solution was concentrated under reduced pressure and the residue was dissolved in methanol. Ethyl acetate was added and the precipitate was collected by filtration to give the title compound (318 mg) as a white solid.

$^1$H-NMR (500 MHz, DMSO-$d_6$) δ 1.90-2.40 (5H, m), 2.70-3.95 (13H, m) 4.46-4.72 (3H, m), 7.52-7.55 (2H, m), 7.77-7.79 (2H, m), 9.09 (1H, brs), 10.57 (1H, brs), 11.92 (1H, brs).

Example 62

Synthesis of 3-{(2S,4S)-4-[4-(1H-indazol-1-yl)piperidino]-2-pyrrolidinylcarbonyl}-1,3-thiazolidine dihydrochloride (1) 2-Fluorobenzaldehyde (2.48 g) was dissolved in methanol (20 mL) and the product (8.2 g) of Example 56(1) and a solution of triethylamine (7.5 mL) in methanol (20 mL) were added dropwise. After stirring at room temperature for 1 hr, the mixture was concentrated under reduced pressure, and saturated brine was added to the residue. The mixture was extracted with ethyl acetate. The extract solution washed successively with a 10% aqueous citric acid solution, a saturated a aqueous sodium hydrogen carbonate solution and saturated brine and dried. The solvent was evaporated and copper (I) iodide (0.38 g) and tetrahydrofuran (40 mL) were added to the residue. Furthermore, a solution of potassium tert-butoxide (3.8 g) in tetrahydrofuran (20 mL) was added under ice-cooling. The mixture was stirred at room temperature for 4 days. The reaction solution was neutralized with a 10% aqueous citric acid solution (20 mL) and extracted with ethyl acetate. The extract solution washed successively with saturated brine, a saturated a aqueous sodium hydrogen carbonate solution and saturated brine, dried and concentrated under reduced pressure. The residue was purified by silica gel chromatography to give 1-ethoxycarbonyl-4-(1H-indazol-1-yl)piperidine (1.04 g) as an oil.

(2) The above-mentioned compound (0.90 g) was dissolved in 30% hydrogen bromide-acetic acid (10 mL) and the mixture was stirred at room temperature for 4 days. The reaction solution was concentrated under reduced pressure, and the residue was neutralized with a aqueous potassium carbonate. The mixture was extracted with ethyl acetate and the extract solution was dried and concentrated under reduced pressure. The residue was purified by silica gel chromatography to give 4-(1H-indazol-1-yl)piperidine (0.42 g) as an oil.

(3) In the same manner as in Example 29(1) and using the above-mentioned compound (420 mg) and the title compound (570 mg) of Reference Example 3, 3-{(2S,4S)-1-tert-butoxycarbonyl-4-[4-(1H-indazol-1-yl)piperidino]-2-pyrrolidinylcarbonyl}-1,3-thiazolidine (468 mg) was obtained as a colorless transparent oil.

(4) The above-mentioned compound (468 mg) was dissolved in methanol (10 mL) and chloroform (5 mL), and a 4 mol/L hydrochloric acid-ethyl acetate solution (5 mL) was added. The mixture was stirred for 18 hr. The reaction solution was concentrated under reduced pressure to give the title compound (283 mg) as a white solid.

$^1$H-NMR (DMSO-$d_6$) δ 2.00-2.70 (5H, m), 2.90-4.15 (12H, m), 4.42-4.80 (3H, m), 4.90-5.20 (1H, m), 7.17 (1H, t, J=7.4 Hz), 7.42 (1H, t, J=7.3 Hz), 7.67-7.85 (2H, m), 8.12 (1H, s).

Example 63

Synthesis of 3-{(2S,4S)-4-[4-(3-methyl-1H-indazol-1-yl) piperidino]-2-pyrrolidinylcarbonyl}-1,3-thiazolidine dihydrochloride (1) The product (8.4 g) of Example 56(1) was dissolved in methanol (35 mL) and triethylamine (9.5 mL) and 2'-fluoroacetophenone (4.05 g) were added. The mixture was heated under reflux for 1 hr. The reaction solution was concentrated under reduced pressure, and saturated brine was added to the residue. The mixture was extracted with ethyl acetate. The extract solution washed successively with a 10% a aqueous citric acid solution, a saturated a aqueous sodium hydrogen carbonate solution and saturated brine and dried. The solvent was evaporated. Copper (I) iodide (0.6 g) and tetrahydrofuran (80 mL) were added to the residue and potassium tert-butoxide (6 g) was further added under ice-cooling. The mixture was stirred at room temperature for 5 days. The reaction solution was neutralized with a 10% a aqueous citric acid solution (40 mL) and the mixture was extracted with ethyl acetate. The extract solution washed with saturated brine, a saturated a aqueous sodium hydrogen carbonate solution and saturated brine, dried and concentrated under reduced pressure. The residue was purified by silica gel chromatography to give 1-ethoxycarbonyl-4-(3-methyl-1H-indazol-1-yl)piperidine as an oil.

(2) In the same manner as in Example 56(3) and using the above-mentioned compound (2.3 g), 4-(3-methyl-1H-indazol-1-yl)piperidine (1.1 g) was obtained as an oil.

(3) In the same manner as in Example 29(1) and using the above-mentioned compound (710 mg) and the title compound (901 mg) of Reference Example 3, 3-{(2S,4S)-1-tert-butoxycarbonyl-4-[4-(3-methyl-1H-indazol-1-yl)piperidin-1-yl]-2-pyrrolidinylcarbonyl}-1,3-thiazolidine (793 mg) was obtained as a white solid.

(4) In the same manner as in Example 62(4) and using the above-mentioned compound (793 mg), the title compound (580 mg) was obtained as a white solid.

$^1$H-NMR (DMSO-$d_6$) δ 2.00-2.70 (8H, m), 2.92-4.27 (12H, m), 4.38-4.80 (3H, m), 4.80-5.12 (1H, m), 7.13 (1H, t, J=7.2 Hz), 7.40 (1H, t, J=7.5 Hz), 7.56-7.81 (2H, m), 9.15 (1H, brs), 10.80 (1H, brs), 12.14 (1H, brs).

Example 64

Synthesis of 3-{(2S,4S)-4-[4-(5-trifluoromethyl-1-benzimidazolyl)piperidino]-2-pyrrolidinylcarbonyl}-1,3-thiazolidine trihydrochloride (1) 1-Fluoro-4-trifluoromethyl-2-nitrobenzene (5.1 g) was dissolved in tetrahydrofuran (100 mL) and diisopropylethylamine (5.5 ml) and 4-amino-1-tert-butoxycarbonylpiperidine (5.37 g) were added. The mixture was stirred at room temperature for 3 hr. The reaction solution was concentrated under reduced pressure, and water was added to the residue. The mixture was extracted with ethyl acetate and the extract solution was dried and concentrated under reduced pressure to give 1-tert-butoxycarbonyl-4-(4-trifluoromethyl-2-nitrophenyl)aminopiperidine.

(2) The above-mentioned compound was dissolved in ethanol (350 mL) and anhydrous tin(II) chloride (61 g) was added. The mixture was stirred for 3 days. A saturated a aqueous sodium hydrogen carbonate solution was added to the reaction solution and the precipitated insoluble materials were filtered off.

The filtrate was concentrated under reduced pressure. A saturated a aqueous sodium hydrogen carbonate solution was added to the residue and the mixture was extracted with ethyl acetate. The extract solution was dried and concentrated under reduced pressure. The residue was purified by silica gel chromatography to give 4-(2-amino-4-trifluoromethylphenyl)amino-1-tert-butoxycarbonylpiperidine (3.58 g).

(3) Trimethyl orthoformate (12 mL) and p-toluenesulfonic acid (0.010 g) were added to the above-mentioned compound (1.5 g) and the mixture was stirred at 90° C. for 90 min. The reaction solution was concentrated under reduced pressure to give 1-tert-butoxycarbonyl-4-(5-trifluoromethyl-1-benzimidazolyl)piperidine.

(4) The above-mentioned compound was dissolved in trifluoroacetic acid (10 mL) and the mixture was stirred at room temperature for 30 min. The reaction solution was concentrated under reduced pressure, and a saturated a aqueous sodium hydrogen carbonate solution was added to the residue. The mixture was extracted with ethyl acetate and the extract solution was dried and concentrated under reduced pressure. The residue was crystallized from diethyl ether to give 4-(5-trifluoromethyl-1-benzimidazolyl)piperidine (960 mg).

(5) In the same manner as in Example 29(1) and using the above-mentioned compound (646 mg) and the title compound (601 mg) of Reference Example 3, 3-{(2S,4S)-1-tert-butoxycarbonyl-4-[4-(5-trifluoromethyl -1-benzimidazolyl)piperidino]-2-pyrrolidinylcarbonyl}-1,3-thiazolidine (795 mg) was obtained as a white solid.

(6) In the same manner as in Example 60(5) and using the above-mentioned compound (791 mg), the title compound (558 mg) was obtained as a white powder.

$^1$H-NMR (DMSO-d$_6$) δ 2.25-2.43 (3H, m), 2.60-2.78 (2H, m), 2.98-3.21 (3H, m), 3.27-4.15 (9H, m), 4.47-4.80 (3H, m), 4.91-5.07 (1H, m), 7.75 (1H, d, J=8.6 Hz), 8.14 (1H, s), 8.28 (1H, d, J=8.6 Hz), 8.96 (1H, s), 9.21 (1H, brs), 10.87 (1H, brs), 12.51 (1H, brs).

Example 65

Synthesis of 3-{(2S,4S)-4-[4-(5-trifluoromethyl-2-methyl-1-benzimidazolyl)piperidino]-2-pyrrolidinylcarbonyl}-1,3-thiazolidine trihydrochloride (1) The product (1.9 g) of Example 64 (2) was dissolved in dichloromethane (15 mL) and acetic anhydride (0.500 mL) was added. The mixture was stirred overnight. The reaction solution was concentrated under reduced pressure to give 4-(2-acetylamino-4-trifluoromethylphenyl)amino-1-tert-butoxycarbonylpiperidine.

(2) The above-mentioned compound was dissolved in acetic acid (15 mL) and the mixture was stirred at 80° C. overnight. The reaction solution was concentrated under reduced pressure, and a saturated a aqueous sodium hydrogen carbonate solution was added to the residue. The mixture was extracted with ethyl acetate and the extract solution was dried and concentrated under reduced pressure. The residue was purified by ISOLUTE FLUSH SIL to give 1-tert-butoxycarbonyl-4-(5-trifluoromethyl-2-methyl-1-benzimidazolyl)piperidine.

(3) The above-mentioned compound was dissolved in trifluoroacetic acid (20 mL) and left standing for 4 hr. The reaction solution was concentrated under reduced pressure, and a saturated a aqueous sodium hydrogen carbonate solution was added to the residue. The mixture was extracted with ethyl acetate and the extract solution was dried and concentrated under reduced pressure. The residue was crystallized from ethyl acetate-hexane to give 4-(5-trifluoromethyl-2-methyl-1-benzimidazolyl)piperidine (730 mg).

(4) In the same manner as in Example 29(1) and using the above-mentioned compound (614 mg) and the title compound (601 mg) of Reference Example 3, 3-{(2S,4S)-1-tert-butoxycarbonyl-4-[4-(5-trifluoromethyl-2-methyl-1-benzimidazolyl)piperidino]-2-pyrrolidinylcarbonyl}-1,3-thiazolidine (902 mg) was obtained as a white solid.

(5) In the same manner as in Example 31(4) and using the above-mentioned compound (898 mg), the title compound (818 mg) was obtained as a white powder.

$^1$H-NMR (DMSO-d$_6$) δ 2.20-2.40 (3H, m), 2.87 (3H, s), 2.91-3.20 (5H, m), 3.25-4.20 (9H, m), 4.48-4.79 (3H, m), 4.95-5.09 (1H, m), 7.73 (1H, d, J=8.6 Hz), 8.11 (1H, s), 8.62 (1H, d, J=8.6 Hz), 9.23 (1H, brs), 10.90 (1H, brs), 12.75 (1H, brs).

Example 66

Synthesis of 3-{(2S,4S)-4-[4-(6-fluoro-2-benzoxazolyl)piperidino]-2-pyrrolidinylcarbonyl}-1,3-thiazolidine (1) To a mixed solution of ethanol (76 g) and chloroform (110 mL) was added dropwise acetyl chloride (107 mL) under ice-cooling. After stirring for 30 min, a solution of 1-benzyloxycarbonyl-4-cyanopiperidine (12.2 g) in chloroform1 (10 mL) was added under ice-cooling. The mixture was stirred at room temperature for 1 hr. The reaction solution was concentrated under reduced pressure to give 1-benzyloxycarbonyl-4-(ethoxycarbimidyl)piperidine hydrochloride (15.4 g) as a white solid.

(2) The above-mentioned compound (3.07 g) and 2-amino-5-fluorophenol (1.64 g) were dissolved in ethanol (60 mL) and the mixture was heated under reflux for 10 hr. The reaction solution was concentrated under reduced pressure, and 1.0 mol/L hydrochloric acid was added to the residue. The mixture was extracted with ethyl acetate. The extract solution was washed successively with a saturated a aqueous sodium hydrogen carbonate solution and saturated brine and dried. The solvent was evaporated under reduced pressure. The residue was purified by silica gel chromatography to give 1-benzyloxycarbonyl-4-(6-fluoro-2-benzoxazolyl)piperidine (2.51 g) as a brown solid.

(3) In the same manner as in Example 33(3) and using the above-mentioned compound (2.50 g), 4-(6-fluoro-2-benzoxazolyl)piperidine (1.46 g) was obtained as a brown solid.

(4) In the same manner as in Example 29(1) and using the above-mentioned compound (529 mg) and the title compound (601 mg) of Reference Example 3, 3-{(2S,4S)-1-tert-butoxycarbonyl-4-[4-(6-fluoro -2-benzoxazolyl)piperidino]-2-pyrrolidinylcarbonyl}-1,3-thiazolidine (879 mg) was obtained as a white solid.

(5) The above-mentioned compound (874 mg) was dissolved in ethanol (3 mL) in a 7.4 mol/L hydrochloric acid-ethanol solution (1.5 mL) and the mixture was stirred at room temperature for 14 hr. The reaction solution was concentrated under reduced pressure, and a saturated a aqueous sodium hydrogen carbonate solution was added to the residue. The mixture was extracted with chloroform and the extract solution was dried and concentrated under reduced pressure. The residue was purified by silica gel chromatography and crystallized from diethyl ether to give the title compound (213 mg) as a white powder.

$^1$H-NMR (DMSO-d$_6$) δ 1.52-1.63 (1H, m), 1.70-1.87 (2H, m), 2.02-2.23 (4H, m), 2.25-2.36 (1H, m), 2.68-3.12 (8H, m), 3.57-3.98 (3H, m), 4.40-4.71 (2H, m), 7.71-7.27 (1H, m), 7.66-7.76 (2H, m).

Example 67

Synthesis of 3-{(2S,4S)-4-[4-(6-methoxy-2-benzoxazoly)piperidino]-2-pyrrolidinylcarbony}-1,3-thiazolidine trihydrochloride (1) In the same manner as in Example 66(2) and using the product (1.54 g) of Example 66(1) and 2-amino-5-methoxyphenol (1.01 g), 1-benzyloxycarbonyl-4-(6-methoxy-2-benzoxazolyl)piperidine (1.61 g) was obtained as a brown oil.

(2) In the same manner as in Example 33(3) and using the above-mentioned compound (1.60 g), 4-(6-methoxy-2-benzoxazolyl)piperidine (0.951 g) was obtained as a red-brown solid.

(3) In the same manner as in Example 29(1) and using the above-mentioned compound (557 mg) and the title compound (601 mg) of Reference Example 3, 3-{(2S,4S)-1-tert-butoxycarbonyl-4-[4-(6-methoxy-2-benzoxazolyl)piperidino]-2-pyrrolidinylcarbonyl}-1,3-thiazolidine (885 mg) was obtained as a white solid.

(4) The above-mentioned compound (881 mg) was dissolved in ethyl acetate (2 mL) and a 4 mol/L hydrochloric acid-ethyl acetate solution (4.3 mL) was added. The mixture was stirred at room temperature for 14 hr. The precipitate was collected by filtration to give the title compound (780 mg) as a white solid.

$^1$H-NMR (DMSO-$d_6$) δ 2.10-2.45 (6H, m), 2.91-4.08 (15H, m), 4.45-4.78 (3H, m), 6.96 (1H, dd, J=8.7, 2.3 Hz), 7.34 (1H, d, J=2.3 Hz), 7.59 (1H, d, J=8.7 Hz), 9.13 (1H, brs), 10.72 (1H, brs), 12.08 (1H, brs)

Example 68

Synthesis of 3-((2S,4S)-4-{4-[3-trifluoromethyl-1-(4-methoxyphenyl)-5-pyrazolyl]-1,2,3,6-tetrahydropyridin-1-yl}-2-pyrrolidinylcarbonyl)-1,3-thiazolidine dihydrochloride (1) In the same manner as in Example 59(2) and using compound (1.54 g) of Example 59(1) and 4-methoxyphenylhydrazine hydrochloride (1.36 g) and pyridine (630 μL), 4-[3-trifluoromethyl-1-(4-methoxyphenyl)-5-pyrazolyl]pyridine (2.26 g) was obtained as an oil.

(2) In the same manner as in Example 59 (3) and using the above-mentioned compound (2.26 g) and benzyl chloride (1.63 mL), pyridinium salt was obtained, which was then reduced with sodium borohydride (0.540 g) to give 1-benzyl-4-[3-trifluoromethyl-1-(4-methoxyphenyl)-5-pyrazolyl]-1,2,3,6-tetrahydropyridine (1.79 g) as an oil.

(3) The above-mentioned compound (1.65 g) was dissolved in dichloromethane (40 mL) and 1-chloroethyl carbonate (0.520 mL) was added under ice-cooling. The mixture was stirred at room temperature for 24 hr. The reaction solution was concentrated under reduced pressure, and methanol (30 mL) was added to the residue. The mixture was heated under reflux for 1 hr. The solvent was evaporated under reduced pressure, and a saturated aqueous sodium hydrogen carbonate solution was added to the residue. The mixture was extracted with chloroform. The extract solution washed with saturated brine, dried and concentrated under reduced pressure. The residue was purified by silica gel chromatography to give 4-[3-trifluoromethyl-1-(4-methoxyphenyl)-5-pyrazolyl]-1,2,3,6-tetrahydropyridine (1.10 g) as an oil.

(4) In the same manner as in Example 29(1) and using the above-mentioned compound (1.05 g) and the title compound (0.890 g) of Reference Example 3, 3-((2S,4S)-1-tert-butoxycarbonyl-4-{4-[3-trifluoromethyl-1-(4-methoxyphenyl)-5-pyrazolyl]-1,2,3,6-tetrahydropyridin-1-yl}-2-pyrrolidinylcarbonyl)-1,3-thiazolidine (1.70 g) was obtained as a pale-yellow powder.

(5) In the same manner as in Example 36(4) and using the above-mentioned compound (762 mg), the title compound (648 mg) was obtained as a pale-yellow solid.

$^1$H-NMR (500 MHz, DMSO-$d_6$) δ 2.00-2.65 (2H, m), 2.78-4.10 (13H, m) 3.83 (3H, s), 4.46-4.72 (3H, m), 5.72 (1H, s), 7.03 (1H, s), 7.52-7.55 (2H, m), 7.07 (2H, d, J=8.9 Hz), 7.45 (2H, d, J=8.9 Hz), 9.04 (1H, brs), 10.35 (1H, brs).

The structures of the compounds obtained in the above-mentioned Examples are all shown in Tables 1-9.

TABLE 1

| Ex. No. | Y | n | salt |
|---|---|---|---|
| 1 | 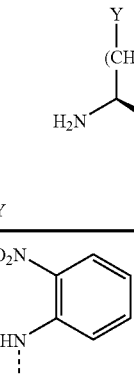 | 4 | CF$_3$CO$_2$H |
| 2 | 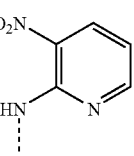 | 4 | CF$_3$CO$_2$H |
| 3 | 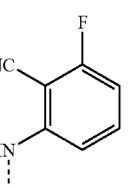 | 4 | CF$_3$CO$_2$H |
| 4 | 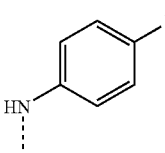 | 4 | — |
| 5 | 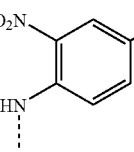 | 4 | — |
| 6 | 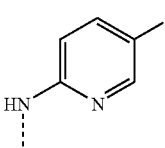 | 4 | 2HCl |
| 7 | 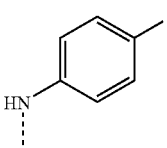 | 4 | — |
| 8 | 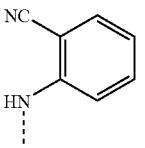 | 4 | — |

TABLE 1-continued
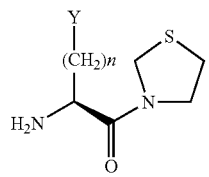
| Ex. No. | Y | n | salt |
|---|---|---|---|
| 9 |  | 4 | — |
TABLE 2
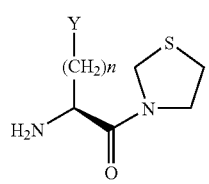
| Ex. No. | Y | n | salt |
|---|---|---|---|
| 10 | 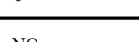 | 4 | — |
| 11 | 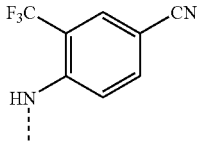 | 4 | — |
| 12 |  | 4 | — |
| 13 | 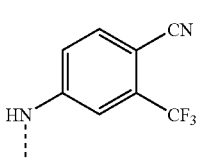 | 4 | — |
| 14 |  | 4 | — |
TABLE 2-continued
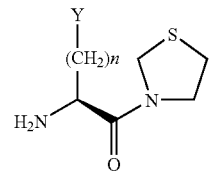
| Ex. No. | Y | n | salt |
|---|---|---|---|
| 15 | | 4 | — |
| 16 | | 4 | — |
| 17 | | 4 | — |
| 18 | | 4 | — |
TABLE 3
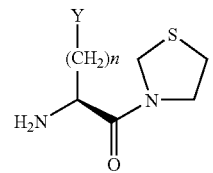
| Ex. No. | Y | n | salt |
|---|---|---|---|
| 19 | | 4 | — |
| 20 | | 4 | — |

TABLE 3-continued

Structure: Y-(CH₂)n-CH(NH₂)-C(=O)-N(thiazolidine)

| Ex. No. | Y | n | salt |
|---|---|---|---|
| 21 | 2-cyano-4-bromo-anilino (NC, Br on benzene with HN-) | 4 | — |
| 22 | 2-cyano-4-trifluoromethyl-anilino (NC, CF₃ on benzene with HN-) | 4 | — |
| 23 | 5-trifluoromethyl-pyridin-2-ylamino (CF₃ on pyridine with HN-) | 4 | — |
| 24 | pyrimidin-2-ylamino (HN-pyrimidine) | 4 | — |
| 25 | 4-trifluoromethyl-pyrimidin-2-ylamino (HN-pyrimidine-CF₃) | 4 | — |
| 26 | 3-cyano-pyridin-2-ylamino (NC, HN- on pyridine) | 4 | — |
| 27 | 2-cyano-4-nitro-anilino (NC, NO₂ on benzene with HN-) | 4 | — |
| 28 | 4-(2-trifluoromethyl-quinolin-4-yl)-piperazin-1-yl (CF₃ on quinoline attached to piperazine) | 4 | — |

TABLE 4

Structure: X-pyrrolidine(NH)-C(=O)-N-pyrrolidine(Y)-Z

| Ex. No. | X | Y | Z | salt |
|---|---|---|---|---|
| 29 | 4-(pyrimidin-2-yl)piperazin-1-yl | S | H | 3HCl |
| 30 | 4-(4-trifluoromethyl-6-phenyl-pyrimidin-2-yl)piperazin-1-yl | S | H | 2HCl |
| 31 | 4-(2-trifluoromethyl-pyrimidin-4-yl)piperazin-1-yl | S | H | 2HCl |
| 32 | 4-[1-(4-methoxyphenyl)-1H-imidazol-2-yl]piperazin-1-yl | S | H | 3HCl |
| 33 | 4-(1-phenyl-1H-pyrazol-5-yl)piperazin-1-yl | S | H | 3HCl |
| 34 | 4-[1-(4-fluorophenyl)-1H-pyrazol-5-yl]piperazin-1-yl | S | H | 3HCl |

TABLE 4-continued

| Ex. No. | X | Y | Z | salt |
|---|---|---|---|---|
| 35 | 5-(4-methylpiperazin-1-yl)-3-methyl-1-(4-fluorophenyl)-1H-pyrazole | S | H | 3HCl |
| 36 | 5-(4-methylpiperazin-1-yl)-3-methyl-1-(2-fluorophenyl)-1H-pyrazole | S | H | 3HCl |

TABLE 5

| Ex. No. | X | Y | Z | salt |
|---|---|---|---|---|
| 37 | 5-(4-methylpiperazin-1-yl)-3-methyl-1-(3-fluorophenyl)-1H-pyrazole | S | H | 3HCl |
| 38 | 5-(4-methylpiperazin-1-yl)-3-methyl-1-(4-chlorophenyl)-1H-pyrazole | S | H | 3HCl |

TABLE 5-continued

| Ex. No. | X | Y | Z | salt |
|---|---|---|---|---|
| 39 | 5-(4-methylpiperazin-1-yl)-3-methyl-1-(4-cyanophenyl)-1H-pyrazole | S | H | 2HCl |
| 40 | 5-(4-methylpiperazin-1-yl)-3-methyl-1-(pyridin-2-yl)-1H-pyrazole | S | H | 2HCl |
| 41 | 5-(4-methylpiperazin-1-yl)-3-methyl-1-(pyridin-3-yl)-1H-pyrazole | S | H | 3 maleic acid |
| 42 | 5-(4-methylpiperazin-1-yl)-3-methyl-1-(pyridin-4-yl)-1H-pyrazole | S | H | 3 maleic acid |
| 43 | 5-(4-methylpiperazin-1-yl)-3-methyl-1-(5-cyanopyridin-2-yl)-1H-pyrazole | S | H | 2HCl |

TABLE 6
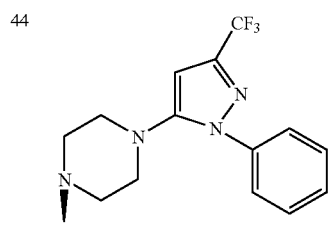
| Ex. No. | X | Y | Z | salt |
|---|---|---|---|---|
| 44 | 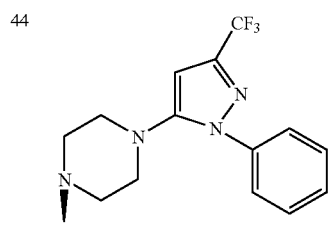 | S | H | 3HCl |
| 45 | 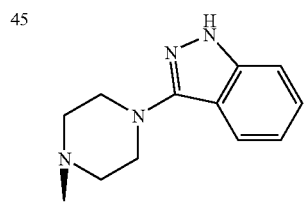 | S | H | 3HCl |
| 46 | 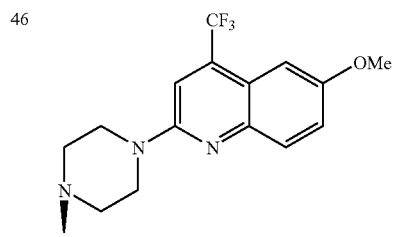 | S | H | 2HCl |
| 47 | 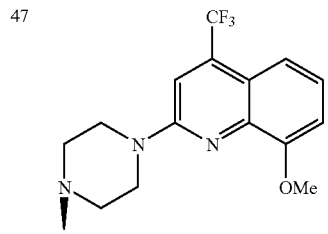 | S | H | 3HCl |
| 48 | 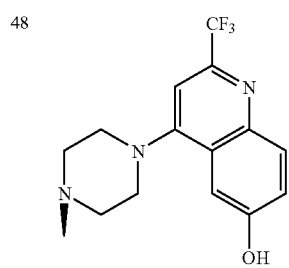 | S | H | 2HCl |
TABLE 6-continued
| Ex. No. | X | Y | Z | salt |
|---|---|---|---|---|
| 49 | 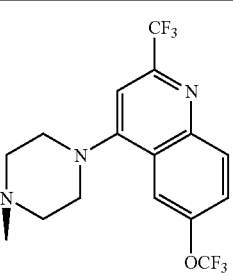 | S | H | 2HCl |
TABLE 7
| Ex. No. | X | Y | Z | salt |
|---|---|---|---|---|
| 50 | 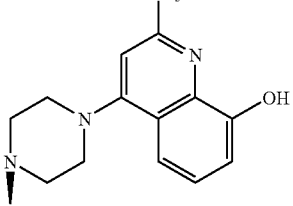 | S | H | 3HCl |
| 51 | 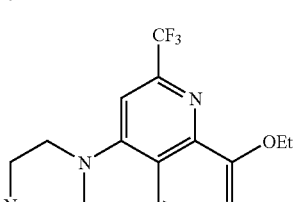 | S | H | 3HCl |
| 52 | 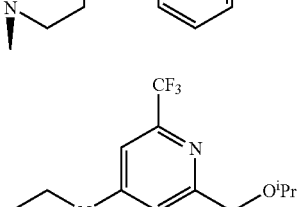 | S | H | 3HCl |

TABLE 7-continued

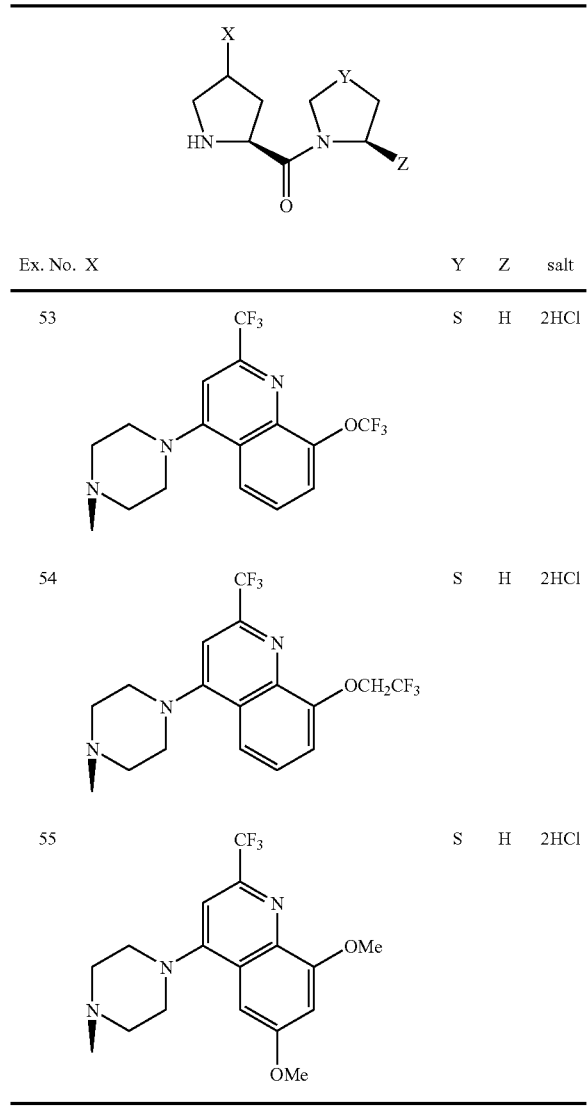

| Ex. No. | X | Y | Z | salt |
|---|---|---|---|---|
| 53 | 4-(piperazin-1-yl)-2-trifluoromethyl-8-trifluoromethoxyquinoline | S | H | 2HCl |
| 54 | 4-(piperazin-1-yl)-2-trifluoromethyl-8-(2,2,2-trifluoroethoxy)quinoline | S | H | 2HCl |
| 55 | 4-(piperazin-1-yl)-2-trifluoromethyl-6,8-dimethoxyquinoline | S | H | 2HCl |

TABLE 8

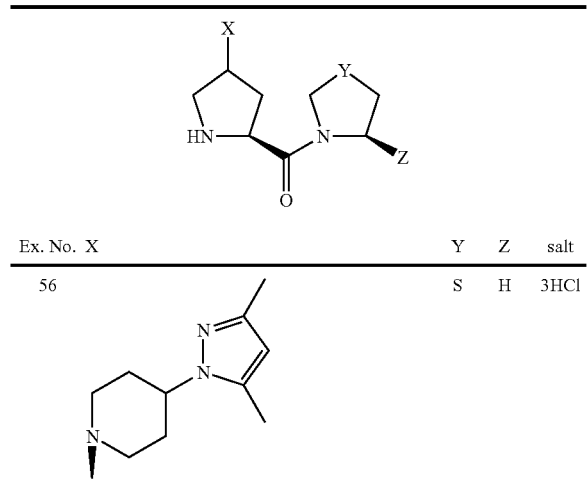

| Ex. No. | X | Y | Z | salt |
|---|---|---|---|---|
| 56 | 1-(3,5-dimethyl-1H-pyrazol-1-yl)piperidin-4-yl | S | H | 3HCl |

TABLE 8-continued

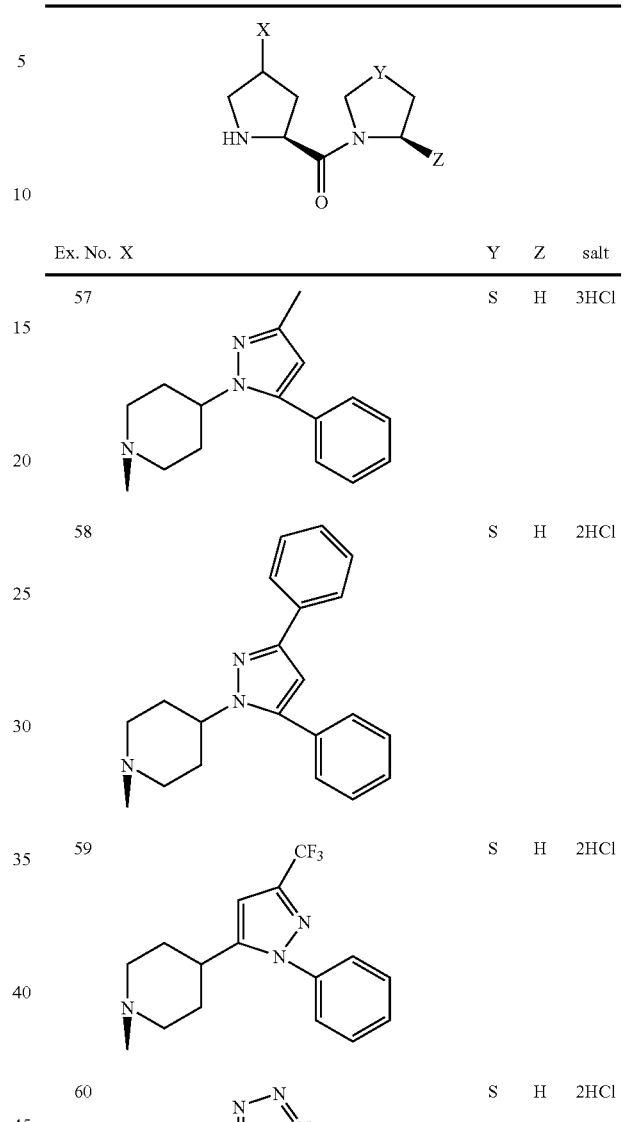

| Ex. No. | X | Y | Z | salt |
|---|---|---|---|---|
| 57 | 1-(3-methyl-5-phenyl-1H-pyrazol-1-yl)piperidin-4-yl | S | H | 3HCl |
| 58 | 1-(3,5-diphenyl-1H-pyrazol-1-yl)piperidin-4-yl | S | H | 2HCl |
| 59 | 1-(3-trifluoromethyl-1-phenyl-1H-pyrazol-5-yl)piperidin-4-yl | S | H | 2HCl |
| 60 | 1-(1-phenyl-1H-tetrazol-5-yl)piperidin-4-yl | S | H | 2HCl |
| 61 | 1-(1-(4-fluorophenyl)-1H-tetrazol-5-yl)piperidin-4-yl | S | H | 2HCl |
| 62 | 1-(1H-indazol-1-yl)piperidin-4-yl | S | H | 2HCl |

TABLE 9

[Core structure: HN-pyrrolidine(X)-C(=O)-N-pyrrolidine(Y,Z)]

| Ex. No. | X | Y | Z | salt |
|---|---|---|---|---|
| 63 | 1-(3-methyl-1H-indazol-1-yl)piperidin-4-yl | S | H | 2HCl |
| 64 | 1-(5-trifluoromethyl-1H-benzimidazol-1-yl)piperidin-4-yl | S | H | 3HCl |
| 65 | 1-(2-methyl-5-trifluoromethyl-1H-benzimidazol-1-yl)piperidin-4-yl | S | H | 3HCl |
| 66 | 1-(6-fluorobenzoxazol-2-yl)piperidin-4-yl | S | H | — |
| 67 | 1-(6-methoxybenzoxazol-2-yl)piperidin-4-yl | S | H | 3HCl |
| 68 | 1-[3-trifluoromethyl-1-(4-methoxyphenyl)-1H-pyrazol-5-yl]-1,2,3,6-tetrahydropyridin-4-yl | S | H | 2HCl |

According to the methods similar to the methods of the above-mentioned Examples, the following compounds can be synthesized.

3-[(S)-2-amino-6-(4-benzenesulfonylphenylamino)hexanoyl]-1,3-thiazolidine, 3-{(S)-2-amino-6-[N-(4-methanesulfonylphenyl)-N-methylamino]hexanoyl}-1,3-thiazolidine, 3-{(S)-2-amino-6-[N-(5-cyanopyridin-2-yl)-N-methylamino]hexanoyl}-1,3-thiazolidine, 3-{(S)-2-amino-6-[N-(5-cyanopyridin-2-yl)-N-benzylamino]hexanoyl-1,3-thiazolidine, 1-[(S)-2-amino-6-(4-methanesulfonylphenylamino)hexanoyl]pyrrolidine, 1-[(S)-2-amino-6-(5-cyanopyridin-2-ylamino)hexanoyl]pyrrolidine, 3-[(S)-2-amino-6-(5,6-dicyanopyridin-2-ylamino)hexanoyl]-1,3-thiazolidine, 3-[(S)-2-amino-6-(3,4-dicyanophenylamino)hexanoyl]-1,3-thiazolidine, 3-{(S)-2-amino-6-[4-(4-nitrophenyl)piperazin-1-yl]hexanoyl}-1,3-thiazolidine, 3-1(S)-2-amino-6-[4-(3,5-dichlorophenyl)piperazin-1-yl]hexanoyl-1,3-thiazolidine, 3-1(S)-2-amino-6-[4-(pyridin-2-yl)piperazin-1-yl]hexanoyl}-1,3-thiazolidine, 3-[(S)-2-amino-6-[4-(pyridin-4-yl)piperazin-1-yl]hexanoyl]-1,3-thiazolidine, 3-{(S)-2-amino-6-[4-(4-cyanopyridin-2-yl)piperazin-1-yl]hexanoyl}-1,3-thiazolidine, 3-{(S)-2-amino-6-[4-(5-cyanopyridin-2-yl)piperazin-1-yl]hexanoyl}-1,3-thiazolidine, 3-{(S)-2-amino-6-[4-(5-nitropyridin-2-yl)piperazin-1-yl]hexanoyl}-1,3-thiazolidine, 3-1(S)-2-amino-6-[4-(5-trifluoromethylpyridin-2-yl)piperazin-1-yl]hexanoyl}-1,3-thiazolidine, 3-{(S)-2-amino-6-[4-(5-carboxypyridin-2-yl)piperazin-1-yl]hexanoyl}-1,3-thiazolidine, 3-((S)-2-amino-6-{4-[5-(ethoxycarbonyl)pyridin-2-yl]piperazin-1-yl}hexanoyl)-1,3-thiazolidine, 3-{(S)-2-amino-6-[4-(5-carbamoylpyridin-2-yl)piperazin-1-yl]hexanoyl}-1,3-thiazolidine, 3-{(S)-2-amino-6-[4-(3,5-dichloropyridin-4-yl)piperazin-1-yl]hexanoyl}-1,3-thiazolidine, 3-{(S)-2-amino-6-[4-(1-phenyl-2-imidazolyl)piperazin-1-yl]hexanoyl}-1,3-thiazolidine, 3-{(S)-2-amino-6-[4-(1-phenyl-5-pyrazolyl)piperazin-1-yl]hexanoyl}-1,3-thiazolidine, 3-1(S)-2-amino-6-[4-(3-methyl-1-phenyl-5-pyrazolyl)piperazin-1-yl]hexanoyl}-1,3-thiazolidine, 3-((S)-2-amino-6-{4-[1-(pyridin-2-yl)-5-pyrazolyl]piperazin-1-yl}hexanoyl)-1,3-thiazolidine, 3-((S)-2-amino-6-{4-[4-(4-cyanophenyl)-2-thiazolyl]piperazin-1-yl}hexanoyl)-1,3-thiazolidine, 3-1(S)-2-amino-6-[4-(1-phenyl-1H-tetrazol-5-yl)piperazin-1-yl]hexanoyl}-1,3-thiazolidine, 3-{(S)-2-amino-6-[4-(1-isoquinolyl)piperazin-1-yl]hexanoyl}-1,3-thiazolidine, 3-{(S)-2-amino-6-[4-(4-cyano-1-isoquinolyl)piperazin-1-yl]hexanoyl}-1,3-thiazolidine, 3-{(S)-2-amino-6-[4-(4-quinolyl)piperazin-1-yl]hexanoyl}-1,3-thiazolidine, 3-1(S)-2-amino-6-[4-(2-methyl-4-quinolyl)piperazin-1-yl]hexanoyl}-1,3-thiazolidine, 3-{(S)-2-amino-6-[4-(2-trifluoromethyl-6-methoxy-4-quinolyl)piperazin-1-yl]hexanoyl}-1,3-thiazolidine, 3-1(S)-2-amino-6-[4-(2-trifluoromethyl-8-methoxy-4-quinolyl)piperazin-1-yl]hexanoyl}-1,3-thiazolidine, 3-{(S)-2-amino-6-[4-(6-chloro-2-trifluoromethyl-4-quinolyl)piperazin-1-yl]hexanoyl}-1,3-thiazolidine, 3-{(S)-2-amino-6-[4-(2-trifluoromethyl-6,8-dimethoxy-4-quinolyl)piperazin-1-yl]hexanoyl}-1,3-thiazolidine, 3-{(S)-2-amino-6-[4-(2-cyano-4-quinolyl)piperazin-1-yl]hexanoyl}-1,3-thiazolidine, 3-{(S)-2-amino-6-[4-(4-quinazolinyl)piperazin-1-yl]hexanoyl}-1,3-thiazolidine, 3-{(S)-2-amino-6-[4-(2-trifluoromethyl-4-quinazolinyl)piperazin-1-yl]hexanoyl}-1,3-thiazolidine, 3-1(S)-2-amino-6-[4-(2-benzimidazolyl)piperazin-1-yl]hexanoyl}-1,3-thiazolidine, 3-{(S)-2-amino-6-[4-(5-cyano-2-benzimidazolyl)piperazin-1-yl]hexanoyl}-1,3-thiazolidine, 3-{(S)-2-amino-6-[4-(1-methyl-2-benzimidazolyl)piperazin-1-yl]hexanoyl}-1,3-thiazolidine, 3-{(S)-2-amino-6-[4-(1-phenyl-2-benzimidazolyl)piperazin-1-yl]hexanoyl}-1,3-thiazolidine, 3-{(S)-2-amino-6-[4-(2-benzoxazolyl)piperazin-1-yl]hexanoyl}-1,3-thiazolidine, 3-{(S)-2-amino-6-[4-(5-cyano-2-benzoxazolyl)piperazin-1-yl]hexanoyl}-1,3-thiazolidine, 3-{(S)-2-amino-6-[4-(5-methoxy-2-benzoxazolyl)piperazin-1-yl]hexanoyl}-1,3-thiazolidine, 3-{(S)-2-amino-6-[4-(2-benzothiazolyl)piperazin-1-yl]hexanoyl}-1,3-thiazolidine, 3-{(S)-2-amino-6-[4-(5-cyano-2-benzothiazolyl)piperazin-1-yl]hexanoyl}-1,3-thiazolidine, 3-{(S)-2-amino-6-[4-(5-methoxy-2-benzothiazolyl)piperazin-1-yl]hexanoyl}-1,3-thiazolidine, 3-{(S)-2-amino-6-[4-(5-chloro-2-benzothiazolyl)piperazin-1-yl]hexanoyl}-1,3-thiazolidine, 3-{(S)-2-amino-6-[4-(6-cyano-2-benzothiazolyl)piperazin-1-yl]hexanoyl}-1,3-thiazolidine, 3-{(S)-2-amino-6-[4-(6-methoxy-2-benzothiazolyepiperazin-1-yl]hexanoyl}-1,3-thiazolidine, 3-{(S)-2-amino-6-[4-(6-chloro-2-benzothiazolyl)piperazin-1-yl]hexanoyl}-1,3-thiazolidine, 3-{(S)-2-amino-6-[4-(3-benz[d]isoxazolyl)piperazin-1-yl]hexanoyl}-1,3-thiazolidine, 3-{(S)-2-amino-6-[4-(5-cyano-3-benz[d]isoxazolyl)piperazin-1-yl]hexanoyl}-1,3-thiazolidine, 3-{(S)-2-amino-6-[4-(3-benz[d]isothiazolyl)piperazin-1-yl]hexanoyl}-1,3-thiazolidine, 3-{(S)-2-amino-6-[4-(1-phenyl-5-pyrazolyl)piperidino]hexanoyl}-1,3-thiazolidine, 3-{(S)-2-amino-6-[4-(3-methyl-1-phenyl-5-pyrazolyl)piperidino]hexanoyl}-1,3-thiazolidine, 3-((S)-2-amino-6-{4-[1-(pyridin-2-yl)-5-pyrazolyl]piperidino}hexanoyl)-1,3-thiazolidine, 3-((S)-2-amino-6-{4-[4-(4-cyanophenyl)-2-thiazolyl]piperidino}hexanoyl)-1,3-thiazolidine, 3-{(S)-2-amino-6-[4-(1-phenyl-1H-tetrazol-5-yl)piperidino]hexanoyl}-1,3-thiazolidine, 3-{(S)-2-amino-6-[4-(2-benzimidazolyl)piperidino]hexanoyl}-1,3-thiazolidine, 3-{(S)-2-amino-6-[4-(2-benzimidazolyl)piperidino]hexanoyl}-1,3-thiazolidine, 3-{(S)-2-amino-6-[4-(5-cyano-2-benzimidazolyl)piperidino]hexanoyl}-1,3-thiazolidine, 3-{(S)-2-amino-6-[4-(1-methyl-2-benzimidazolyl)piperidino]hexanoyl}-1,3-thiazolidine, 3-{(S)-2-amino-6-[4-(1-phenyl-2-benzimidazolyl)piperidino]hexanoyl}-1,3-thiazolidine, 3-{(S)-2-amino-6-[4-(2-benzoxazolyl)piperidino]hexanoyl}-1,3-thiazolidine, 3-{(S)-2-amino-6-[4-(5-cyano-2-benzoxazolyl)piperidino]hexanoyl}-1,3-thiazolidine, 3-{(S)-2-amino-6-[4-(5-methoxy-2-benzoxazolyl)piperidino]hexanoyl}-1,3-thiazolidine, 3-{(S)-2-amino-6-[4-(5-chloro-2-benzoxazolyl)piperidino]hexanoyl}-1,3-thiazolidine, 3-{(S)-2-amino-6-[4-(2-benzothiazolyl)piperidino]hexanoyl}-1,3-thiazolidine, 3-{(S)-2-amino-6-[4-(5-cyano-2-benzothiazolyl)piperidino]hexanoyl}-1,3-thiazolidine, 3-{(S)-2-amino-6-[4-(5-methoxy-2-benzothiazolyl)piperidino]hexanoyl}-1,3-thiazolidine, 3-{(S)-2-amino-6-[4-(5-chloro-2-benzothiazolyl)piperidino]hexanoyl}-1,3-thiazolidine, 3-{(S)-2-amino-6-[4-(6-cyano-2-benzothiazolyl)piperidino]hexanoyl}-1,3-thiazolidine, 3-{(S)-2-amino-6-[4-(6-methoxy-2-benzothiazolyl)piperidino]hexanoyl}-1,3-thiazolidine, 3-{(S)-2-amino-6-[4-(6-chloro-2-benzothiazolyl)piperidino]hexanoyl}-1,3-thiazolidine, 3-{(S)-2-amino-6-[4-(3-benz[d]isoxazolyl)piperidino]hexanoyl}-1,3-thiazolidine, 3-{(S)-2-amino-6-[4-(5-cyano-3-benz[d]isoxazolyl)piperidino]hexanoyl}-1,3-thiazolidine, 3-{(S)-2-amino-6-[4-(3-benz[d]isothiazolyl)piperidino]hexanoyl}-1,3-thiazolidine, 3-{(2S,4S)-4-[4-(5,6-dicyano-2-pyridyl)-1-piperazinyl]-2-pyrrolidinylcarbonyl}-1,3-thiazolidine, 3-{(2S,4S)-4-[4-(3-nitro-2-pyridyl)-1piperazinyl]-2-pyrrolidinylcarbonyl}-1-3-thiazolidine, 3-{(2S,4S)4-[4-(2-cyano-4-pyrimidinyl)-1piperazinyl]-2-pyrrolidinylcarbonyl}-1,3-thiazolidine, 3-{(2S,4S)-4-[4-(4-cyano-2-phenylphenyl)-1-piperazinyl]-2-pyrrolidinylcarbonyl}-1,3-thiazolidine, 3-{(2S,4S)-4-[4-(4-cyano-2-pyridylphenyl)-1piperazinyl]-2-pyrrolidinylcarbonyl}-1,3-thiazolidine, 3-{(2S,4S)-4-[4-(5-cyano-3-phenyl-2-pyridyl)-1-piperazinyl]-2-pyrrolidinylcarbonyl}-1,3thiazolidine, 3-{(2S,4S)-4-[4-(1-phenyl-2-pyrrolyl)-1-piperazinyl]-2-pyrrolidinylcarbonyl}-1,3-thiazolidine, 3-{(2S,4S)-4-[4-[1-(2-pyridyl)-2-pyrrolyl]-1-piperazinyl]-2-pyrrolidinylcarbonyl}-1,3-thiazolidine, 3-((2S,4S)-4-{4-[4-methyl-1-(2-pyridyl)-2-pyrrolyl]-1-piperazinyl}-2-pyrrolidinylcarbonyl)-1,3-thiazolidine, 3-{(2S,4S)-4-[4-(1,3-dimethyl-5-pyrazolyl)-1-piperazinyl]-2-pyrrolidinylcarbonyl}-1,3-thiazolidine, 3-((2S,4S)-4-{4-[1-(2-pyridyl)-5-pyrazolyl]-1-piperazinyl}-2-pyrrolidinylcarbonyl)-1,3-thiazolidine, 3-((2S,4S)-4-{4-[3-methyl-1-(2-methylphenyl)-5-pyrazolyl]-1-piperazinyl}-2-pyrrolidinylcarbonyl)-1,3-thiazolidine, 3-((2S,4S)-4-{4-[3-methyl-1-(3-methylphenyl)-5-pyrazolyl]-1-piperazinyl}-2-pyrrolidinylcarbonyl)-1,3-thiazolidine, 3-((2S,4S)-4-{4-[3-methyl-1-(4-methylphenyl)-5-pyrazolyl]-1-piperazinyl}-2-pyrrolidinylcarbonyl)-1,3-thiazolidine, 3-((2S,4S)-4{4-[1-(2-methoxyphenyl)-3-methyl-5-pyrazolyl]-1-piperazinyl}-2-pyrrolidinylcarbonyl)-1,3-thiazolidine, 3-((2S,4S)-4-{4-[1-(3-methoxyphenyl)-3-methyl-5-pyrazolyl]-1-piperazinyl}-2-pyrrolidinylcarbonyl)-1,3-thiazolidine, 3-((2S,4S)-4-{4{4-[1-(4-methoxyphenyl)-3-methyl-5-pyrazolyl]-1-piperazinyl}-2-pyrrolidinylcarbonyl)-1,3-thiazolidine, 3-((2S,4S)-4-{4-[1-(2-chlorophenyl)-3-methyl-5-pyrazolyl]-1-piperazinyl}-2-pyrrolidinylcarbonyl)-1,3-thiazolidine, 3-((2S,4S)-4-{4-[1-(3-chlorophenyl)-3-methyl-5-pyrazolyl]-1-piperazinyl}-2-pyrrolidinylcarbonyl)-1,3-thiazolidine, 3-((2S,4S)-4-{4-[1-(2-cyanophenyl)-3-methyl-5-pyrazolyl]-1-piperazinyl}-2-pyrrolidinylcarbonyl)-1,3-thiazolidine, 3((2S,1S)-4-{4-[1-(3cyanophenyl)-3-methyl-5-pyrazolyl]-1-piperazinyl}-2-pyrrolidinylcarbonyl)-1,3-thiazolidine, 3-((2S,4S)-4-{4-[3-methyl-1-(2-pyrimidinyl)-5-pyrazolyl]-1-piperazinyl}-2-pyrrolidinylcarbonyl)-1,3-thiazolidine, 3-((2S,4S)-4-{4-[3-methyl-1-(4-pyrimidinyl)-5-pyrazolyl]-1-piperazinyl}-2-pyrrolidinylcarbonyl)-1,3-thiazolidine, 3-((2S,4S)-4-{4-[1-(2-imidazolyl)-3-methyl-5-pyrazolyl]-1-piperazinyl}-2-pyrrolidinylcarbonyl)-1,3-thiazolidine, 3-((2S,4S)-4-{4-[3-methyl-1-(2-oxazolyl)-5-pyrazolyl]-1-piperazinyl}-2-pyrrolidinylcarbonyl)-1,3-thiazolidine, 3-((2S,4S)-4-{4-[3-trifluoromethyl-1-(2-pyridyl)-5-pyrazolyl]-1-piperazinyl}-2-pyrrolidinylcarbonyl)-1,3-thiazolidine, 3-{(2S,4S)-4-[4-(4-methyl-1-phenyl-2-imidazolyl)-1-piperazinyl]-2-pyrrolidinylcarbonyl}-1,3-thiazolidine, 3-((2S,4S)-4-{4-[1-(2-pyridyl)-2-imidazolyl]-1-piperazinyl}-2-pyrrolidinylcarbonyl)-1,3-thiazolidine, 3-((2S,4S)-4-{4-[1-(3-pyridyl)-2-imidazolyl]-1-piperazinyl}-2-pyrrolidinylcarbonyl)-1,3-thiazolidine, 3-((2S,4S)-4{4-[1-(4-pyridyl)-2-imidazolyl]-1-piperazinyl}-2-pyrrolidinylcarbonyl)-1,3-thiazolidine, 3-((2S,4S)-4-{4-[4-methyl-1-(2-pyridyl)-2-imidazolyl]-1-piperazinyl}-2-pyrrolidinylcarbonyl)-1,3-thiazolidine, 3-((2S,4S)-4-{4-[4-methyl-1-(3-pyridyl)-2-imidazolyl]-1-piperazinyl}-2-pyrrolidinylcarbonyl)-1,3-thiazolidine, 3-((2S,4S)-4-{4-[4-methyl-1-(4-pyridyl)-2-imidazolyl]-1-piperazinyl}-2-pyrrolidinylcarbonyl)-1,3-thiazolidine, 3-1(2S,4S)-4-[4-(2-phenyl-1,2,4-triazol-3-yl)-1-piperazinyl]-2-pyrrolidinylcarbonyl}-1,3-thiazolidine, 3-{(2S,4S)-4-[4-(5-methyl-2-phenyl-1,2,4-triazol-3-yl)-1-piperazinyl]-2-pyrrolidinylcarbonyl}-1,3-thiazolidine, 3-(2S,4S)-4-{4-[2-(2-pyridyl)-1,2,4-triazol-3-yl]-1-piperazinyl}-2-pyrrolidinylcarbonyl)-1,3-thiazolidine, 3-(2S,4S)-4-{4-[5-methyl-2-(2-pyridyl)-1,2,4-triazol-3-yl]-1-piperazinyl}-2-pyrrolidinylcarbonyl)-1,3-thiazolidine, 3-{(2S,4S)-4-[4-(5-phenyl-4-oxazolyl)-1-piperazinyl]-2-pyrrolidinylcarbonyl}-1,3-thiazolidine, 3-{(2S,4S)-4-[4-(2-methyl-5-phenyl-4-oxazolyl)-1-piperazinyl]-2-pyrrolidinylcarbonyl}-1,3-thiazolidine, 3-((2S,4S)-4-{4-[5-(2-pyridyl)-4-oxazolyl]-1- piperazinyl}-2-pyrrolidinylcarbonyl)-1,3-thiazolidine, 3-((2S,4S)-4-{4[2-methyl-5-(2-pyridyl)-4-oxazolyl]-1-piperazinyl}-2-pyrrolidinylcarbonyl)-1,3-thiazolidine, 3-{(2S,4S)-4-[4-(2-methyl-5-phenyl-4-thiazolyl)-1-piperazinyl]-2-pyrrolidinylcarbonyl}-1,3-thiazolidine, 3-((2S,4S)-4-{4-[2-methyl-5-(2-pyridyl)-4-thiazolyl]-1-piperazinyl}-2-pyrrolidinylcarbonyl)-1,3-thiazolidine, 3-{(2S,4S)-4-[4-(2-methyl-5-phenyl-1H-imidazol-4-yl)-1-piperazinyl]-2-pyrrolidinylcarbonyl}-1,3-thiazolidine, 3-((2S,4S)-4-{4-[2-methyl-5-(2-pyridyl)-1H-imidazol-4-yl]-1-piperazinyl}-2-pyrrolidinylcarbonyl)-1,3-thiazolidine, 3-{(2S,4S)-4-[4-(4-cyano-1-naphtyl)-1-piperazinyl]-2-pyrrolidinylcarbonyl}-1,3-thiazolidine, 3-{(2S,4S)-4-[4-(4-chloro-1-naphthyl)-1-piperazinyl]-2-pyrrolidinylcarbonyl}-1,3-thiazolidine, 3-{(2S,4S)-4-[4-(4-trifluoromethyl-1-naphthyl)-1-piperazinyl]-2-pyrrolidinylcarbonyl}-1,3-thiazolidine, 3-{(2S,4S)-4-[4-(4-trifluoromethyl-1-isoquinolyl)-1-piperazinyl]-2-pyrrolidinylcarbonyl}-1,3-thiazolidine, 3-(2S,4S)-4-[4-(3-cyano-4-quinolyl)-1-piperazinyl]-2-pyrrolidinylcarbonyl}-1,3-thiazolidine, 3-{(2S,4S)-4-[4-(2-cyano-8-methoxy-4-quinolyl)-1-piperazinyl]-2-pyrrolidinylcarbonyl}-1,3-thiazolidine, 3-{(2S,4S)-4-[4-(7-chloro-2-trifluoromethyl-4-quinolyl)-1-piperazinyl]-2-pyrrolidinylcarbonyl}-1,3-thiazolidine, 3-{(2S,4S)-4-[4-(2-trifluoromethyl-7-hydroxy-4-quinolyl)-1-piperazinyl]-2-pyrrolidinylcarbonyl}-1,3-thiazolidine, 3-((2S,4S)-4-{4-[2,7-bis(trifluoromethyl)-4-quinolyl]-1-piperazinyl}-2-pyrrolidinylcarbonyl)-1,3-thiazolidine, 3-{(2S,4S)-4-[4-(2-trifluoromethyl-5-methoxy-4-quinolyl)-1-piperazinyl]-2-pyrrolidinylcarbonyl}-1,3-thiazolidine, 3-{(2S,4S)-4-[4-(2-cyano-4-quinazolinyl)-1-piperazinyl]-2-pyrrolidinylcarbonyl}-1,3-thiazolidine, 3-{(2S,4S)-4-[4-(2-trifluoromethyl-1,8-naphthyridin-4-yl)-1-piperazinyl]-2-pyrrolidinylcarbonyl}-1,3-thiazolidine, 3-{(2S,4S)-4-[4-(2-trifluoromethyl-1,6-naphthyridin-4-yl)-1-piperazinyl]-2-pyrrolidinylcarbonyl}-1,3-thiazolidine, 3-{(2S,4S)-4-[4-(1H-indol-2-yl)-1-piperazinyl]-2-pyrrolidinylcarbonyl}-1,3-thiazolidine, 3-{(2S,4S)-4-[4-(1-phenyl-1H-indol-2-yl)-1-piperazinyl]-2-pyrrolidinylcarbonyl}-1,3-thiazolidine, 3-((2S,4S)-4-{4-[1-(2-pyridyl)-1H-indol-2yl]-1-piperazinyl}-2-pyrrolidinylcarbonyl)-1,3-thiazolidine, 3-{(2S,4S)-4-[4-(3-methyl-1-phenyl-1H-indol-2-yl)-1-piperazinyl]-2-pyrrolidinylcarbonyl}-1,3-thiazolidine, 3-{(2S,4S)-4-[4-(1-phenyl-2-benzimidazolyl)-1-piperazinyl]-2-pyrrolidinylcarbonyl}-1,3-thiazolidine, 3-((2S 4S)-4-{4-[1-(2-pyridyl)-2-benzimidazolyl]-1-piperazinyl}-2-pyrrolidinylcarbonyl)-1,3-thiazolidine, 3-{(2S,4S)-4-[4-(5-cyano-1-phenyl-2-benzimidazolyl)-1-piperazinyl]-2-pyrrolidinylcarbonyl}-1,3-thiazolidine, 3-{(2S,4S)-4-[4-(5-methoxy-1-phenyl-2-benzimidazolyl)-1-piperazinyl]-2-pyrrolidinylcarbonyl}-1,3-thiazolidine, 3{(2S,4S)-4-[4-(5-chloro-1-phenyl-2-benzimidazolyl)-1-piperazinyl]-2-pyrrolidinylcarbonyl}-1,3-thiazolidine, 3-{(2S,4S)-4-[4-(5-methoxy-1-phenyl-2-benzimidazolyl)-1-piperazinyl]-2pyrrolidinylcarbonyl}-1,3-thiazolidine, 3-{(2S,4S)-4-[4-6-methoxy-1-phenyl-2-benzimidazolyl)-1-piperazinyl]-2-pyrrolidinylcarbonyl}-1,3-thiazolidine, 3-{(2S,4S)-4-[4-6-chloro-1-phenyl-2-benzimidazolyl)-1-piperazinyl]-2-pyrrolidinylcarbonyl}-1,3-thiazolidine, 3-{(2S,4S)-4-[4-(5-methoxy-2-benzoxazolyl)-1-piperazinyl]-2-pyrrolidinylcarbonyl}-1,3-thiazolidine, 3-{(2S,4S)-4-[4-(5-chloro-2-benzoxazolyl)-1-piperazinyl]-2-pyrrolidinylcarbonyl}-1,3-thiazolidine, 3-{(2S,4S)-4-[4-(6-cyano-2-benzoxazolyl)-1-piperazinyl]-2-pyrrolidinylcarbonyl}-1,3-thiazolidine, 3-{(2S,4S)-4-[4-(6-methoxy-2-benzoxazolyl)-1-piperazinyl]-2-pyrrolidinylcarbonyl}-1,3-thiazolidine, 3-{(2S,4S)-4-[4-(6-chloro-2-benzoxazolyl)-1-piperazinyl]-2-pyrrolidinylcarbonyl}-1,3-thiazolidine, 3-{(2S,4S)-4-[4-(6-methoxy-2-oxazolo[4,5-b]pyridyl)-1-piperazinyl]-2-pyrrolidinylcarbonyl}-1,3-thiazolidine, 3-{(2S,4S)-4-[4-(6-cyano-2-oxazolo[4,5-b]pyridyl)-1-piperazinyl]-2-pyrrolidinylcarbonyl}-1,3-thiazolidine, 3-{(2S,4S)-4-[4-(5-cyano-2-oxazolo[4,5-b]pyridyl)-1-piperazinyl]-2-pyrrolidinylcarbonyl}-1,3-thiazolidine, 3-{(2S,4S)-4-[4-(1-methyl-2-phenyl-1H-indol 3-yl)-1-piperazinyl]-2-pyrrolidinylcarbonyl}-1,3-thiazolidine, 3-{(2S,4S)-4-[4-(9-acrydinyl)-1-piperazinyl]-2-pyrrolidinylcarbonyl}-1,3-thiazolidine, 3-{(2S,4S)-4-[4-(2-phenyl-1,2,4-triazol-3-yl)piperidino]-2-pyrrolidinylcarbonyl}-1,3-thiazolidine, 3-{(2S,4S)-4-[4-(5-methyl-2-phenyl-1,2,4-triazol-3-yl)piperidino]-2-pyrrolidinylcarbonyl}-1,3-thiazolidine, 3-((2S,4S)-4-{4-[2-(2-pyridyl)-1,2,4-triazol-3-yl]piperidino}-2-pyrrolidinylcarbonyl)-1 3-thiazolidine, 3-((2S,4S)-4-{4-[5-methyl-2-(2-pyridyl)-1,2,4-triazol-3-yl]piperidino}-2-pyrrolidinylcarbonyl)-1,3-thiazolidine, 3-{(2S,4S)-4-[4-(5-phenyl-4-oxazolyl)piperidino]-2-pyrrolidinylcarbonyl}-1,3-thiazolidine, 3-{(2S,4S)-4-[4-(2-methyl-5-phenyl-4-oxazolyl)piperidino]-2-pyrrolidinylcarbonyl}-1,3-thiazolidine, 3-((2S,4S)-4-{4-[5-(2-pyridyl)-4-oxazolyl]piperidino}-2-pyrrolidinylcarbonyl)-1,3-thiazolidine, 3-((2S,4S)-4-{4-[2-methyl-5-(2-pyridyl)-4-oxazolyl]piperidino}-2-pyrrolidinylcarbonyl)-1,3-thiazolidine, 3-((2S,4S)-4-[4-(5-phenyl-4-isooxazolyl)piperidino]-2-pyrrolidinylcarbonyl}-1,3-thiazolidine, 3-((2S,4S)-4-{4-[5-(2-pyridyl)-4-isooxazolyl]piperidino}-2-pyrrolidinylcarbonyl)-1,3-thiazolidine, 3-{(2S,4S)-4-[4-(5-phenyl-4-thiazolyl)piperidino]-2-pyrrolidinylcarbonyl}-1,3-thiazolidine, 3-{(2S,4S)-4-[4-(2-methyl-5-phenyl-4-thiazolyl)piperidino]-2-pyrrolidinylcarbonyl}-1,3-thiazolidine, 3-((2S,4S)-4-{4-[5-(2-pyridyl)-4-thiazolyl]piperidino}-2-pyrrolidinylcarbonyl)-1,3-thiazolidine, 3-((2S,4S)-4-{4-[2-methyl-5(2-pyridyl)-4-thiazolyl]piperidino}-2-pyrrolidinylcarbonyl)-1,3-thiazolidine, 3-{(2S,4S)-4-[4-(2-phenyl-1-pyrrolyl)piperidino]-2-pyrrolidinylcarbonyl}-1,3-thiazolidine, 3-((2S,4S)-4-{4-[2-(2-pyridyl)-1-pyrrolyl]piperidino}-2-pyrrolidinylcarbonyl)-1,3-thiazolidine, 3-{(2S,4S)-4-[4-(2-phenyl-1-imidazolyl)piperidino]-2-pyrrolidinylcarbonyl}-1,3-thiazolidine, 3-((2S,4S)-4-{4-[2-(2-pyridyl)-1-imidazolyl]piperidino}-2-pyrrolidinylcarbonyl)-1,3-thiazolidine, 3-{(2S,4S)-4[4-(4-methyl-2-phenyl-1-imidazolyl)piperidino]-2-pyrrolidinylcarbonyl}-1,3-thiazolidine, 3-((2S,4S)-4-{4-[4-methyl-2-(2-pyridyl)-1-imidazolyl]piperidino}-2-pyrrolidinylcarbonyl)-1,3-thiazolidine, 3-((2S,4S)-4-{4-[1-(4-methylphenyl)-1H-tetrazol-5-yl]piperidino}-2-pyrrolidinylcarbonyl)-1,3-thiazolidine, 3((2S,4S)-4-{4-[1-(2-fluorophenyl)-1H-tetrazol-5-yl]piperidino}-2-pyrrolidinylcarbonyl)-1,3-thiazolidine, 3-((2S,4S)-4-{4-[1-(3-fluorophenyl)-1H-tetrazol-5-yl]piperidino}-2-pyrrolidinylcarbonyl)-1,3-thiazolidine, 3-((2S,4S)-4-{4-[1-(2-pyridyl)-1H-tetrazol-5-yl]piperidino}-2-pyrrolidinylcarbonyl)-1,3-thiazolidine, 3-{(2S,4S)-4-[4(1phenyl-2-benzimidazolyl)piperidino]-2-pyrrolidinylcarbonyl}-1,3-thiazolidine, 3-{(2S,4S)-4-[4-(5-cyano-1-phenyl-2-benzimidazolyl)piperidino]-2-pyrrolidinylcarbonyl}-1,3-thiazolidine, 3-{(2S,4S)-4-[4-(5-chloro-1-phenyl-2-benzimidazolyl)piperidino]-2-pyrrolidinylcarbonyl}-1,3-thiazolidine, 3-{(2S,4S)-4-[4-(5-methoxy-1-phenyl-2-benzimidazolyl)piperidino]-2-pyrrolidinylcarbonyl}-1,3-thiazolidine, 3-{(2S,4S)-4-[4-(5-chloro-2-benzoxazolyl)piperidino]-2-pyrrolidinylcarbonyl}-1,3-thiazolidine, 3-{(2S,4S)-4-[4-(5-cyano-2-benzothiazolyl)piperidino[-2-pyrrolidinylcarbonyl}-1,3-thiazolidine, 3-{(2S,4S)-4-[4-(5- methoxy-2-benzothiazolyl)piperidino]-2-pyrrolidinylcarbonyl}-1,3-thiazolidine, 3-{(2S,4S)-4-[4-(2-oxazolo[4,5-b]pyridyl)piperidino]-2-pyrrolidinylcarbonyl}-1,3-thiazolidine, 3-{(2S,4S)-4-[4-(6-cyano-2-oxazolo[4,5-b]pyridyl)piperidino]-2-pyrrolidinylcarbonyl}-1,3-thiazolidine, 3-{(2S,4S)-4-[4-2-phenyl-1-benzimidazolyl)piperidino]-2-pyrrolidinylcarbonyl}-1,3-thiazolidine, 3-{(2S,4S)-4-[4-(5-trifluoromethyl-2-phenyl-1-benzimidazolyl)piperidino]-2-pyrrolidinylcarbonyl}-1,3-thiazolidine 3-{(2S,4S)-4-[4-(5-cyano-2-phenyl-1-benzimidazolyl)piperidino]-2-pyrrolidinylcarbonyl}-1,3-thiazolidine.

As comparison compound 1,3-L-lysyl-1,3-thiazolidine ditrifluoroacetate was synthesized according to the following method.

50% Trifluoroacetic acid/dichloromethane (8 mL) was added to the resin (1209 mg) of Example 7(1) and the mixture was stirred for 2 hr. The resin was filtered off and the filtrate was concentrated under reduced pressure. The obtained residue was purified by ISOLUTE FLUSH C18 to give the title compound (280 mg).

MS (ESI) m/z 218 [MH]$^+$

The compound of the present invention showed a potent DPP-IV inhibitory activity as demonstrated in the following Experimental Example 1.

Experimental Example 1

Plasma DPP-IV Inhibitory Activity

The plasma DPP-IV inhibitory activity of human and rat was measured according to the fluorescence assay method and under the conditions of Table 10. As a DPP-IV specific fluorescent substrate, Gly-Pro-MCA (Peptide Institute, Inc.) was used, and reaction solutions having the following compositions containing various concentrations of the test substance were incubated at room temperature for 60 min and the fluorescence intensity (Excitation 360 nm/Emission 465 nm) measured (SPECTRA FLUOR, Tecan Group, Ltd.) was taken as the DPP-IV activity.

TABLE 10

| | |
|---|---|
| rat or human plasma (10-fold dilution) | 20 μL/well |
| fluorescence substrate (100 μmol/L) | 20 μL/well |
| test substance | 20 μL/well |
| buffer (PBS containing 0.003% Brij-35) | 140 μL/well |
| total amount | 200 μL/well |

The inhibitory ratio to a solvent addition group was calculated and IC$_{50}$ value was determined by logistic analysis.

The IC$_{50}$ values of the plasma DPP-IV inhibitory activity of the present invention as determined according to the above method are shown in Tables 11 and 12.

TABLE 11

| Example compound No. | Human plasma DPP-IV inhibitory activity IC$_{50}$ (nM) | Rat plasma DPP-IV inhibitory activity IC$_{50}$ (nM) |
|---|---|---|
| 5 | 28 | 19 |
| 6 | 34 | 29 |
| 7 | 15 | 13 |
| 13 | 66 | 40 |
| 14 | 29 | 18 |
| 28 | 35 | 49 |
| comparison compound 1 | 856 | 719 |

TABLE 12

| Example compound No. | Human plasma DPP-IV inhibitory activity IC$_{50}$ (nM) | Rat plasma DPP-IV inhibitory activity IC$_{50}$ (nM) |
|---|---|---|
| 40 | 0.63 | 0.72 |
| 48 | 0.25 | 0.37 |
| 55 | 0.24 | 0.30 |
| 56 | 0.91 | 1.17 |

The comparison compound 1 is encompassed in WO99/61431. As shown in Table 11, the plasma DPP-IV inhibitory activity is sufficient.

As shown in Table 13, the plasma DPP-IV inhibitory activity of the compound of JP-T-9-509921 and the compound of WO99/61431 is not sufficient.

TABLE 13

| Known compound | Human plasma DPP-IV inhibitory activity IC$_{50}$ (nM) |
|---|---|
| (S)-2-cyano-1-L-prolylpyrrolidine hydrochloride | 2.9 |
| 3-L-prolyl-1,3-thiazolidine | 538 |

INDUSTRIAL APPLICABILITY

From the foregoing Experimental Example and various pharmacological experiments, the compounds of the present invention have a potent DPP-IV inhibitory activity, and are useful for the prophylaxis or treatment of diabetes or the prophylaxis or treatment of obesity.

This application is based on patent application Nos. 279084/2001 and 304650/2001 filed in Japan, the contents of which are hereby incorporated by reference.

The invention claimed is:
1. A thiazolidine derivative represented by the formula (I):

(I)

wherein X is a substituent of the following formula:

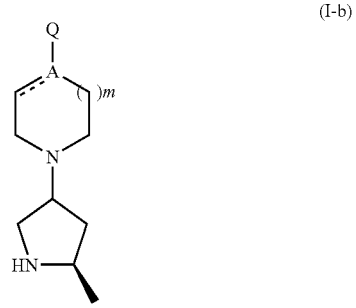

(I-b)

wherein
m is an integer of 1,
------ is a single bond or a double bond,

A is a carbon atom or a nitrogen atom,
wherein i) when A is a carbon atom, then A is optionally substituted by a hydroxyl group, carboxy or alkoxycarbonyl, and ii) when A is a nitrogen atom, then ----- is a single bond, and Q is aryl or heteroaryl selected from the compounds represented by the following formulas (II)-(XII):

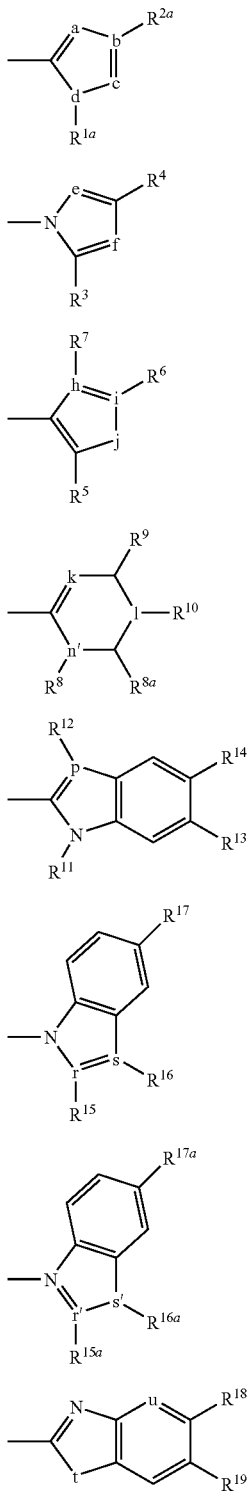

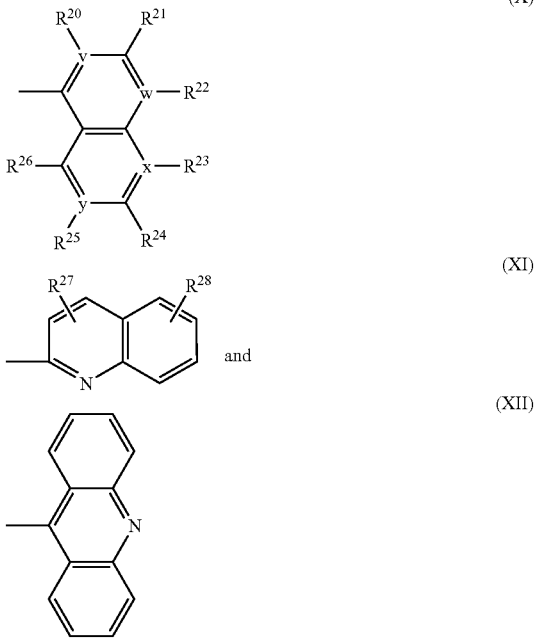

wherein
(i) in the formula (II), 1 to 3 from a, b, c and d is(are) nitrogen atom(s) and the rest is(are) carbon atom(s) or all of them are nitrogen atoms, $R^{1a}$ is alkyl, phenyl, pyridyl, pyrimidinyl, imidazolyl or oxazolyl, wherein these groups are optionally substituted by one or more from alkyl, alkoxy, halogen and cyano, $R^{2a}$ is a hydrogen atom, alkyl or haloalkyl,
wherein
(i-1) when b is a nitrogen atom, then $R^{2a}$ is not present,
(i-2) when c and d are both nitrogen atoms, a and b are both carbon atoms, $R^{1a}$ is phenyl and $R^{2a}$ is alkyl, then $R^{1a}$ has one or more substituents mentioned above,
(i-3) when a and d are both nitrogen atoms, b and c are both carbon atoms and $R^{1a}$ is phenyl without substituent, then $R^{2a}$ is alkyl or haloalkyl, and
(i-4) when all of a, b, c and d are nitrogen atoms and $R^{1a}$ is phenyl, then (1) A of the formula (I-b) is a carbon atom and $R^{1a}$ does not have the above-mentioned substituent, or (2) $R^{1a}$ is substituted by one or more from alkyl and halogen, (ii) in the formula (III), one of e and f is a nitrogen atom and the other is a carbon atom, or both are carbon atoms, and $R^3$ and $R^4$ may be the same or different and each is a hydrogen atom, alkyl, phenyl or pyridyl, (iii) in the formula (IV), j is a sulfur atom, an oxygen atom or a nitrogen atom,
h and i may be the same or different and each is a nitrogen atom or a carbon atom,
$R^5$ and $R^7$ may be the same or different and each is a hydrogen atom, phenyl or pyridyl (when h is a nitrogen atom, then $R^7$ is absent), and
$R^6$ is a hydrogen atom or alkyl (when i is a nitrogen atom, then $R^6$ is absent), (iv) in the formula (V), k, l and n' may be the same or different and each is a carbon atom or a nitrogen atom, wherein at least one is a carbon atom,
$R^8$ is a hydrogen atom, phenyl, pyridyl or nitro (when n' is a nitrogen atom, then $R^8$ is absent), $R^{8a}$ is a hydrogen atom or phenyl,
$R^9$ is a hydrogen atom, haloalkyl or cyano, and
$R^{10}$ is a hydrogen atom or cyano (when l is a nitrogen atom, then $R^{10}$ is absent),
wherein
  (iv-1) when k and n' are both nitrogen atoms, (1) A of the formula (I-b) is a nitrogen atom, and $R^{8a}$, $R^9$ and $R^{10}$ are all hydrogen atoms, or (2) $R^{8a}$ is phenyl and $R^9$ is haloalkyl,
  (iv-2) when k, l and n' are all carbon atoms, then $R^8$ is phenyl or pyridyl,
  (iv-3) when k is a nitrogen atom and l and n' are both carbon atoms, (1) $R^8$ is phenyl or nitro, or (2) $R^9$ is cyano, and
  (iv-4) when l is a nitrogen atom, then one of k and n' is a nitrogen atom,
(v) in the formula (VI), p is a nitrogen atom or a carbon atom,
$R^{11}$ is a hydrogen atom, phenyl or pyridyl (when p is a nitrogen atom, then $R^{11}$ is phenyl or pyridyl),
$R^{12}$ is a hydrogen atom or alkyl (when p is a nitrogen atom, then $R^{12}$ is absent), and
$R^{13}$ and $R^{14}$ are both hydrogen atoms, or when one of them is a hydrogen atom, then the other is cyano, alkoxy or halogen,
(vi) in the formula (VII), one of r and s is a nitrogen atom and the other is a carbon atom,
$R^{15}$ is a hydrogen atom, alkyl or phenyl (when r is a nitrogen atom, then $R^{15}$ is absent),
$R^{16}$ is a hydrogen atom or alkyl (when s is a nitrogen atom, then $R^{16}$ is absent), and
$R^{17}$ is a hydrogen atom, haloalkyl or cyano,
(vii) in the formula (VIII), r' and s' may be the same or different and each is a carbon atom or a nitrogen atom, wherein at least one of them is a nitrogen atom,
$R^{15a}$ is a hydrogen atom, alkyl or phenyl (when r' is a nitrogen atom, then $R^{15a}$ is absent),
$R^{16a}$ is a hydrogen atom or alkyl (when r' and s' are both nitrogen atoms, then $R^{16a}$ is a hydrogen atom), and
$R^{17a}$ is a hydrogen atom, haloalkyl or cyano,
(viii) in the formula (IX), t is a sulfur atom or an oxygen atom,
u is a carbon atom or a nitrogen atom, and
$R^{18}$ and $R^{19}$ are both hydrogen atoms, or one of them is a hydrogen atom and the other is cyano, alkoxy or halogen,
wherein
  (viii-1) when u is a carbon atom, then one of $R^{18}$ and $R^{19}$ is cyano, alkoxy or halogen,
  (viii-2) when t is a sulfur atom, then A in the formula (I-b) is a carbon atom, $R^{19}$ is a hydrogen atom and $R^{18}$ is methoxy or cyano,
  (viii-3) A in the formula (I-b) is a nitrogen atom, t is an oxygen atom, $R^{19}$ is a hydrogen atom, and when u is a carbon atom, then $R^{18}$ is alkoxy or halogen, and
  (viii-4) A in the formula (I-b) is a carbon atom, $R^{19}$ is a hydrogen atom, u is a carbon atom, and when t is an oxygen atom, $R^{18}$ is halogen,
(ix) in the formula (X), v, w, x and y may be the same or different and each is a carbon atom or a nitrogen atom, wherein at least two are carbon atoms,
$R^{20}$, $R^{21}$, $R^{22}$, $R^{23}$, $R^{24}$, $R^{25}$ and $R^{26}$ may be the same or different and 1 to 3 is(are) haloalkyl, methoxy, ethoxy, isopropoxy, trifluoromethoxy, 2,2,2-trifluoroethoxy, hydroxy, cyano or halogen, and the rest is(are) hydrogen atom(s) (when v is a nitrogen atom, then $R^{20}$ is absent, when w is a nitrogen atom, then $R^{22}$ is absent, when x is a nitrogen atom, then $R^{23}$ is absent, when y is a nitrogen atom, then $R^{25}$ is absent),
wherein
  (ix-1) when v is a nitrogen atom and w, x and y are all carbon atoms, then $R^{22}$ is haloalkyl,
  (ix-2) when v and w are both nitrogen atoms and x and y are both carbon atoms, then $R^{21}$ is cyano, and
  (ix-3) when w is a nitrogen atom and v, x and y are all carbon atoms, then (1) $R^{21}$ is a hydrogen atom and $R^{20}$ is cyano, (2) $R^{21}$ is haloalkyl and $R^{23}$ is hydroxy, ethoxy, isopropoxy, trifluoromethoxy or 2,2,2-trifluoroethoxy, (3) $R^{21}$ is haloalkyl and $R^{23}$ and $R^{25}$ are both methoxy, (4) $R^{21}$ is haloalkyl and $R^{24}$ is hydroxy, chloro or trifluoromethyl, (5) $R^{21}$ is haloalkyl and $R^{25}$ is hydroxy or trifluoromethoxy, (6) $R^{21}$ is haloalkyl and $R^{26}$ is methoxy, or (7) $R^{21}$ is cyano and $R^{23}$ is methoxy, and
(x) in the formula (XI), $R^{27}$ and $R^{28}$ may be the same or different and each is haloalkyl or alkoxy;
Y is methylene, hydroxymethylene, a sulfur atom, sulfinyl or sulfonyl; and
Z is a hydrogen atom or cyano;
wherein when X is a substituent represented by the formula (I-a), then Z is a hydrogen atom, or a pharmaceutically acceptable salt thereof.

2. A pharmaceutical composition comprising the thiazolidine derivative of claim 1 or a pharmaceutically acceptable salt thereof, and a pharmacologically acceptable carrier.

3. A method of inhibiting DPP-IV, which method comprises administering the thiazolidine derivative of claim 1 or a pharmaceutically acceptable salt thereof to a patient in need thereof, whereupon DPP-IV is inhibited.

4. A method of treating type 2 diabetes, which method comprises administering the thiazolidine derivative of claim 1 or a pharmaceutically acceptable salt thereof to a patient in need thereof, whereupon type 2 diabetes is treated.

5. A method of treating obesity, which method comprises administering the thiazolidine derivative of claim 1 or a pharmaceutically acceptable salt thereof to a patient in need thereof, whereupon obesity is treated.

* * * * *

UNITED STATES PATENT AND TRADEMARK OFFICE
CERTIFICATE OF CORRECTION

PATENT NO. : 7,790,725 B2
APPLICATION NO. : 11/774941
DATED : September 7, 2010
INVENTOR(S) : Sakashita et al.

Page 1 of 1

It is certified that error appears in the above-identified patent and that said Letters Patent is hereby corrected as shown below:

Claim 1, column 81, lines 53-61, formula VIII should read:

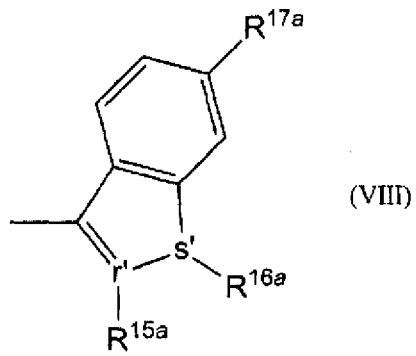

(VIII)

Signed and Sealed this
Fourteenth Day of June, 2011

David J. Kappos
*Director of the United States Patent and Trademark Office*